(12) United States Patent
Phillips et al.

(10) Patent No.: US 9,180,177 B2
(45) Date of Patent: Nov. 10, 2015

(54) BACTERIAL RIBONUCLEIC ACID CELL WALL COMPOSITIONS AND METHODS OF MAKING AND USING THEM

(71) Applicant: Bioniche Urology IP Inc., Belleville (CA)

(72) Inventors: Nigel C. Phillips, Pointe-Claire (CA); Danbing Ke, Kirkland (CA); Zdenek Richard Holan, Montreal (CA); Mohamed Elrafih, Belleville (CA)

(73) Assignee: Bioniche Urology IP Inc., Ontario (CA)

( * ) Notice: Subject to any disclaimer, the term of this patent is extended or adjusted under 35 U.S.C. 154(b) by 0 days.

(21) Appl. No.: 14/188,825

(22) Filed: Feb. 25, 2014

(65) Prior Publication Data
US 2014/0322372 A1  Oct. 30, 2014

Related U.S. Application Data

(62) Division of application No. 13/701,954, filed as application No. PCT/IB2011/054539 on Oct. 13, 2011, now Pat. No. 9,044,422.

(60) Provisional application No. 61/392,498, filed on Oct. 13, 2010, provisional application No. 61/393,589, filed on Oct. 15, 2010.

(51) Int. Cl.
| | |
|---|---|
| *A61K 31/7105* | (2006.01) |
| *A61K 35/74* | (2015.01) |
| *A61K 39/04* | (2006.01) |
| *A61K 39/39* | (2006.01) |
| *C12N 1/06* | (2006.01) |
| *A61K 39/00* | (2006.01) |

(52) U.S. Cl.
CPC ............ *A61K 39/04* (2013.01); *A61K 31/7105* (2013.01); *A61K 35/74* (2013.01); *A61K 39/39* (2013.01); *C12N 1/06* (2013.01); *A61K 2039/53* (2013.01); *A61K 2039/55555* (2013.01); *A61K 2039/55594* (2013.01)

(58) Field of Classification Search
None
See application file for complete search history.

(56) References Cited

U.S. PATENT DOCUMENTS

| | | | |
|---|---|---|---|
| 4,744,984 | A | 5/1988 | Ragland |
| 5,759,554 | A | 6/1998 | Alkemade et al. |
| 6,139,844 | A | 10/2000 | Alkemade et al. |
| 6,326,357 | B1 | 12/2001 | Phillips et al. |
| 6,329,347 | B1 | 12/2001 | Phillips et al. |
| 6,794,368 | B1 | 9/2004 | Phillips et al. |
| 6,809,081 | B1 | 10/2004 | Phillips et al. |
| 6,890,911 | B1 | 5/2005 | Phillips et al. |
| 7,125,858 | B2 | 10/2006 | Filion et al. |
| 9,044,422 | B2 | 6/2015 | Phillips et al. |
| 2013/0142828 | A1 | 6/2013 | Phillips et al. |
| 2014/0170189 | A1 | 6/2014 | Phillips et al. |

FOREIGN PATENT DOCUMENTS

| | | |
|---|---|---|
| AU | 2011315093 | 1/2014 |
| CN | 1290171 | 4/2001 |
| CN | 103354833 | 10/2013 |
| JP | 08508976 | 9/1996 |
| WO | 9907383 | 2/1999 |
| WO | 2012049654 | 4/2012 |

OTHER PUBLICATIONS

U.S. Appl. No. 131701,954, Final Office Action mailed Dec. 8, 2014, 7 pages.
Singapore Patent Application No. 201302735-4, Search Report and Written Opinion mailed on Nov. 3, 2014, 23 pages.
Chinese Application No. 201180059883.8, Office Action mailed on Dec. 31, 2014, 11 pages (containing 5 pages of English translation and 6 pages of the original document).
"AC Broth", Retrieved online at URL: www.bd.com/ds/technicalCenter/misc/difcobblmanual__2nded__lowres.pdf, 2009, pp. 35-36.
"Becton Dickinson Catalogue", Dec. 2006, BBL™, Middlebrook 7H9 Broth with Glycerol [online] [retrieved on Dec. 20, 2011] (3 pages).
"Middlebrook 7H9 Broth", Difco & BBL Manual, 2nd Edition, Retrieved from the Internet: URL: http://www.bd.com/europe/regulatory/Assets/IFU/Difco__BBL/212352.pdf [Retrieved on Oct. 23, 2013], Sep. 16, 2009, 1 page.
"Proteinase K Solution", Ambion by Life Technologies, Catalog No. AM2546, AM 2548, Pub. No. 4393871, Rev. C, Nov. 2, 2012, 2 pages.
"Proteinase K Solution", Life Technologies, Product Code AM2548, Feb. 9, 2012, 6 pages.
"Quebact", Sep. 22, 2000, Middlebrook 7H9 Broth [online] [retrieved on Dec. 21, 2011. Retrieved from http://www.quebact.com/index.php/en/support/technical-data/151-2488 (5 pages).
U.S. Appl. No. 13/701,954 , "Non Final Office Action", Sep. 11, 2013, 7 pages.
Acuna et al., "Effect of immunomodulation on estrogen alpha and progesterone receptor expression in endometrial tissue of healthy resistant mares to endometritis during the estrous cycle", Abstract submitted for: International Congress on Animal Reproduction (ICAR), Budapest, Hungary, Jul. 13-17, 2008. Reproduction in Domestic Animals;43: 97-97 Suppl.3 Jul. 2008.
Acuna et al., "Effect of immunonomodulation on oxytocin receptor in the endometrium of healthy endometritis resistant mares", Presented at: XI Conference Annual Da Abraveq, Sao Paulo, Brazil. Jun. 12-13, 2010; Published: Proceedings pp. 316-317.
Australian Application No. AU2011315093 , "Office Action", Jan. 23, 2013, pp. 3.

(Continued)

*Primary Examiner* — Brian J Gangle
(74) *Attorney, Agent, or Firm* — Kilpatrick Townsend & Stockton LLP

(57) ABSTRACT

The present invention relates to novel bacterial and mycobacterial compositions containing RNA and cell walls, and methods for making and using these compositions. These compositions have immune stimulating and anti-cancer activity.

36 Claims, 10 Drawing Sheets

(56) References Cited

OTHER PUBLICATIONS

Australian Application No. AU2011315093, "Office Action Response", Apr. 11, 2013, 15 pages.
Ausubel et al., "Chapter 2: Preparation and Analysis of DNA", Short Protocols in Molecular Biology, Fourth Edition, 1999, pp. 2-1 to 2-15.
Blobel et al., "Relation of Ribonuclease and Ribonuclease Inhibitor to the Isolation of Polysomes from Rat Liver", PNAS, Biochemistry, vol. 55, 1966, 1283-1288.
Canadian Application No. CA2,799,442, "Office Action", Jan. 21, 2013, 3 Pages.
Canadian Application No. CA2,799,442, "Office Action", Nov. 6, 2013, 5 pages.
Canadian Application No. CA2799442, "Response to Office Action issued Jan. 21, 2013", Apr. 18, 2013, 22 pages.
China Application No. CN2,799,442, "Office Action", Jul. 10, 2013, 6 Pages.
Dole et al., "Microdetermination of Long-Chain Fatty Acids in Plasma and Tissues", Journal of Biological Chemistry, vol. 235, No. 9, 1960, pp. 2595-2599.
Dragon et al., "The use of immunomodulation with Mycobacterial cell wall-DNA complex (MCC) as a potential treatment for Endometritis in cattle", 16th International Congress on Animal Reproduction. Jul. 13-17, 2008. Budapest, Hungary. Reproduction in Domestic Animals vol. 43 S(3) 61.
EP11832218.9, "Extended European Search Report", Nov. 13, 2013, 17 pages.
Filion et al., "In Vitro Activity of Mycobacterial Cell Wall-DNA Complex (MCC) Towards Ovarian Cancer Cells", 4th Conference on Ovarian Cancer Research.
Filion et al., "Mycobacterial Cell Wall DNA Complex (MCC) Induces Apoptosis Markers and a Cytokine Profile Distinct from BCG Following Repeated Intravesical Administration", Canadian Journal of Urology 2006;13(3):3109.
Filion et al., "Anticancer Activity of Mycobacterial Cell Wall-DNA Complex (MCC) in a Model of Rat Colon Cancer Peritoneal Carcinomatosis", American Association for Cancer Research (AACR) Annual Meeting 2007.
Filion et al., "Preclinical evaluation of the tolerability and the anticancer activity of mycobacterial cell wall-DNA complex (MCC) after intraperitoneal administration using a rat peritoneal DHD/K12/PROb colon carcinomatosis model", Abstract to 5th World Pharmaceutical Congress, Philadelphia, PA, USA (May 23-24, 2006).
Filion et al., "Treatment of Experimental Colon Cancer Peritoneal Carcinomatosis in Rats With Mycobacterial Cell Wall-DNA Complex (MCC)", 12th World Congress on Gastrointestinal Cancer, Jun. 2010.
Fisher, "Apoptosis in Cancer Therapy: Crossing the Threshold", Cell, vol. 78, Aug. 26, 1994, pp. 539-542.
Fox et al., "Isolation of a Soluble Resistance-Enhancing Factor from *Mycobacterium phlei*", Journal of Bacteriology, 92(2), pp. 285-290, 1966.
Fox et al., "Stimulation of Nonspecific Resistance to Infection by a Crude Cell Wall Preparation from *Mycobacterium phlei*", Journal of Bacteriology, 92(1), pp. 1-5, 1966.
Gerbaut et al., "Is Standardization More Important than Methodology for Assay of Total Protein in Cerebrospinal Fluid?", Clinical Chemistry, vol. 32, No. 2, 1986, pp. 353-355.
Gil et al., "Infectious Complication in 314 Patients after High-Dose Therapy and Autologous Hematopoietic Stem Cell Transplantation: Risk Factors Analysis and Outcome", Infection, vol. 35, No. 6, 2007, pp. 421-427.
Gonzalez-Y-Merchand et al., "Strategies Used by Pathogenic and Nonpathogenic Mycobacteria to Synthesize rRNA", Journal of Bacteriology, vol. 179, No. 22, Nov. 1997, pp. 6949-6958.
Grange et al., "The use of mycobacterial adjuvant-based agents for immunotherapy of cancer", Vaccine, Sep. 15, 2008, vol. 26(39), ISSN: 0264-410X, pp. 4984-4990 (7 pages), Sep. 15, 2008, pp. 4984-4990.

Hsu et al., "Vaccination of Patients with B-Cell Lymphoma Using Autologous Antigen-Pulsed Dendritic Cells", Nature Medicine, vol. 2, No. 1, Jan. 1996, pp. 52-58.
Ilic et al., "Single Cell Detection with Micromechanical Oscillators", Journal of Vacuum Science & Technology B, vol. 19, No. 6, Nov./Dec. 2001, pp. 2825-2828.
Johrer et al., "Tumour-Immune Cell Interactions Modulated by Chemokines", Expert Opinion on Biological Therapy, vol. 8, No. 3, Mar. 2008, pp. 269-290.
Joos et al., "Breakdown of Pulmonary Host Defense in the Immunocompromised Host", Proceedings of the American Thoracic Society, vol. 2, 2005, pp. 445-448.
Kanai et al., "Immunogenicity of Intracellular Particles and Cell Walls from *Mycobacterium tuberculosis*", Journal of Bacteriology, 80(5), pp. 607-614, 1960.
Kanai et al., "Allergencity of Intracellular Particles, Cell Walls, and Cytoplasmic Fluid from *Mycobacterium tuberculosis*", Journal of Bacteriology, 80(5), pp. 615-620, 1960.
Keller et al., "Empirical Statistical Model to Estimate the Accuracy of Peptide Identifications Made by MS/MS and Database Search", Analytical Chemistry, vol. 74, 2002, pp. 5383-5392.
Kim et al., "Carcinoma Produced Factors Activate Myeloid Cells via TLR2 to Stimulate Metastasis", Nature, vol. 457, No. 7225, Jan. 1, 2009, pp. 102-106.
Knapp et al., "Antitumor Activity of Mycobacterial Cell Wall-DNA Complex (MCC) Against Canine Urinary Bladder Transitional Cell Carcinoma Cells", 24th Annual Conference of the Veterinary Cancer Society, Kansas City, Missouri, Nov. 3-6, 2004.
Kopper et al., "Experimental Model for Liver Metastasis Formation Using Lewis Lung Tumor", Journal of Cancer Research & Clinical Oncology, vol. 103, 1982, pp. 31-38.
Koya et al., "Complications of Intravesical Therapy for Urothelial Cancer of the Bladder", The Journal of Urology, vol. 175, Jun. 2006, pp. 2004-2010.
Lamm et al., "Apparent Failure of Current Intravesical Chemotherapy Prophylaxis to Influence the Long-Term Course of Superficial Transitional Cell Carcinoma of the Bladder", The Journal of Urology, vol. 153, May 1995, pp. 1444-1450.
Le Roes-Hill et al., "*Streptomyces polyantibioticus* sp. nov., isolated from the banks of a river", International Journal of Systematic and Evolutionary Microbiology, 2009, ISSN: 1466-5034, pp. 1302-1309 (*p. 1303, left column, 2nd paragraph*) (8 pages).
Levine, "p53, The Cellular Gatekeeper for Growth and Division", Cell, vol. 88, Feb. 7, 1997, pp. 323-331.
Liang et al., "Study on a Hidden Protein-DNA Binding in Salmon Sperm DNA Sample by Dynamic Kinetic Capillary Isoelectric Focusing", Analytica Chimica Acta, vol. 650, 2009, pp. 106-110.
Ligo et al., "Therapeutic Activity and Tissue Distribution of ME2303, A New Anthracycline Containing Fluorine, and Its Metabolites in Mice Bearing Hepatic Metastases of Lewis Lung Carcinoma", Anti-Cancer Drugs, vol. 1, Oct. 1990, pp. 77-82.
Lyon et al., "Uptake and Distribution of Labeled Carbon from 14C-Asparagine by *Mycobacterium tuberculosis*", Journal of Bacteriology, vol. 98, No. 1, Apr. 1969, pp. 317-318.
Menard et al., "Effect of formulation on the direct anticancer activity of Mycobacterial cell wall-DNA complex (MCC) against human bladder cancer cell lines", The Canadian Journal of Urology: 13(3): 3109; Jun. 2006. Published: Abstract/Poster No. 198.
Middleberg, "Process-Scale Disruption of Microorganisms", Biotechnology Advances, vol. 13, Issue 3, 1995, pp. 491-551.
Millman et al., "Effect of the H37Ra Strain of *M. tuberculosis* and of a Mycobacterial RNA Fraction on Tumor Growth", Experimental Biology and Medicine, vol. 147, No. 3, Abstract, Dec. 1974, pp. 765-768.
Millman et al., "Mycobacterial Ribonucleic Acid: Comparison with Mycobacterial Cell Wall Fractions for Regression of Murine Tumor Growth", Infection and Immunity, Oct. 1976, vol. 14, No. 4, pp. 929-933, ISSN: 0019-9567 (5 pages), Oct. 1, 1976, pp. 929-933.
Montoya, "Managing Hematologic Toxicities in the Oncology Patient", Journal of Infusion Nursing, vol. 30, No. 3, May-Jun. 2007, pp. 168-172.

(56) References Cited

OTHER PUBLICATIONS

Morales et al., "Mycobacterial Cell Wall-DNA Complex (MCC) in the Treatment of Refractory C-I-S of the Bladder", Presented at AUA 2002 & CUA 2002.
Morales et al., "Phase 2 study on two doses (4 and 8 mg) of Mycobacterial Cell Wall-DNA Complex (MCC) in the Treatment of CIS of the bladder", New England Section of the American Urological Association, Sep. 2003.
Morales et al., "Efficacy and safety of mycobacterial cell wall DNA complex in the treatment of patients with non-muscle invasive bladder cancer at high risk of progression and who are refractory to BCG", European Urology Supplements;10 (2): 149-149 Mar. 10, 2011.
Morales et al., "Patient's age in bladder cancer immunotherapy response and adverse events: MCC experience", Abstract for SIU World Urology Oncology Update; Santiago, Chile, Nov. 19-22, 2008; Submitted: on or before May 1, 2008.
Morales et al., "Phase 3 study to evaluate the efficacy and safety of mycobacterial cell wall DNA complex in the treatment of patients with non-muscle invasive bladder cancer at high risk of progression and who are refractory to BCG", Canadian Urological Association Annual Meeting, Montreal, Quebec Jun. 19-21, 2011.
Morales et al., "Phase 3 Study to Evaluate the Efficacy and Safety of Mycobacterial Cell Wall-DNA Complex in the Treatment of Patients With Non-Muscle Invasive Bladder Cancer at High Risk of Progression and Who Are Refractory to BCG", The Journal of Urology 185.4 (2011): e662-e663. Canadian Urological Association Annual Meeting, Montreal, Quebec Jun. 19-21, 2011 (Abstract Submitted on or before Jan. 14, 2011).
Morales et al., "Phase III Study to Evaluate the Efficacy and Safety of Mycobacterial Cell Wall-DNA Complex in the Treatment of Patients With Non-Muscle Invasive Bladder Cancer at High Risk of Progression and Who Are Refractory to BCG", American Urological Association Annual Meeting (AUA), Atlanta, GA. May 19-23, 2012.
Morales et al., "Safety of Intravesical Mycobacterial Cell Wall DNA Complex Given Immediately Postsurgery in Patients With Non-Muscle-Invasive Bladder Cancer", EN301 post-TURBT (CUA 12); Final Jan. 12, 2012.
Morales et al., "Use of Mycobacterial Cell Wall-DNA Complex Immediately After Endovesical Surgery in the Treatment of Patients With Non-Muscle-Invasive Bladder Cancer", 3rd European Multidisciplinary Meeting on Urological Cancers, Nov. 4-6, 2011, Barcelona, Spain.
Morales et al., "Use of Mycobacterial Cell Wall-DNA Complex Immediately After Endovesical Surgery in the Treatment of Patients With Non-Muscle-Invasive Bladder Cancer", European Multidisciplinary Meeting on Urological Cancers (EMUC) 2011 Abstract.
Morin et al., "Intraperitoneal anticancer activity of Mycobacterial cell wall-DNA complex (MCC) against murine peritoneal carcinomatosis", 4th Conference on Ovarian Cancer Research, Montreal 2008.
Morton et al., "Prolongation of Survival in Metastatic Melanoma After Active Specific Immunotherapy With a New Polyvalent Melanoma Vaccine", Annals of Surgery, vol. 216, No. 4, Oct. 1992, pp. 463-482.
Murphy et al., "Phase I Clinical Trial: T-Cell Therapy for Prostate Cancer Using Autologous Dendritic Cells Pulsed With HLA-A0201-Specific Peptides from Prostate-Specific Membrane Antigen", The Prostate, vol. 29, 1996, pp. 371-380.
Nestle et al., "Vaccination of melanoma patients with peptide-or tumor lysate-pulsed dendritic cells.", Nature Medicine, vol. 4, No. 3, Mar. 1, 1998, pp. 328-332.
Nesvizhskii et al., "A Statistical Model for Identifying Proteins by Tandem Mass Spectrometry", Analytical Chemistry, vol. 75, 2003, pp. 4646-4658.
Orefice et al., "Intravenous Administration of BCG in Advanced Melanoma Patients", Tumori, vol. 64, No. 4, Jul./Aug. 1978, pp. 437-443.

PCT/IB2011/054539, "International Preliminary Report on Patentability", Apr. 25, 2013, 19 pages.
PCT/IB2011/054539, "International Search Report and Written Opinion", mailed Jan. 19, 2012 (14 pages).
Peternel et al., "Isolation of Biologically Active Nanomaterial (Inclusion Bodies) From Bacterial Cells", Microbial Cell Factories, vol. 9, No. 66, 2010, pp. 1-16.
Phillips et al., "Anticancer activity of Mycobacterial cell wall-DNA (MCC) complex against rat colon peritoneal carcinomatois", World Congress on Gastrointestinal Cancer, Barcelona, Spain, Jun. 15-18, 2005; Abstract submitted on or before Mar. 21, 2005.
Phillips et al., "Mycobacterial cell wall-DNA complex (MCC) interacts rapidly with bladder cancer cells and demonstrates synergy with gemcitabine", Abstract submitted for: European Association of Urology Congress, Istanbul, Turkey. Mar. 16-19, 2005; Published: Abstract No. 71; Eur. Urol. Supp. 4(3): 20 (2005).
Phillips et al., "The Anticancer Activity of Mycobacterial Cell Wall-DNA Complex (MCC) Against Human Bladder Cancer Cell Lines is Different to BCG", Journal of Urology Suppl S 2007;177(4):294.
Phillips et al., "Anticancer activity of Mycobacterial Cell wall-DNA Complex (MCC) in a model of rat colon cancer peritoneal carcinomatosis", American Association for Cancer Research (AACR) Annual Meeting, Apr. 14-18, 2007.
Polatnick et al., "Ribonuclease Contamination of Crystalline Deoxyribonuclease, Trypsin, and of Partially Purified Foot-and-Mouth Disease Virus Preparations", Analytical Biochemistry 2, 1961, 161-168.
Pook et al., "Internalization of *Mycobacterium bovis,* Bacillus Calmette Guerin, by bladder cancer cells is cytotoxic", Oncology Reports, vol. 18, No. 5, ISSN: 1791-2431, pp. 1315-1320 (6 pages), 2007, pp. 16-24.
Puttmann et al., "Fast HPLC Determination of Serum Free Fatty Acids in the Picomole Range", Clinical Chemistry, vol. 39, No. 5, 1993, pp. 825-832.
Rathore et al., "Analysis for Residual Host Cell Proteins and DNA in Process Streams of a Recombinant Protein Product Expressed in *Escherichia coli* Cells", Journal of Pharmaceutical and Biomedical Analysis, vol. 32, 2003, pp. 1199-1211.
Ribi et al., "Effective Nonliving Vaccine Against Experimental Tuberculosis in Mice", Journal of Bacteriology, vol. 91, No. 3, Mar. 1966, pp. 975-983.
Ryan et al., "Mycobacterial Cell Wall-DNA Complex (MCC) has a Direct Anticancer Activity Against Primary Human Bladder Cancer Cell Cultures", 61st Annual Meeting of the Canadian Urological Association (CUA), 2006.
Saha et al., "Immunomodulatory Activity of Mycobacterial Cell Wall-DNA Complex (MCC) In Vitro and Following Intravenous Administration to Dogs", American College of Veterinary Internal Medicine, Abstract Only, 2005, pp. 401.
Stanford et al., "Successful Immunotherapy with *Mycobacterium vaccae* in the Treatment of Adenocarcinoma of the Lung", European Journal of Cancer, vol. 44, 2008, pp. 224-227.
Takeya et al., "Mycobacterial Cell Walls", Journal of Bacteriology,vol. 85,issue 1, Jan. 1963, pp. 16-23.
Wang et al., "Preparation of Protease-free and Ribonuclease-free Pancreatic Deoxyribonuclease", The Journal of Biological Chemistry, vol. 253, No. 20, 1978, 7216-7219.
Yarkoni et al., "Influence of Oil Concentration on the Efficacy of Tumor Regression by Emulsified Components of Mycobacteria", Cancer Research, vol. 39, Feb. 1979, pp. 535-537.
Canadian Patent Application No. 2,799,442, Office Action, mailed Feb. 25, 2014, 3 Pages.
U.S. Appl. No. 13/701,954, Non-Final Office Action mailed on Apr. 30, 2014, 7 pages.
Chinese Patent Application No. 201180059883.8, Office Action mailed Apr. 24, 2014, 14 pages.
Canadian Patent Application No. 2,799,442, Office Action mailed on Jun. 19, 2014, 4 pages.
European Application No. 11832218.9, Communication pursuant to Article 94(3) mailed Aug. 11, 2014, 14 pages.

(56) References Cited

OTHER PUBLICATIONS

Mendes et al., Clinical and immunological assessment of *Mycobacterium vaccae* (SRL172) with chemotherapy in patients with malignant mesothelioma, British Journal of Cancer, vol. 86, 2002, pp. 336-341.

U.S. Appl. No. 13/701,954, Notice of Allowance mailed Mar. 25, 2015, 7 pages.

U.S. Appl. No. 14/188,807, Non-Final Office Action mailed Mar. 27, 2015, 7 pages.

U.S. Appl. No. 14/696,728, Non-Final Office Action mailed Jun. 3, 2015, 6 pages.

Yarkoni et al., Immunotherapy of a guinea pig hepatoma with ultrasonically prepared mycobacterial vaccines, Cancer Immunology, Immunotherapy, vol. 2, Issue 2, Apr. 1977, pp. 143-146.

AU2011315093 , "Office Action Response", Sep. 3, 2013, 14 pages.

Bischoff et al., "An Adenovirus Mutant That Replicates Selectively in p53-Deficient Human Tumor Cells", Science, vol. 274, No. 5286, Oct. 18, 1996, pp. 373-376.

Bloch, M.D. et al., "Studies on the Virulence of Tubercle Bacilli: Variations in Virulence Effected by Tween 80 and Thiosemicarbazone", Applied Immunology, The Public Health Research Institute of the City of New York, Inc., New York, Jul. 1952, 1-16.

Diels et al., "High-Pressure Homogenization as a Non-Thermal Technique for the Inactivation of Microorganisms", Critical Reviews in Microbiology, vol. 32, 2006, pp. 201-216.

Filion et al., "Intravesical Treatment With Mycobacterial Cell Wall-DNA Complex (MCC) Induced a Cytokine Profile Distinct From BCG", 20th European Association of Urology Congress, Istanbul, Turkey. Mar. 16-19, 2005.

Heptinstall , "Isolation of Total RNA from Bacteria", Methods in Molecular Biology, vol. 86: RNA Isolation and Characterization Protocols, 1998, 47-53.

Hurley et al., "Rapid Lysis Technique for Mycobacterial Species", Journal of Clinical Microbiology, Nov. 1987, 2227-2229.

Labelle et al., "Inhibition of bladder cancer cell proliferation by mycobacterial cell wall-DNA complex (MCC) in combination with chemotherapeutic agents", Journal of Urology;171 (4): 190-190 Suppl.S Apr. 2004.

Martin, Jr. et al., "Preparation of Cell Walls and Protoplasm of Neisseria with the Ribi Cell Fractionator", Journal of Bacteriology, vol. 97, No. 3, Mar. 1969, 1009-1011.

Morales et al., "Intraprostatic Injection of Mycobacterial Cell Wall-DNA Complex (MCC): Pre-clinical Anticancer Activity, Toxicity and Clinical Phase-I Activity", 27th Congress of the Sociètè Internationale d'Urologie (SIU), Oct. 3-7, 2004

Morales et al., "Safety of intravesical mycobacterial cell wall-DNA complex given immediately postsurgery in patients with non-muscle-invasive bladder cancer", American Urological Association Annual Meeting (AUA), Atlanta, GA. May 19-23, 2012 Submitted Nov. 14, 2011; Published in Journal of Urology;187 (4): E719-E720 1783 Suppl.S Apr. 2012.

Morales et al., "Safety of Intravesical Mycobacterial Cell Wall-DNA Complex Given Immediately Postsurgery in Patients With Non-Muscle-Invasive Bladder Cancer", Presented in Jun. 2012 (EMUC Meeting original presentation Nov. 2011, AUA 2011)

Van Boxtel et al., "Effect of Polyoxyethylene Sorbate Compounds (Tweens) on Colonial Morphology, Growth, and Ultrastructure of *Mycobacterium paratuberculosis*", APMIS 98, 1990, 901-908.

Youmans et al., "Immunogenic Activity of a Ribosomal Fraction Obtained from *Mycobacterium tuberculosis*", Journal of Bacteriology, vol. 89, No. 5, May 1965, pp. 1291-1298.

Youmans et al., "Preparation of Highly Immunogenic Ribosomal Fractions of *Mycobacterium tuberculosis* by Use of Sodium Dodecyl Sulfate", Journal of Bacteriology, vol. 91, No. 6, Jun. 1966, pp. 2141-2145.

U.S. Appl. No. 14/188,807, Notice of Allowance mailed Jul. 16, 2015, 8 pages.

Japanese Patent Application No. 2013-533316, Office Action mailed Sep. 1, 2015 (4 pages for the original document and 5 pages for the English translation).

Youmans et al., "Factors Affecting Immunogenic Activity of Mycohacterial Ribosomal and Ribonucleic Acid Preparations", Department of Microbiology, Northwestern University Medical School, Chicago, Illinois 60611, vol. 99, No. 1, Apr. 1, 1969, pp. 42-50.

**TEM of *Mycobacterium phlei* and Mp cell wall RNC compositions**
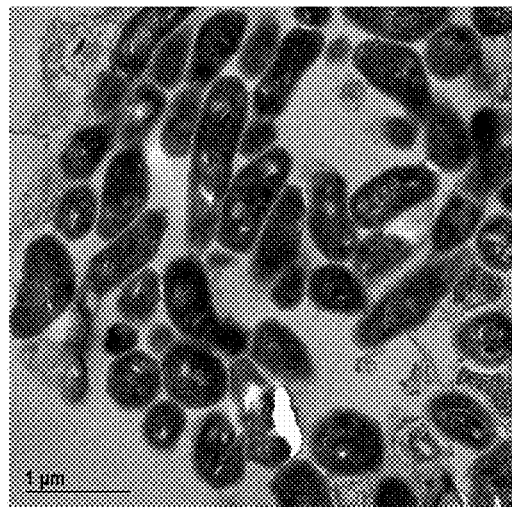
FIG. 1A: *M. phlei*
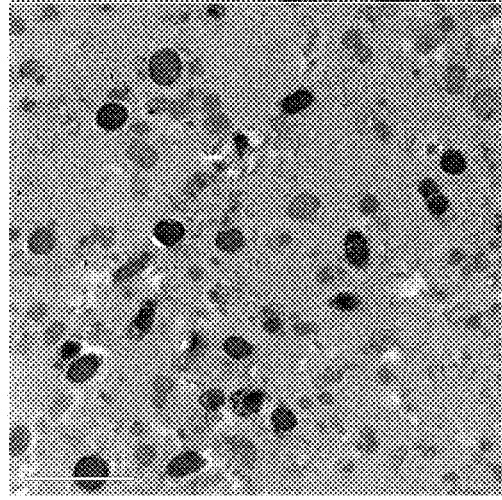
FIG. 1B: MCWE
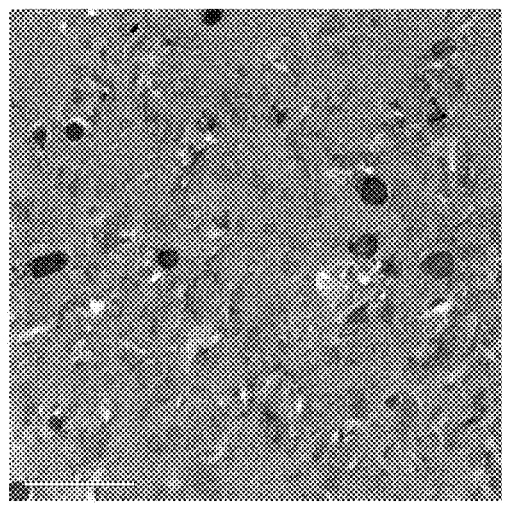
FIG. 1C: MCC

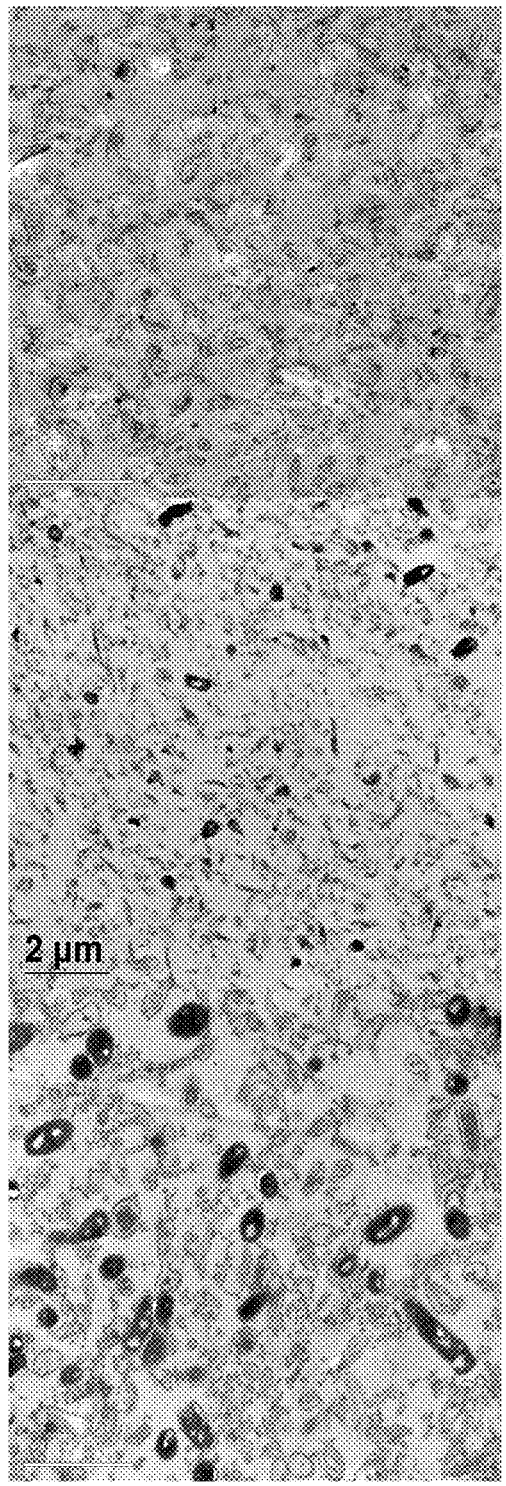
FIG. 1D: MpRNC Low
FIG. 1E: MpRNC Intermediate
FIG. 1F: MpRNC High

Electrophoretic analysis of oligonucleotide length in MpRNC
FIG. 2A
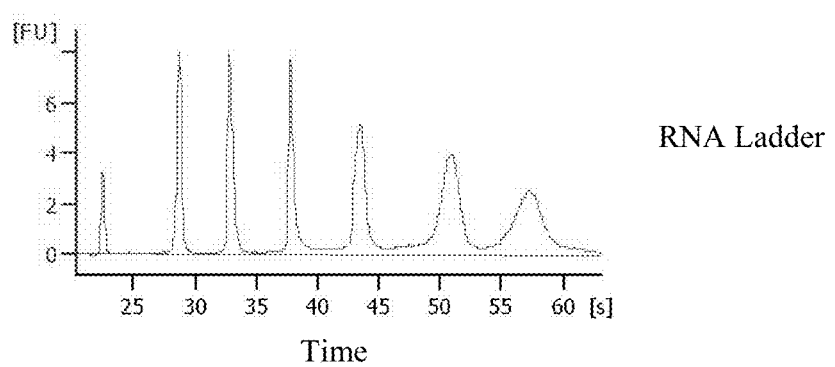
RNA Ladder
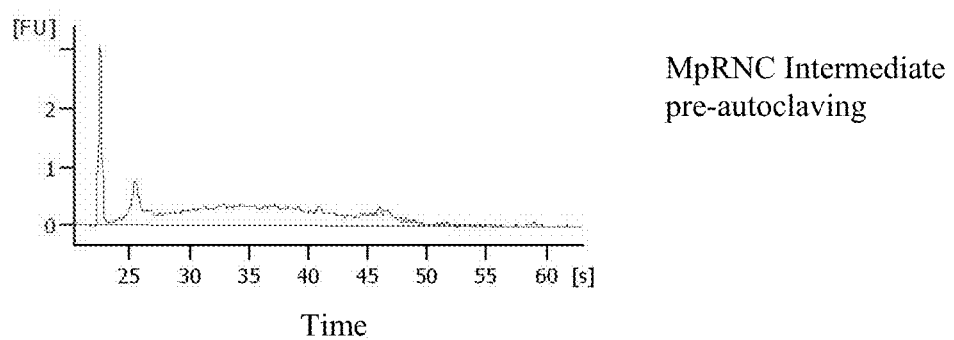
MpRNC Intermediate
pre-autoclaving Electrophoretic analysis of oligonucleotide length in MpRNC

**RNA and DNA content of MpRNC containing varying proportions of intact autoclaved *M. phlei* cells**
FIG. 3A. MpRNC High
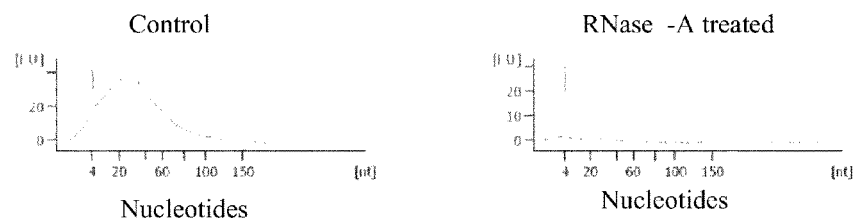
FIG. 3B. MpRNC Intermediate
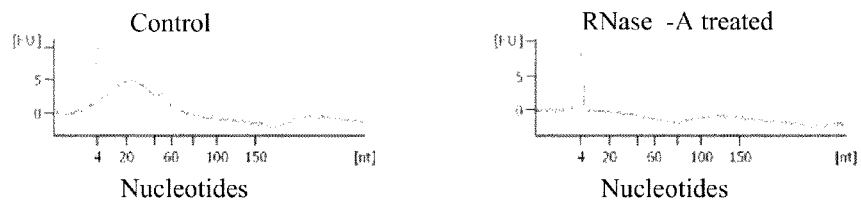
FIG. 3C. MpRNC Low
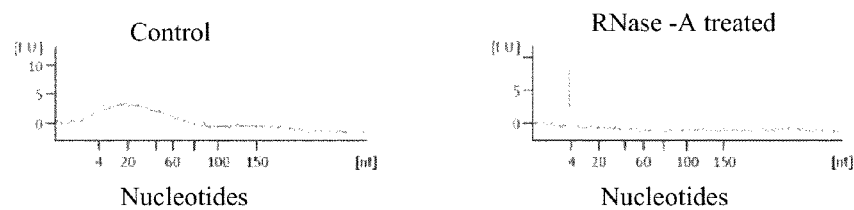
FIG. 3D. Autoclaved *M. phlei*
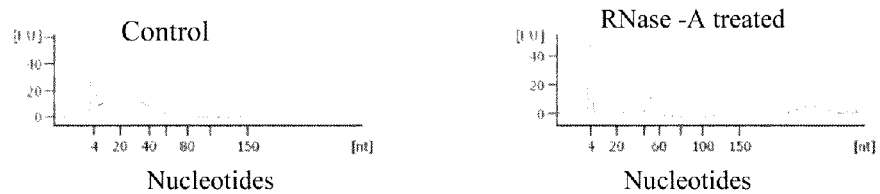

RNase-susceptible nucleic acid (NA) in MpRNC, MbRNC, MsRNC and MvRNC.

FIG. 4A. Urea-PAGE electrophoresis of untreated and RNase A treated nucleic acids

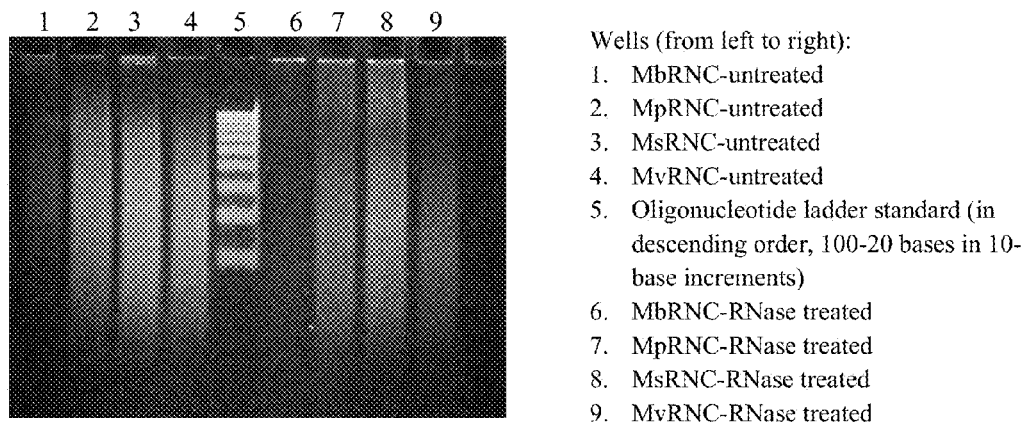

Wells (from left to right):
1. MbRNC-untreated
2. MpRNC-untreated
3. MsRNC-untreated
4. MvRNC-untreated
5. Oligonucleotide ladder standard (in descending order, 100-20 bases in 10-base increments)
6. MbRNC-RNase treated
7. MpRNC-RNase treated
8. MsRNC-RNase treated
9. MvRNC-RNase treated FIG. 4B. RNase-susceptible nucleic acids determined by scanning densitometry

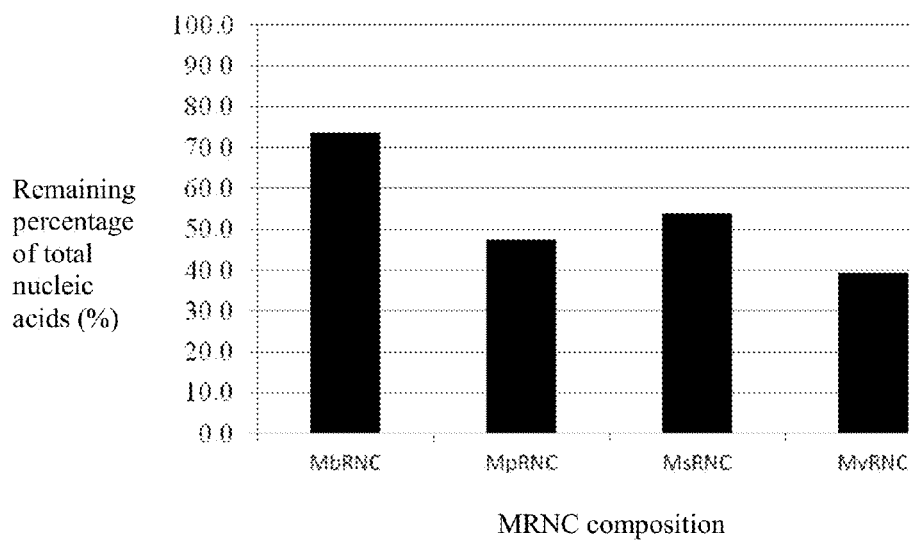

Remaining percentage of total nucleic acids (%)

MRNC composition

Mycolic acid profile of MpRNC Intermediate.

FIG. 5A. Mycolic acid profile of extractable lipids determined by RP-HPLC. Behenic acid (C22:0) was used as the standard for quantification of extractable lipids.

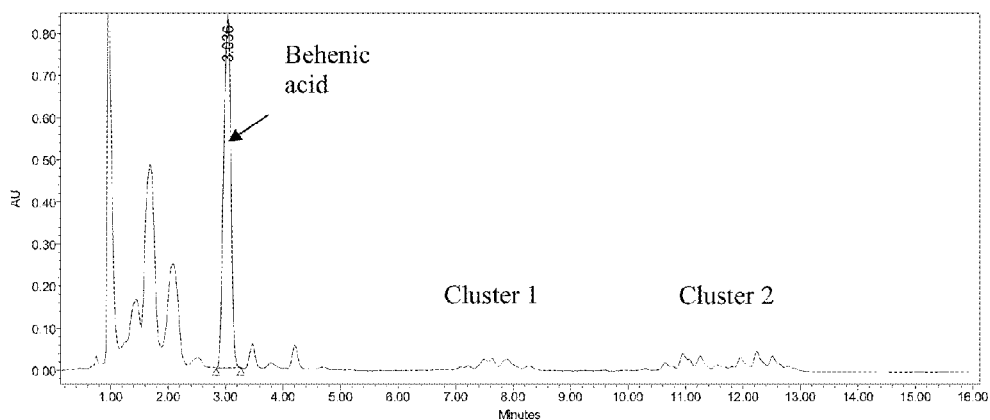

FIG. 5B. Mycolic acid profile of saponifiable lipids by RP-HPLC. Low and high mycolic acid carbon number standards (Corixa: estimated to be ~C40 and ~C110) were used as internal standards (IS) for quantification of saponifiable lipids.

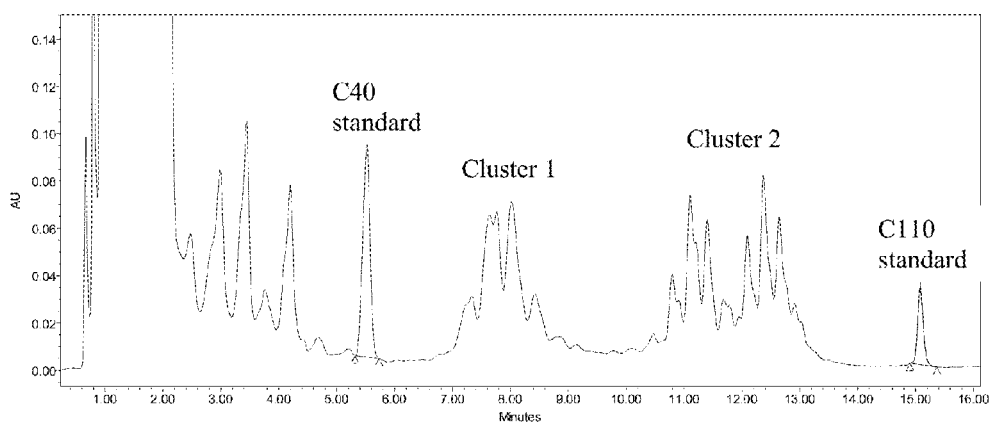

NOD2 activation by mycobacterial RNC

TLR2 activation by mycobacterial RNC.

**Stimulation of IL-10 and IL-12p40 production in human peripheral blood mononuclear cells (PBMC) by MpRNC Intermediate containing varying proportions of intact autoclaved *Mycobacterium phlei*.**

FIG. 8A. PBMC - IL-10 induction

FIG. 8B. PBMC - IL-12p40 induction

BACTERIAL RIBONUCLEIC ACID CELL WALL COMPOSITIONS AND METHODS OF MAKING AND USING THEM

PRIOR RELATED APPLICATIONS

The present application is a divisional application of U.S. application Ser. No. 13/701,954 filed Dec. 4, 2012, which is a national phase of PCT/IB2011/054539 filed Oct. 13, 2011, which claims the benefit of priority to U.S. provisional patent application 61/392,498 filed Oct. 13, 2010, and U.S. provisional patent application 61/393,589 filed Oct. 15, 2010, each of which is incorporated herein by reference in its entirety.

FIELD OF THE INVENTION

The present invention relates to novel compositions comprising bacterial RNA and bacterial cell walls and methods for making and using these compositions. These compositions have immune stimulating and anti-cancer activity.

BACKGROUND OF THE INVENTION

The treatment of cancer continues to be a problem for clinical and veterinary medicine. The treatment regimens available today include surgery, radiation, chemotherapy, immunotherapy (including autologous and heterologous cell therapy) or combinations thereof.

Surgery often fails due to tumor tissue being unrecognized and not removed. Radiation and chemotherapy also frequently fail, and the side effects of the treatments often decrease the quality of life for patients. Surgery and chemotherapy are associated with significant and often non-specific suppression of the immune system (Hammer et al., Eur. Surg. Res., 1992 24:133-137; Joos and Tam, Proc. Am. Thorac. Soc., 2005 2:445-448). This immune suppression is often associated with the occurrence of opportunistic infections, as exemplified by the known high rate of infectious complications in individuals undergoing high-dose whole-body irradiation (Gil et al., Infection, 2007 35:421-427). Radiation, surgery and chemotherapy are additionally associated with multilineage hematopoietic and myeloid suppression (myelosuppression) such as, but not limited to leucopenia, neutropenia, thrombocytopenia and/or anemia (Montoya. J. Infus. Nurs. 2007 30:168-172). These conditions may be life threatening for patients. Chemotherapy is often compromised by the presence of or subsequent development of resistance, which can often span different classes of drugs (multidrug resistance).

Immunotherapy for cancer has been employed for many years. One of the first immune treatments was a mixed bacterial vaccine (Coley's vaccine), the active ingredient of which is bacterial lipopolysaccharide. It should be noted that regulatory authorities strive to limit or eliminate the presence of lipopolysaccharide from pharmaceutical agents due to unwanted and often toxic effects. More recently, mixtures of irradiated malignant melanoma cells have been used to induce immune responses in patients with malignant melanoma, which increased survival in several patients (Morton, et al. Ann. Surg. 1992, 216:463-482). One major benefit offered by immune therapy (immunotherapy) is that it is not generally associated with the side effects of surgery, radiation or chemotherapy. In three studies using dendritic cell immunotherapy in patients with cancer, minimal to no side effects were reported (Hsu, et al. Nature Medicine, 1996 2:52-58; Murphy, et al. The Prostate, 1996 29:371-380; Nestle, et al. Nature Medicine, 1998, 4(3):328-332).

Mycobacterial cell walls are known to stimulate host immune defense mechanisms (both innate through the interaction with pathogen associated molecular pattern receptors—PAMPs, and acquired through the presence of immunogenic molecular species). Immunotherapy using whole, viable mycobacteria is used clinically in the treatment of bladder cancer. The *mycobacterium bacillus* Calmette-Guérin (BCG), an attenuated strain of *Mycobacterium bovis*, is repeatedly instilled into the bladder of individuals with bladder cancer, where possible and preferably in an adjuvant setting following tumor removal by surgery (as described in for example the European Association of Urology Guidelines 2007 edition, pages 8-9). Its use however is associated with a range of adverse side effects related to its viable nature (Koya, et al. J. Urology 2006, 175:2004-2010) as well as an often low clinical efficacy and duration of response rate, especially in patients who experience treatment relapse (Witjes and Hendricksen. Eur. Urol. 2008, 53:24-26). Its use for the treatment of other cancers is contra-indicated because it contains live mycobacteria, and can give rise to fatal systemic infections (Orifice, et al. Tumori 1978, 64:437-443). Immunotherapy of cancer using intact but inactivated mycobacteria has been attempted using the mycobacterium *Mycobacterium vaccae*, but no definitive long-term survival following its use has so far been identified in clinical studies (see Stanford et al., Eur. J. Cancer 2008, 44:224-227). It is clear that intact mycobacteria, whether viable or inactivated, do not represent the most effective form of immunotherapy for the treatment of cancer.

Immunotherapy utilizing bacterial cell walls and bacterial extracts has been extensively evaluated in animal tumor models, in patients suffering from cancer (U.S. Pat. Nos. 4,503,048, 5,759,554 and 6,326,357), and as treatments for infectious diseases, such as bacterial and viral infections (U.S. Pat. Nos. 3,172,815, and 4,744,984).

Mycobacterial cell wall compositions with immune stimulant and anticancer activity (for example as described in U.S. Pat. Nos. 4,503,048, 5,759,554 and 6,329,347 or in Ribi et al., J. Bacteriol. 1965, 91:975-983) suffer from the disadvantage that biological reagents and materials, chemical reagents, solvents or diluents and enzymatic treatments are required for their preparation, with the potential for noxious chemical and foreign protein contamination. Moreover, it has been reported that in order to obtain optimal anticancer activity with highly purified mycobacterial cell walls (essentially consisting of the cell wall skeleton following extensive chemical and enzymatic treatments) formulation as oil emulsions is required (Yarkoni and Rapp, Cancer Res., 1979 39:535-7). Oil emulsions containing mycobacterial cell walls are often physically unstable and are difficult to prepare reproducibly, and can be toxic to the recipient because of the well-known potential to induce hypersensitivity reactions. Mycobacterial cell walls containing biologically active complexed DNA that possess both immunotherapeutic and anticancer activity and that do not depend on the presence of oil have also been described (U.S. Pat. No. 6,326,357), but these again suffer from the disadvantage that chemical and enzymatic treatments are required for their preparation, with the potential for noxious chemical and foreign protein contamination. In addition, using such compositions it has not proven possible to preferentially optimize either the immunotherapeutic activity or the anticancer activity.

It is recognized by those of ordinary skill in the art that disruption of microorganisms can be achieved using small sample volumes and refrigerated pressure cells (such as the Sorvall pressure cell) at high pressures of between 40,000-45,000 pounds per square inch (PSI, equivalent to 276-317 mPa) (see Ribi et al., J. Bacterial., 1966, 91:975-983). Such processes are time consuming, inefficient, and of low volume, and are additionally hampered by the current unavailability of this type of equipment. More efficient processes that use high pressure homogenization have been described for the isolation of proteins (as inclusion bodies) from genetically engineered microorganisms (see Peternel and Komel: Isolation of biologically active nanomaterial [inclusion bodies] from bacterial cells. Microbial Cell Factories 2010 9:66). It is however recognized by those of skill in the art that Gram-positive organisms are resistant to such processes by virtue of their peptidoglycan content and structure (see Diels and Michaels: High pressure homogenization as a non-thermal technique for the inactivation of microorganisms. Crit. Rev. Microbiol., 2006; 32:201-216). The use of techniques to minimize the number of homogenization cycles is also taught by those skilled in the art (see Bailey et al., Improved homogenization of recombinant *Escherichia coli* following pretreatment with guanidinium chloride: Biotech. Prog., 1995; 11:533-539). The use of such procedures is in fact clearly designed to remove cell wall fragments, not preserve them. The presence of nucleic acids such as DNA using high pressure disruption techniques is additionally taught as a contaminating material to be removed, not preserved (see Rathore et al., Analysis for residual host cell proteins and DNA in process streams of a recombinant protein product expressed in *Escherichia coli* cells: J. Pharm. Biomed. Anal., 2003; 32:1199-1211). What is needed are new procedures for the preparation of new bacterial nucleic acid compositions that use working volumes that are scalable, range from several mL to multi-liter volumes, and result in the efficient production of new bacterial nucleic acid and cell wall compositions.

It is known that mycobacterial cell walls and components thereof can stimulate and activate macrophages, monocytes and dendritic cells to produce bioactive molecules that can initiate, accelerate, amplify and stimulate responsive cells of the immune system such that an immune stimulatory effect is achieved. These bioactive molecules include, but are not limited to, hematopoietic and myeloid growth factors, cytokines and chemokines.

Growth factors are proteins that bind to receptors on a cell surface, with the primary result of activating cellular proliferation and/or differentiation. Cytokines are a unique family of regulatory proteins. Secreted primarily from cells of the immune system such as but not limited to leukocytes and acting as intercellular mediators, cytokines stimulate the humoral and cellular immune response, as well as the activation of phagocytic cells. Cytokines that are secreted from lymphocytes are termed lymphokines, whereas those secreted by monocytes or macrophages are termed monokines. Many of the lymphokines are also known as interleukins (IL), since they are not only secreted by leukocytes but also able to affect the cellular responses of leukocytes. Chemokines are a class of cytokines that have the ability to attract and activate leukocytes, especially in response to infections (a process termed chemotaxis). They can be divided into at least three structural branches: c (chemokines, c), cc (chemokines, cc), and cxc (chemokines, cxc), according to variations in a shared cysteine motif (Johrer et al. Exp. Opin. Biol. Ther. 2008 8:269-290.). The harmful effects of chemotherapeutic agents or radiation therapy on the production of the cells of the immune system that are responsible for producing these hematopoietic and myeloid growth factors, cytokines and chemokines results in increased susceptibility to opportunistic infections.

Cancer (of which there are over 100 diseases) is an aberrant net accumulation of atypical cells, which results from uncontrolled cell division, an insufficiency of or defective apoptosis, or a combination of the two. Mutations in apoptosis-related genes such as, but not limited to, Fas, TNFR1 and p53/p21 have each been implicated in the pathogenesis of cancers (Levine, A. Cell 88:323-331, 1997; Fisher, D. Cell 78:529-542, 1994). Aberrant apoptosis is important not only to the pathogenesis of cancers, but also to a cancer's likelihood of resistance to many anti-cancer therapies.

Resistance to apoptosis induction has emerged as an important category of multiple drug resistance (MDR), one that likely explains a significant proportion of treatment failures. MDR, the simultaneous resistance to structurally and functionally unrelated classes of chemotherapeutic agents, can be both inherent and acquired. That is, some cancers never respond to therapy, whereas other cancers, initially sensitive to therapy, subsequently develop drug resistance through the selection of resistant clones. As chemotherapeutic agents rely primarily on an induction of apoptosis in cancer cells for their therapeutic effect, drug resistance, which diminishes the effectiveness of chemotherapeutic agents, leads directly or indirectly to reduced apoptosis and is generally associated with poor clinical prognosis in a variety of cancers.

Prior art anti-cancer agents have proven to be less than adequate for clinical applications. Many of these agents are inefficient (Bischoff et al. Science 274:373-376, 1996) or toxic, have significant side effects (Lamm et al. Journal of Urology 153:1444-1450, 1995), result in the development of drug resistance or immune sensitization and hypersensitivity reactions, and are debilitating for the recipient.

Therefore, there is a need for novel therapeutic compositions that stimulate responsive cells of the immune system to produce cytokines, chemokines and hematopoietic and myeloid growth factors, inhibit proliferation of cancer cells and induce apoptosis in cancer cells. These therapeutic compositions should be useful as an anti-cancer agent in their own right as well as having an adjuvant activity with respect to other anti-cancer agents. This therapeutic composition should be useful in preventing or treating myelosuppression associated with cancer, surgery, radiation or chemotherapy. Moreover, such a therapeutic composition should be simple and relatively inexpensive to prepare, its activity should be reproducible among preparations, its activity should remain stable over time, and its effects on cancer cells should be achievable with dose regimens that are associated with minimal adverse reactivity and toxicity. In addition, there is a need for methods of manufacturing novel therapeutic compositions that are efficient and that do not result in the presence of enzymes or chemicals used in their preparation.

There is also a need for a novel therapeutic composition that treats, prevents, abates or ameliorates autoimmune disorders, inflammatory or infectious disease, myelosuppression or hematopoietic and myeloid abnormalities. The therapeutic composition should be useful as an adjuvant with other therapeutic agents. Moreover, such a therapeutic composition should be simple and relatively inexpensive to prepare, its activity should be reproducible among preparations, its activity should remain stable over time, and its effects should be achievable with dose regimens that are associated with minimal toxicity.

SUMMARY OF THE INVENTION

The present invention satisfies the above needs by providing novel compositions comprising ribonucleic acid (RNA) and cell walls (defined as RNC herein) which are derived from bacteria or mycobacteria. The present invention satisfies the above needs by providing novel compositions comprising bacterial ribonucleic acid (RNA) and bacterial cell walls (defined as BRNC) and methods of making and using these compositions. The present invention also satisfies the above needs by providing novel compositions comprising mycobacterial RNA and mycobacterial cell walls (defined as MRNC) and methods of making and using these compositions. These novel compositions comprise bacterial or mycobacterial RNA in the form of oligoribonucleotides and polyribonucleotides wherein the RNA can exist as single strands (ss), double strands (ds), or single-double stranded hybrid strands (hs), isolated from bacteria or mycobacteria and bacterial or mycobacterial cell walls, wherein the RNA is formulated in a pharmaceutically acceptable vehicle or complexed (where the term complex is used to describe the chemical association of two or more molecular species) to a pharmaceutically acceptable carrier system. Although pharmaceutical carrier systems known to those of skill in the art can be used, in one embodiment the carrier system is based on bacterial cell walls or mycobacterial cell walls. The compositions of the present invention may also contain intact bacterial or mycobacterial cells, the content of which is selected for the desired therapeutic intent.

The compositions of the present invention possess anti-cancer activity. The compositions of the present invention also contain immune system stimulating activity. The compositions of the present invention also act as adjuvants to other therapeutic modalities.

Three different names are used in the present application to describe these novel compositions. First, the term bacterial RNA composition (BRNC) is used generally to describe the compositions made from different species of bacteria. BRNC may be prepared from different Gram-negative or Gram-positive bacteria with the methods disclosed herein. Second, the term mycobacterial RNA composition (MRNC) is used to describe the compositions made from different mycobacteria. In different embodiments, MRNC may be prepared from any *mycobacterium*. Third, in other embodiments, specific mycobacterial species, mycobacterial complexes or mycobacterial strains are used to prepare MRNC. Examples of but not limited to these are *Mycobacterium avium* (including sub-species *paratuberculosis*, commonly termed MAP), *Mycobacterium bovis* BCG, *Mycobacterium phlei*, *Mycobacterium smegmatis*, or *Mycobacterium vaccae* with the methods disclosed herein. It will be recognized by one of skill in the art that the methods of manufacturing the compositions described herein are applicable to the manufacture of MRNC from mycobacteria other than those described in the detailed description and examples.

The term Mycobacterial RNA composition (MpRNC) is used to describe the compositions comprising RNA and cell walls made from *Mycobacterium phlei*. The terms *Mycobacterium bovis* strain BCG RNA composition (MbRNC), *Mycobacterium smegmatis* RNA composition (MsRNC), *Mycobacterium avium* subspecies *paratuberculosis* (MAP) RNA composition (MapRNC) and *Mycobacterium vaccae* RNA composition (MvRNC) are used to describe the compositions comprising RNA and cell walls made from *Mycobacterium bovis* BCG, *Mycobacterium smegmatis*, *Mycobacterium avium* subspecies *paratuberculosis* and *Mycobacterium vaccae*, respectively. In each composition, MRNC, MpRNC, MbRNC, MsRNC, MapRNC and MvRNC, RNA is isolated from mycobacteria using a procedure that results in an efficient production of oligoribonucleotides and polyribonucleotides.

In another embodiment, each MRNC, MpRNC, MbRNC, MsRNC, MapRNC or MvRNC, may also contain different amounts of intact mycobacterial cells. Intact cells may be present in MRNC, MpRNC, MbRNC, MsRNC, MapRNC or MvRNC in amounts of from approximately 0-99%, 0.05-95%, 0.07-50%, 0.1-20% or 0.19-19% by weight, or in an amount within any of these ranges, or less than 0.75% or less than 0.2% by weight.

In another embodiment, these novel compositions possess an RNA content (which can range from approximately 30% to 100% of the total nucleic acid content) in the form of oligoribonucleotides and polyribonucleotides that are 2 to 4000 bases in length. In another embodiment, these novel compositions possess an oligoribonucleotide and polyribonucleotide content (approximately 30-100% of the total nucleic acid content) in the form of oligoribonucleotides and polyribonucleotides that are 2 to 150 bases in length. In yet another embodiment, these novel compositions possess an oligoribonucleotide and polyribonucleotide content (approximately 30-100% of the total nucleic acid content) in the form of oligoribonucleotides and polyribonucleotides greater than 150, or 151 to 4000 bases in length. In another embodiment, these novel compositions possess an oligoribonucleotide and polyribonucleotide content (approximately 30-100% of the total nucleic acid content) mostly in the form of oligoribonucleotides and polyribonucleotides that are 20 to 40 bases in length.

Anti-cancer activity of the present compositions is maximized when there is minimal content of intact mycobacterial cells. Immune stimulatory activity is maximized when there is a content of intact mycobacterial cells in the range of 5-50% w/w. The desired content of intact mycobacterial, *Mycobacterium phlei*, *Mycobacterium bovis* BCG, *Mycobacterium smegmatis*, *Mycobacterium avium* subspecies *paratuberculosis* or *Mycobacterium vaccae* cells can be achieved by controlling the manufacturing process as detailed in the examples, or by adding intact mycobacterial, *Mycobacterium phlei*, *Mycobacterium bovis* BCG, *Mycobacterium smegmatis*, *Mycobacterium avium* subspecies *paratuberculosis* or *Mycobacterium vaccae* cells to MRNC, MpRNC, MbRNC, MsRNC, MapRNC or MvRNC. MRNC may be used alone as a composition prepared from one mycobacterial species, strain, sub-strain or complex, or in combination with MRNC from other mycobacterial species, strain, sub-strain or complex. For example, a combination of MpRNC and MvRNC will give optimal NOD2 and TLR2 activation for immune stimulation and cytokine induction. Similarly, a combination of MpRNC and MvRNC will give optimal anticancer activity and immune stimulation.

These new compositions possess immune stimulatory, anti-cancer and hematopoietic and myeloid stem cell growth factor stimulating activity. As opposed to prior art preparations, these new compositions contain oligoribonucleotides and polyribonucleotides (such as but not limited to single strands (ss), double strands (ds) or mixtures thereof), and contain levels of intact mycobacteria appropriate for the intended application. Also, as opposed to prior art, where combinations of synthetic agents are required (see Uehara et al., Muramyldipeptide and diaminopimelic acid-containing desmuramylpeptides in combination with chemically synthesized Toll-like receptor agonists synergistically induced production of interleukin-8 in a NOD2- and NOD-dependent manner, respectively, in human monocytic cells in culture: Cell. Microbiol., 2005; 7:53-61), these new compositions have the ability to activate both the nucleotide-binding oligomerization domain 2 (NOD2) and Toll-like receptor 2 (TLR2) receptors, thus demonstrating an unexpected bifunctional agonist activity for immune system receptors that is useful for stimulation of the immune system, stimulating hematopoietic and myeloid stem cell proliferation and in treating cancer in both prophylactic or therapeutic treatment regimens. In different embodiments, these compositions are effective in inducing a response in responsive cells of an animal's immune system, in inducing cell cycle arrest or apoptosis and inhibiting cellular proliferation. These compositions induce responsive cells of the immune system to produce cytokines, chemokines and hematopoietic and myeloid stem cell growth factors.

MRNC, MpRNC, MbRNC, MsRNC, MapRNC and MvRNC are relatively inexpensive to prepare and their activity is reproducible among preparations. MRNC, MpRNC, MbRNC, MsRNC, MapRNC and MvRNC remain stable and effective over time and at dose regimens that are associated with minimal toxicity.

In one embodiment of the invention, MRNC, MpRNC, MbRNC, MsRNC, MapRNC and MvRNC, are prepared from mycobacteria or *Mycobacterium phlei*, *Mycobacterium bovis* BCG, *Mycobacterium smegmatis*, *Mycobacterium avium* subspecies *paratuberculosis* or *Mycobacterium vaccae* respectively, as follows: the mycobacteria are grown and harvested. The mycobacteria are disrupted to remove as required intact mycobacteria via the utilization of high-pressure homogenization followed by a centrifugation process to eliminate as required any residual intact mycobacterial cells. Importantly, use is made of RNase-free and or non-specific nuclease-free reagents to optimize recovery of the RNC.

Low relative centrifugal force is used to remove intact mycobacteria as required. Oligoribonucleotides and polyribonucleotides can then be isolated using conventional extraction techniques, for example guanidinium thiocyanate-phenol-chloroform extraction, or a high relative centrifugal force is applied to the supernatant after removal of intact mycobacteria to isolate oligoribonucleotides and polyribonucleotides that remain formulated with mycobacterial cell walls after cellular disruption. Importantly, reagents that do not contain nuclease contamination (non-specific endo- and exo-nucleases or ribonucleases) are used to eliminate or minimize RNA degradation and thereby optimize yield during the preparation steps.

MRNC, MpRNC, MbRNC, MsRNC, MapRNC and MvRNC are effective therapeutic agents in preventing, treating, lessening the impact of and eliminating a variety of diseases including, but not limited to, malignant, autoimmune and immunodeficiency diseases, myelosuppression and hematopoietic and myeloid abnormalities. MRNC, MpRNC, MbRNC, MsRNC, MapRNC and MvRNC are particularly useful for treating diseases and processes mediated by undesired and uncontrolled cell proliferation, such as cancer. These compositions are also effective as adjuvants to enhance the effectiveness of other anti-cancer agents. Such anti-cancer agents include, but are not limited to, drugs, immune stimulants, antigens, antibodies, vaccines, radiation, chemotherapeutic agents, genetic, biologically engineered and chemically synthesized agents, and agents that target cell death molecules for activation or inactivation, agents that inhibit proliferation of cancer cells, and that induce apoptosis in cancer cells. MRNC, MpRNC, MbRNC, MsRNC, MapRNC and MvRNC are also effective for the prevention or treatment of myelosuppression (monocytopenia and or neutropenia) associated with the treatment of cancer or cancer by itself, and for the prevention or treatment of diverse hematopoietic and myeloid abnormalities associated with medications or diseases, such as, but not limited to the acquired immunodeficiency syndrome (AIDS), myelodysplastic syndromes, autoimmune diseases, end-stage renal diseases or viral infections.

MRNC, MpRNC, MbRNC, MsRNC, MapRNC or MvRNC, in a pharmaceutically acceptable carrier, may be administered to an animal or human in a dosage effective to stimulate a response in responsive cells of the immune system, and to inhibit proliferation of and induce apoptosis in responsive cells. MRNC, MpRNC, MbRNC, MsRNC, MapRNC or MvRNC can be administered by methods including, but not limited to, suspension in aqueous formulations, in creams and gels, by emulsification in oil or other hydrophobic liquid formulations, enclosure in liposomes, and complexation with natural or artificial carriers, with tissue- or cell-specific ligands or with tissue- or cell-specific antibodies.

In one embodiment, the present invention provides novel compositions comprising, BRNC, MRNC, MpRNC, MbRNC, MsRNC, MapRNC or MvRNC, and methods of making these compositions.

In another embodiment, the present invention provides novel manufacturing procedures for the preparation of BRNC, MRNC, MpRNC, MbRNC, MsRNC, MapRNC or MvRNC compositions that optimize the content of carbon, nitrogen and iron sources in the cultivation media for the manufacture of mycobacterial cell mass.

In another embodiment, the present invention provides novel synthetic media useful for growing mycobacterial cell mass.

In yet another embodiment, the present invention provides novel manufacturing procedures for the preparation of BRNC, MRNC, MpRNC, MbRNC, MsRNC, MapRNC or MvRNC compositions that optimize the content of carbon, nitrogen and iron in the cultivation media and that eliminate the requirement for exogenous biological materials for the manufacture of mycobacterial cell mass, and that eliminate the use exogenous biological or chemical agents during the down-stream manufacturing procedure.

In still another embodiment, the present invention provides novel therapeutic BRNC, MRNC, MpRNC, MbRNC, MsRNC, MapRNC or MvRNC, in a pharmaceutically acceptable carrier.

In a further embodiment, the present invention provides therapeutic compositions comprising BRNC, MRNC, MpRNC, MbRNC, MsRNC, MapRNC or MvRNC, and methods of using these therapeutic compositions to induce a therapeutic response in responsive cells of an animal or a human.

In another embodiment, the present invention provides a method to stimulate responsive cells of the immune system by administering these therapeutic compositions to an animal or a human.

In yet another embodiment, the present invention provides a method to stimulate responsive cells of the immune system to produce bioactive molecules such as cytokines, chemokines, interleukins and/or hematopoietic and myeloid growth factors by administering these therapeutic compositions to an animal or a human.

In a further embodiment, the present invention provides a method that is effective to treat a disease in an animal or human by administering these therapeutic compositions to an animal or a human.

In still another embodiment, the present invention provides a method that is effective to treat cancer in an animal or human by administering these therapeutic compositions to an animal or a human.

In another embodiment, the present invention provides a composition and method that inhibits proliferation of responsive cells of an animal.

In another embodiment, the present invention provides a composition and method that induces apoptosis in responsive cells of an animal.

In yet another embodiment, the present invention provides composition and method that is effective as an adjuvant to other anti-cancer therapies.

In still another embodiment, the present invention provides a composition and method that is effective as an adjuvant to other immune stimulatory therapies.

In a further embodiment, the present invention provides a composition and method that is effective for the treatment of immunodeficiency diseases.

In yet another embodiment, the present invention provides a composition and method that is effective for the prevention or treatment of myelosuppression (leucopenia, neutropenia, thrombocytopenia or anemia) or hematopoietic and myeloid abnormalities.

In still another embodiment, the present invention provides a composition and method that is effective as an adjuvant to other therapies for the prevention or treatment of myelosuppression or hematopoietic and myeloid abnormalities.

In another embodiment, the present invention provides a method that is effective to treat an autoimmune disease in an animal or human by administering these therapeutic compositions to an animal or a human.

In yet another embodiment, the present invention provides a method of manufacturing that does not result in the presence of chemicals or enzymes in the composition.

These and other objects, features and advantages of the present invention will become apparent after a review of the following detailed description of the disclosed embodiment and the appended claims.

BRIEF DESCRIPTION OF THE DRAWINGS

FIGS. 1A-F. Transmission electron micrographs (TEM) of *Mycobacterium phlei* (FIG. 1A), MCWE (FIG. 1B), MCC (FIG. 1C), MpRNC Low (FIG. 1D), MpRNC Intermediate (FIG. 1E) and MpRNC High (FIG. 1F). The bars are 1 μm for FIG. 1A, FIG. 1B and FIG. 1C, and 2 μm for FIG. 1D, FIG. 1E and FIG. 1F.

FIGS. 2A-B. Electrophoretic analysis of nucleic acid oligonucleotide length. FIG. 2A. RNA ladder standard and MpRNC Intermediate prior to autoclaving using the RNA nano 6000 kit. FIG. 2B. MpRNC containing varying proportions of autoclaved *M. phlei* cells (MpRNC High-, MpRNC Low- or and MpRNC Intermediate-) following autoclaving using the small RNA kit (The peak at 4 nucleotides is the internal oligonucleotide standard and is not associated with nucleic acids in the MpRNC. FU=fluorescence units, nt=nucleotide length.

FIGS. 3A-D. RNA and DNA content of MpRNC containing varying proportions of intact autoclaved *M. phlei* cells (FIG. 3A High, FIG. 3B Intermediate, or FIG. 3C Low) and autoclaved *Mycobacterium phlei* (FIG. 3D) as determined before and after RNase-A treatment.

FIGS. 4A-B. RNase-susceptible nucleic acid (NA) in MpRNC, MbRNC, MsRNC and MvRNC. FIG. 4A: Urea-PAGE gel electrophoresis of extracted control-treated and RNase-treated nucleic acids; FIG. 4B: The proportion of RNA in the extracted nucleic acids as determined by scanning densitometry.

FIGS. 5A-B. Mycolic acid profile of MpRNC Intermediate. FIG. 5A: Mycolic acid profile using behenic acid standard for quantification of extractable lipids; FIG. 5B: Mycolic acid profile using low and high mycolic acid carbon number standards (estimated to be ~C40 and ~C110) for quantification of saponifiable lipids.

FIGS. 8A-B. Stimulation of IL-10 and IL-12 production in human peripheral blood mononuclear cells (PBMC) by MpRNC Intermediate containing varying proportions of intact autoclaved *Mycobacterium. phlei*. IL-10 (FIG. 8A) and IL-12p40 (FIG. 8B) subunit production by human PBMC following treatment with MpRNC and autoclaved *Mycobacterium phlei* was determined by ELISA.

DETAILED DESCRIPTION OF THE INVENTION

Figure 2B:
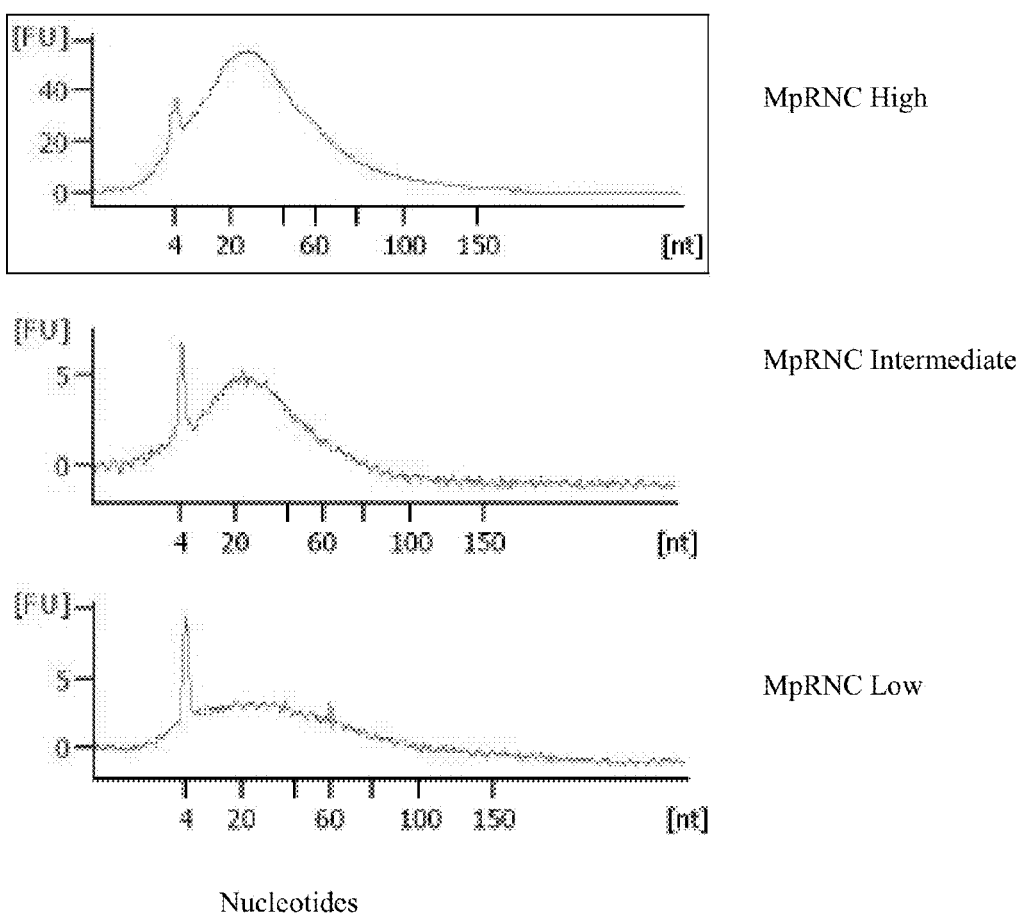

The present invention provides novel compositions comprising ribonucleic acid (RNA) and cell walls (defined as RNC herein) which are derived from bacteria or mycobacteria. The present invention provides novel compositions comprising bacterial RNA and bacterial cell walls (defined as BRNC) and methods of making and using these compositions. The present invention also provides novel compositions comprising mycobacterial RNA and mycobacterial cell walls (defined as MRNC) and methods of making and using these compositions. These compositions can be formulated with carriers, and/or cells. These novel compositions comprise cell walls from bacteria or mycobacteria and RNA in the form of oligoribonucleotides and polyribonucleotides from bacterial or mycobacterial RNA wherein the oligoribonucleotides and polyribonucleotides can exist as single strands (ss), double strands (ds), or single-double stranded hybrid strands (hs). These compositions can be formulated in a pharmaceutically acceptable vehicle or complexed (where the term complex is used to describe the chemical association of 2 or more molecular species) to a pharmaceutically acceptable carrier system. The compositions of the present invention may also contain intact bacterial or mycobacterial cells, the content of which is optimized for the desired therapeutic intent.

These new compositions possess immune stimulatory, anti-cancer and hematopoietic and myeloid stem cell growth factor stimulating activity. As opposed to prior art preparations, these new compositions contain oligoribonucleotides and polyribonucleotides (such as but not limited to single strands (ss), double strands (ds) or mixtures thereof), and optionally contain selected levels of intact mycobacteria appropriate for the intended application. Also, as opposed to prior art, where combinations of synthetic agents are required (see Uehara et al., Muramyldipeptide and diaminopimelic acid-containing desmuramylpeptides in combination with chemically synthesized Toll-like receptor agonists synergistically induced production of interleukin-8 in a NOD2- and NOD-dependent manner, respectively, in human monocytic cells in culture: Cell. Microbiol., 2005; 7:53-61), these new compositions have the ability to activate both the nucleotide-binding oligomerization domain 2 (NOD2) and Toll-like receptor 2 (TLR2) receptors, thus demonstrating an unexpected bifunctional agonist activity for immune system receptors that is useful for stimulation of the immune system, stimulating hematopoietic and myeloid stem cell proliferation and in treating cancer in both prophylactic or therapeutic treatment regimens. In different embodiments, these compositions are effective in inducing a response in responsive cells of an animal's immune system, in inducing cell cycle arrest or apoptosis and inhibiting cellular proliferation. These compositions induce responsive cells of the immune system to produce cytokines, chemokines and hematopoietic and myeloid stem cell growth factors.

MRNC, MpRNC, MbRNC, MsRNC, MapRNC and MvRNC are effective therapeutic agents in preventing, treating, lessening the impact of and eliminating a variety of diseases including, but not limited to, malignant, autoimmune and immunodeficiency diseases, myelosuppression and hematopoietic and myeloid abnormalities. MRNC, MpRNC, MbRNC, MsRNC, MapRNC and MvRNC are particularly useful for treating diseases and processes mediated by undesired and uncontrolled cell proliferation, such as cancer. These compositions are also effective as adjuvants to enhance the effectiveness of other anti-cancer agents. Such anti-cancer agents include, but are not limited to, drugs, immune stimulants, antigens, antibodies, vaccines, radiation, chemotherapeutic agents, genetic, biologically engineered and chemically synthesized agents, and agents that target cell death molecules for activation or inactivation, agents that inhibit proliferation of cancer cells, and that induce apoptosis in cancer cells. MRNC, MpRNC, MbRNC, MsRNC, MapRNC and MvRNC are also effective for the prevention or treatment of myelosuppression (monocytopenia and or neutropenia) associated with the treatment of cancer or cancer by itself, and for the prevention or treatment of diverse hematopoietic and myeloid abnormalities associated with medications or diseases, such as, but not limited to the acquired immunodeficiency syndrome (AIDS), myelodysplastic syndromes, autoimmune diseases, end-stage renal diseases or viral infections.

MRNC, MpRNC, MbRNC, MsRNC, MapRNC or MvRNC, in a pharmaceutically acceptable carrier, may be administered to an animal or human in a dosage effective to stimulate a response in responsive cells of the immune system, and to inhibit proliferation of and induce apoptosis in responsive cells. MRNC, MpRNC, MbRNC, MsRNC, MapRNC or MvRNC can be administered by methods including, but not limited to, suspension in aqueous formulations, in creams and gels, by emulsification in oil or other hydrophobic liquid formulations, enclosure in liposomes, and complexation with natural or artificial carriers, with tissue- or cell-specific ligands or with tissue- or cell-specific antibodies.

Definitions

The term optimization of the manufacturing processes is used to describe the process whereby fermentation to obtain mycobacterial cell mass utilizes a cultivation medium where there is an appropriate carbon, nitrogen and iron content resulting in improved yields of mycobacterial cell mass.

The term optimization of the manufacturing process also refers to the elimination of the requirement for the use of chemicals or enzymes in the manufacture of the mycobacterial cell wall compositions.

Three different names are used in the present application to describe these novel compositions. First, the term bacterial RNA composition (BRNC) is used generally to describe the compositions made from different species of bacteria. BRNC may be prepared from different Gram-negative or Gram-positive bacteria with the methods disclosed herein. Second, the term mycobacterial RNA composition (MRNC) is used to describe the compositions made from different mycobacteria. In different embodiments, MRNC may be prepared from any *mycobacterium*. Third, in other embodiments, specific mycobacterial species, mycobacterial complexes or mycobacterial strains are used to prepare MRNC. Examples of but not limited to these are *Mycobacterium avium* (including sub-species *paratuberculosis*, commonly termed MAP), *Mycobacterium bovis* BCG, *Mycobacterium phlei, Mycobacterium smegmatis*, or *Mycobacterium vaccae* with the methods disclosed herein. It will be recognized by one of skill in the art that the methods of manufacturing the compositions described herein are applicable to the manufacture of MRNC from mycobacteria other than those described in the detailed description and examples.

The term *Mycobacterium* RNA composition (MpRNC) is used to describe the compositions comprising RNA and cell walls made from *Mycobacterium phlei*. The terms *Mycobacterium bovis* strain BCG RNA composition (MbRNC), *Mycobacterium smegmatis* RNA composition (MsRNC), *Mycobacterium avium* subspecies *paratuberculosis* (MAP) RNA composition (MapRNC) and *Mycobacterium vaccae* RNA composition (MvRNC) are used to describe the compositions comprising RNA and cell walls made from *Mycobacterium bovis* BCG, *Mycobacterium smegmatis, Mycobacterium avium* subspecies *paratuberculosis* and *Mycobacterium vaccae*, respectively. In each composition, MRNC, MpRNC, MbRNC, MsRNC, MapRNC and MvRNC, RNA is isolated from mycobacteria using a procedure that results in an efficient production of oligoribonucleotides and polyribonucleotides.

The term mycobacterial RNA composition (MRNC) is used to describe the compositions made from different mycobacteria. In different embodiments, MRNC may be prepared from any *mycobacterium*. In other embodiments, specific mycobacterial species, mycobacterial complexes or mycobacterial strains are used to prepare MRNC. Examples of but not limited to these are *Mycobacterium avium* (including sub-species *paratuberculosis*, commonly termed MAP), *Mycobacterium bovis* BCG, *Mycobacterium phlei, Mycobacterium smegmatis*, or *Mycobacterium vaccae* with the methods disclosed herein. It will be recognized by one of skill in the art that the methods of manufacturing the compositions described herein are applicable to the manufacture of cell wall compositions from mycobacteria other than those described in the detailed description and examples.

The term *Mycobacterium phlei* RNA composition (MpRNC) is used to describe the compositions made from *Mycobacterium phlei*. The terms *Mycobacterium bovis* strain BCG RNA composition (MbRNC), *Mycobacterium smegmatis* RNA composition (MsRNC), *Mycobacterium avium* subspecies *paratuberculosis* (MAP) RNA composition (MapRNC) and *Mycobacterium vaccae* RNA composition (MvRNC) are used to describe the compositions made from *Mycobacterium bovis* BCG, *Mycobacterium smegmatis, Mycobacterium avium* subspecies *paratuberculosis* and *Mycobacterium vaccae*, respectively. In each composition, MRNC, MpRNC, MbRNC, MsRNC, MapRNC and MvRNC, RNA is isolated from mycobacteria using a procedure that results in an efficient production of oligoribonucleotides and polyribonucleotides.

As defined herein, Mycobacterial Culture Media Compositions (MCMC) refer to novel synthetic cultivation media containing optimized carbon, nitrogen and iron sources that are used to prepare mycobacterial cell mass and where the carbon, nitrogen and iron content of the media are such that there is optimal utilization of the carbon and optimal mycobacterial wet cell mass yield.

As defined herein, cultivation refers to the process of generating mycobacterial cell mass wherein the mycobacteria are cultivated in a medium optimized but not limited to the carbon, nitrogen and iron content that ensures optimal division of the bacteria or mycobacteria. Use may be made of equipment and cultivation conditions known to those of skill in the art.

As defined herein, down-stream processing or manufacturing refers to the process of taking mycobacterial cell mass prepared by cultivation, and manufacturing RNA-containing compositions or RNA-containing cell wall compositions by the use of appropriate combinations of high-pressure homogenization, differential centrifugation and heat treatment. Use may be made of techniques known to those skilled in the art that are comparable in effect to high-pressure homogenization without departing from the scope or teachings of the invention.

As defined herein, bacterial cell wall refers to a cell wall from a member of the bacterial kingdom that contains cell wall molecular components, and where at a minimum these molecules comprise polysaccharides and alanine (ALA)-containing peptide chains, commonly called peptidoglycan.

As defined herein, mycobacterial cell wall refers to any cell wall composition prepared from a member of the family mycobacteriaceae and genus *mycobacterium* that contains at a minimum peptidoglycan and mycolic acids, and where the peptidoglycan is composed of a polymer consisting of repeat units of [N-acetylglucosamine-N-acylmuramic acid]$_n$, where N-acyl is either N-acetyl or N-glycolyl, and where the polymeric chains are linked by peptide bridges, and where the mycolic acids are α-substituted β-hydroxylated very-long-chain fatty acids. The exact amino acid composition of these peptide bridges are highly conserved between different mycobacterial species and their strains, and is known to those skilled in the art, but often includes diaminopimelic acid (DAP) and, as far as is known, always includes alanine (ALA) linked to N-acylmuramic acid through the lactic acid moiety. The types of mycolic acid are specific to individual mycobacterial species, and are subdivided into clusters depending on the length of the molecule (range ~60-90 carbon atoms).

As defined herein, exogenous contamination refers to the presence of any exogenous materials, including but not limited to proteins, biochemicals, or chemicals, that are conventionally used in the manufacturing of bacterial- or mycobacterial-derived compositions (including the preparation of bacterial or mycobacterial cell biomass and bacterial or mycobacterial cell wall compositions). In contrast to previous methods of making bacterial and mycobacterial cell wall compositions, the bacterial and mycobacterial proteins associated with the RNC compositions made with the present methods are preserved due to the absence of exogenous proteolytic enzyme treatments. In contrast to previous methods of making bacterial and mycobacterial cell wall compositions, the bacterial and mycobacterial cell wall lipids are preserved due to the absence of exogenous delipidating solvent treatments.

As defined herein, the term manufacture refers to the process whereby an RNC is isolated, in which intact bacterial or mycobacterial cells are disrupted to form cell wall fragments, and where such fragments are then isolated in combination with RNA to give a bacterial or mycobacterial cell wall RNC.

As defined herein, the terms oligoribonucleotides and polyribonucleotides refer, respectively, to RNA molecules, of 2 to approximately 20 bases or of 20 to approximately 4000 bases in length obtained from bacteria, mycobacteria, *Mycobacterium phlei, Mycobacterium bovis* strain BCG, *Mycobacterium smegmatis, Mycobacterium avium* subspecies *paratuberculosis* or *Mycobacterium vaccae*. The RNA together with bacterial or mycobacterial cell walls is defined as RNC. The RNA may be composed of single strands (ss), double strands (ds), single-double stranded hybrid strands (hs), and the RNA is obtained from bacteria, more preferably from mycobacteria and most preferably from *Mycobacterium phlei, Mycobacterium bovis* BCG, *Mycobacterium smegmatis, Mycobacterium avium* subspecies *paratuberculosis* or *Mycobacterium vaccae*. The RNC may comprise one or more RNC from different bacteria or mycobacteria, and may additionally comprise intact cells from different bacteria or mycobacteria. RNC can also be formulated using cell walls from one or more bacteria or mycobacteria.

As defined herein, high-pressure homogenization of bacteria or mycobacteria refers to a process whereby a suspension of intact bacteria or mycobacteria in an aqueous excipient are passed under pressure through a minute gap in a valve creating conditions of high turbulence and shear force, which cause the disintegration of the bacteria or mycobacteria into cell wall fragments and the release of cytoplasmic components, including protein and lipid.

As defined herein, low-speed centrifugation refers to a relative centrifugal force (RCF) sufficient to sediment undisrupted bacteria or mycobacteria.

As defined herein, high-speed centrifugation refers to a relative centrifugal force sufficient to sediment bacterial or mycobacterial cell wall RNC.

As defined herein, immune stimulation refers to the stimulation of the innate and or acquired immune system, such that an immune response is elicited. This immune response may be comprised of but not limited to one or more of the following: immune cell differentiation and division, activation of Toll-like receptors, activation of NOD receptors, activation of receptors other than Toll-like or NOD, induction of chemokine and cytokine synthesis, induction of growth factor synthesis, increased expression of cell surface markers, decreased expression of cell surface markers, activation of cytocidal or cytotoxic activity, stimulation of antibody production or stimulation of cell-mediated immunity.

As defined herein, anticancer activity refers to any process that results in the inhibition of and or death of cancer cells. Such anticancer activity may be the result of a direct effect on cancer cell targets, or the result of an indirect effect due to stimulation of the immune system.

The term animal includes human in this application.

The term produce means synthesize and/or release in this application.

Novel Compositions for the Cultivation of Mycobacteria

The present invention provides novel media for cultivating mycobacteria that contain optimized levels and ratios of carbon, nitrogen and iron for the generation of mycobacterial cell mass in a timely manner. These novel media utilize organic nitrogen sources or inorganic nitrogen sources, and provide for procedures where additional carbon, nitrogen and iron may be provided within one molecule. These novel cultivation media do not require the addition of exogenous proteins such as bovine albumin or catalase for the efficient production of mycobacterial cell mass.

In one embodiment, the optimized nitrogen is provided by the addition of inorganic ammonium salts including but not limited to ammonium sulfate. The optimized carbon is provided by the addition of organic molecules including but not limited to sugars such as glucose (dextrose), glycols such as glycerol or acids such as citric acid, and that contain carbon that can be metabolized by the mycobacteria.

In another embodiment, the optimized nitrogen and carbon are provided by molecules containing both atoms including but not limited to ammonium citrate (dibasic) or amino acids such as but not limited to asparagine.

In yet another embodiment the optimized carbon, nitrogen and iron are provided by molecules containing all three atoms including but not limited to ferric ammonium citrate.

In a further embodiment, use may be made of cultivation media that provide optimized carbon, nitrogen and iron as well as additional divalent cations including but not limited to calcium and magnesium.

In yet another embodiment, the cultivation media are formulated without additional exogenous biological agents including but not limited to albumins, enzymes or growth enhancing materials including but not limited to mycobactin.

In yet another embodiment, use is made of mixing and aeration procedures to optimize access to oxygen to ensure rapid aerobic growth of the bacteria or mycobacteria Novel Bacterial and Mycobacterial Compositions The present invention provides novel bacterial and mycobacterial compositions comprise RNA isolated from bacteria or mycobacteria, a bacterial or mycobacterial cell wall. These compositions include BRNC, MRNC, MpRNC, MbRNC, MsRNC, MapRNC and MvRNC, as previously defined. These compositions optionally contain different amounts of intact bacterial or mycobacterial cells. In another embodiment, each composition, MRNC, MpRNC, MbRNC, MsRNC, MapRNC or MvRNC, may also contain different amounts of intact mycobacterial, *Mycobacterium phlei*, *Mycobacterium bovis* BCG, *Mycobacterium smegmatis*, *Mycobacterium avium* subspecies *paratuberculosis*, or *Mycobacterium vaccae* cells. Intact cells may be present in MRNC, MpRNC, MbRNC MsRNC, MapRNC or MvRNC in amounts of from 0-99%, 0.05-95%, 0.07-50%, 0.1-20% or 0.19-19% by weight, or in an amount within any of these ranges.

In another embodiment, these novel compositions possess an RNA composition content (which can range from approximately 30% to 100% of the total nucleic acid content) in the form of oligoribonucleotides and polyribonucleotides of between 2 and 4000) bases in length. In yet another embodiment, these novel compositions possess an RNA content (30-100% of the total nucleic acid content) in the form of oligoribonucleotides and polyribonucleotides that are greater than 150 bases, or of between 151 to 4000 bases in length. In another embodiment, these novel compositions possess an RNA content (30-100% of the total nucleic acid content) that is mostly in the form of oligoribonucleotides and polyribonucleotides that are between 20 and 40 bases in length.

In one embodiment, novel RNC compositions containing about 90% or more RNA in the form of oligoribonucleotides and polyribonucleotides are prepared by extraction of RNA from mycobacteria, *Mycobacterium phlei*, *Mycobacterium bovis* BCG, *Mycobacterium smegmatis*, *Mycobacterium avium* subspecies *paratuberculosis* (MAP) or *Mycobacterium vaccae*, using for example guanidinium thiocyanate-phenol-chloroform extraction. Such RNA preparations may be heat-treated (by for example but not limited to 121° C. for between 5-30 min) in order to give an RNC composition where the oligoribonucleotides and polyribonucleotides chain length is between 2 and 4000 bases. This RNC composition may be combined with a pharmaceutically acceptable carrier.

Anti-cancer activity is optimized when there is minimal content of intact mycobacterial cells. Immune stimulatory activity is optimized when there is a content of intact mycobacterial cells in the range of 5-50% w/w. The number of intact bacterial, mycobacterial, *Mycobacterium phlei*, *Mycobacterium bovis* BCG, *Mycobacterium smegmatis*, *Mycobacterium avium* subspecies *paratuberculosis* (MAP) or *Mycobacterium vaccae* cells can be modulated by controlling the manufacturing process as detailed in the examples, or by adding intact mycobacterial, *Mycobacterium phlei*, *Mycobacterium bovis* BCG, *Mycobacterium smegmatis*, *Mycobacterium avium* subspecies *paratuberculosis* (MAP) or *Mycobacterium vaccae* cells to MRNC, MpRNC, MbRNC, MsRNC, MapRNC, or MvRNC.

These novel compositions, MRNC, MpRNC, MbRNC, MsRNC, MapRNC, or MvRNC, possess immune stimulating, anti-cancer and hematopoietic and myeloid cell growth factor stimulating activity. As opposed to prior art preparations, these new compositions contain single, single strands (ss), double strands (ds) and single-double stranded hybrid strands (hs), are optimized for immune stimulatory and anti-cancer activity, and are formulated with mycobacterial, *Mycobacterium phlei*, *Mycobacterium bovis* BCG, *Mycobacterium smegmatis*, *Mycobacterium avium* subspecies *paratuberculosis* (MAP) or *Mycobacterium vaccae* cell walls. In one embodiment these compositions further comprise levels of intact mycobacterial cells appropriate for the intended application.

The compositions of the present invention are effective in stimulating the immune system, in stimulating hematopoietic and myeloid growth factor synthesis, and in treating cancer. In different embodiments, these compositions are effective in inducing a response in responsive cells of an animal's immune system, in inducing cell cycle arrest or apoptosis and inhibiting cellular proliferation. These compositions induce responsive cells of the immune system to produce cytokines, chemokines and hematopoietic and myeloid growth factors.

The compositions of the present invention are effective in stimulating the immune system and in treating cancer when combined with a pharmaceutically acceptable carrier to form a therapeutic composition and administered to an animal. In different embodiments, these therapeutic compositions induce a response in responsive cells of an animal's immune system, induce cell cycle arrest or apoptosis and inhibit cancer cell proliferation. These compositions induce responsive cells of the immune system to produce cytokines, chemokines and hematopoietic and myeloid cell growth factors.

MRNC, MpRNC, MbRNC, MsRNC, MapRNC and MvRNC are effective therapeutic agents in preventing, treating, lessening and eliminating a variety of diseases including, but not limited to, malignant, autoimmune and immunodeficiency diseases, myelosuppression and hematopoietic and myeloid abnormalities. MRNC, MpRNC, MbRNC, MsRNC, MapRNC and MvRNC are particularly useful for treating diseases and processes mediated by undesired and uncontrolled cell proliferation, such as but not limited to cancer. These compositions are also effective as adjuvants to enhance the effectiveness of other anti-cancer agents. Such anti-cancer agents include, but are not limited to, drugs, immune function stimulants, immune function inhibitors, antigens, antibodies, vaccines, radiation, chemotherapeutic agents (either alone or in appropriate combinations known to those of skill in the art), genetic, biologically engineered and chemically synthesized agents, and agents that target cell death molecules for activation or inactivation, agents that inhibit proliferation of cancer cells, and that induce apoptosis in cancer cells. MRNC, MpRNC, MbRNC, MsRNC, MapRNC and MvRNC are also effective for the prevention or treatment of myelosuppression (leucopenia, neutropenia,) associated with the treatment of cancer or induced by the cancer itself, and for the prevention or treatment of diverse hematopoietic and myeloid abnormalities associated with medications or diseases, such as, but not limited to the acquired immunodeficiency syndrome (AIDS), myelodysplastic syndromes, autoimmune diseases, end-stage renal diseases or viral infections. Combinations of two or more compositions of the present invention may be used to optimize modulation of the immune system and to treat cancer. For example, a combination of MpRNC and MvRNC will give optimal NOD2 and TLR2 activation for immune stimulation and cytokine induction. Similarly, a combination of MpRNC and MvRNC will give optimal anticancer activity and immune stimulation.

In one embodiment, bacteria may be used to provide a BRNC composition that comprises bacterial RNA in the form of oligoribonucleotides and polyribonucleotides, bacterial cell walls, and a pharmaceutical carrier, excipient or vehicle. In another embodiment mycobacteria may be used to provide an MRNC composition comprising mycobacterial RNA in the form of oligoribonucleotides and polyribonucleotides, mycobacterial cell walls, and a pharmaceutical carrier or vehicle. In another embodiment the MpRNC, MbRNC, MsRNC, MapRNC or MvRNC compositions comprise *Mycobacterium phlei* RNA, *Mycobacterium bovis* BCG RNA, *Mycobacterium smegmatis* RNA, *Mycobacterium avium* subspecies *paratuberculosis* RNA or *Mycobacterium vaccae* RNA respectively, in the form of oligoribonucleotides and polyribonucleotides, in combination with cell walls from these species, and a pharmaceutical carrier, excipient or vehicle.

In one embodiment the BRNC, MRNC, MpRNC MbRNC, MsRNC or MvRNC compositions are formulated with a pharmaceutical delivery system such as but not limited to chitosan nanoparticles or cationic liposomes.

Each of these compositions, BRNC, MRNAC, MpRNC, MbRNC, MsRNC, MapRNC and MvRNC may be combined with an acceptable carrier, such as a pharmaceutically acceptable carrier, excipient, vehicle or other delivery system known to those of skill in the art to form a composition that may be administered to an animal or a human. Each of these compositions, BRNC, MRNC, MpRNC, MbRNC, MsRNC, MapRNC and MvRNC may be combined with selected amounts of intact bacterial cells, mycobacterial cells, *Mycobacterium phlei*, *Mycobacterium bovis* BCG, *Mycobacterium smegmatis*, *Mycobacterium avium* subspecies *paratuberculosis* or *Mycobacterium vaccae* cells, respectively, to form a composition that may be administered to an animal or a human.

BRNC, MRNAC, MpRNC, MbRNC, MsRNC, MapRNC and MvRNC are effective in inducing responsive cells of the immune system to produce cytokines, chemokines and hematopoietic and myeloid growth factors, and in inhibiting proliferation of and inducing apoptosis in responsive cells including, but not limited to, cancer cells, in an animal.

Eubacterial species can be used to practice the present invention including, but not limited to, *Coryneform* species, *Corynebacterium* species, *Rhodococcus* species, *Bordetella* species, *Escherichia* species, *Listeria* species, *Nocardia* species and Mycobacterial species to make BRNC or MRNC. Mycobacterial species including, but not limited to, *Mycobacterium smegmatis, Mycobacterium fortuitum, Mycobacterium kansaii, Mycobacterium tuberculosis, Mycobacterium bovis, Mycobacterium vaccae, Mycobacterium avium* and associated subspecies and *Mycobacterium phlei* can be used to make MRNC. In yet another embodiment, the *mycobacterium* species *Mycobacterium phlei, Mycobacterium bovis* BCG, *Mycobacterium smegmatis, Mycobacterium avium* subsp. *paratuberculosis* or *Mycobacterium vaccae* are used to make MpRNC, MbRNC, MsRNC, MapRNC or MvRNC. In yet another embodiment Archaebacterial species can be used to prepare BRNC.

Method for Manufacturing Mycobacterial Cell Wall RNA Containing Compositions (MRNC)

The present invention additionally provides a method for manufacturing mycobacterial cell wall RNA compositions from any mycobacterial species. Comprehensive listings of mycobacterial species, mycobacterial complexes, mycobacterial sub-species and mycobacterial strains that can be used to prepare mycobacterial cell wall-RNA using the method of the present invention are maintained by and readily available from for example the NCBI of the USA. Although the present invention provides methods for the manufacture of MRNC from all mycobacterial species and strains, preferred mycobacterial species and strains are those that are known to be fast-growing in culture, and thus capable of providing mycobacterial cell biomass in short periods of time. Also preferred are those mycobacterial species and strains that are known to be fast-growing and are additionally non-pathogenic to immunocompetent individuals.

BRNC, MRNC, MpRNC, MbRNC, MsRNC, MapRNC and MvRNC are relatively inexpensive to prepare, their activity is reproducible among preparations and remains stable over time, and they are not contaminated by exogenous materials, including but not limited to proteins, enzymes, biochemicals r chemicals used by those of ordinary skill in the art to prepare mycobacterial cell wall compositions. Further, the BRNC, MRNC, MpRNC, MbRNC, MsRNC, MapRNC and MvRNC preparations are minimally, if at all, toxic to the recipient To prepare BRNC, MRNC, MpRNC, MbRNC, MsRNC, MapRNC and MvRNC, bacterial species, mycobacterial species, *Mycobacterium phlei, Mycobacterium bovis* BCG, *Mycobacterium smegmatis, Mycobacterium avium* subspecies *paratuberculosis* or *Mycobacterium vaccae* respectively, are grown in appropriate liquid media with an optimized carbon, nitrogen and iron content that assures complete utilization of carbon sources, and are harvested. Amino acids provide a source of nitrogen. Dibasic amino acids including but not limited to asparagine are preferred sources of nitrogen. Other sources of nitrogen include ammonium salts or their equivalent. Additional sources of iron are inorganic salts, or organic salts, including but not limited to citrate, that provide additional sources of carbon. Iron complexes, including but not limited to ferric ammonium citrate (ammonium ferric citrate), provide additional iron, nitrogen and carbon sources. Preferred concentrations of carbon (as glucose or other metabolically available carbon source) are 500-2500 mMol/liter. In different embodiments, ratios of C to N are from about 1:0.0095 to 1:0.06, from about 1:0.02 to 1:0.06, or at or about 1:0.06. In different embodiments, ratios of C to Fe are at or about $1:1.8\times10^{-4}$ to $1:3.2\times10^{-3}$; at or about $1:1.8\times10^{-3}$ to $2.7\times10^{-4}$; or at or about $1:2.7\times10^{-4}$. Utilization may be made of any acceptable source of carbon, nitrogen or iron known to those of skill in the art. Such media may also contain additional salts as well as vitamins, and it is to be expected that the presence and concentrations of these will be adjusted according to the particular needs.

The bacteria or mycobacteria are disrupted to liberate RNA and to ensure the controlled removal of intact bacteria, mycobacteria, *Mycobacterium phlei, Mycobacterium bovis* BCG, *Mycobacterium smegmatis, Mycobacterium avium* subspecies *paratuberculosis* or *Mycobacterium vaccae* cells. Disruption occurs via the use of a high-pressure homogenization process followed by a centrifugation process. Low relative centrifugal force removes intact bacteria or mycobacteria. RNA from BRNC, MRNC, MpRNC, MbRNC, MsRNC, MapRNC and MvRNC may be extracted at this stage using guanidinium thiocyanate-phenol-chloroform or similar procedures known to those of skill in the art. Alternatively, high relative centrifugal forces can be used to isolate BRNC, MRNC, MpRNC, MbRNC, MsRNC, MapRNC and MvRNC formulated with bacterial, mycobacterial, *Mycobacterium phlei, Mycobacterium bovis* BCG, *Mycobacterium smegmatis, Mycobacterium avium* subspecies *paratuberculosis* or *Mycobacterium vaccae* cell walls after bacterial or mycobacterial cellular disruption. Importantly, nuclease-, and DNase/RNase-free (both endo- and exo-nuclease activity) reagents are used and the process is carried out at or about 4° C. to minimize RNA degradation during the preparation steps.

The oligoribonucleotide and polyribonucleotide sequences, oligoribonucleotide and polyribonucleotide length, and oligoribonucleotide and polyribonucleotide structures (such as but not limited to single stranded molecules, double stranded molecules, hybrids containing single and double strands or intra-oligoribonucleotide and intra-polyribonucleotide base-pairing structures) of bacterial RNA are necessary for the biological activity of BRNC. More specifically, the oligoribonucleotide and polyribonucleotide sequences, oligoribonucleotide and polyribonucleotide length, and oligoribonucleotide and polyribonucleotide structures (such as but not limited to single stranded molecules, double stranded molecules, hybrids containing single and double strands or intra-oligoribonucleotide and intra-polyribonucleotide base-pairing structures) of mycobacterial RNA are necessary for biological activity of MRNC. The use of bacterial, mycobacterial or *Mycobacterium phlei, Mycobacterium bovis* BCG, *Mycobacterium. smegmatis, Mycobacterium avium* subsp. *paratuberculosis* or *Mycobacterium vaccae* to formulate BRNC, MRNC, MpRNC, MbRNC, MsRNC, MapRNC and MvRNC cell walls results in a biological carrier and delivery system that is important for maximizing the biological activity (immune stimulation and anti-cancer activity) of BRNC, MRNC, MpRNC, MbRNC, MsRNC, MapRNC and MvRNC.

Methods of Making BRNC, MRNC, MpRNC, MbRNC, MsRNC, MapRNC and MvRNC Containing Different Numbers of Intact Bacterial or Mycobacterial Cells The present invention additionally provides a method for manufacturing BRNC from any bacterial species and strain. Additionally, the present invention additionally provides a method for manufacturing MRNC from any mycobacterial species. Comprehensive listings of mycobacterial species, mycobacterial complexes, mycobacterial sub-species and mycobacterial strains that can be used to prepare mycobacterial cell wall-RNC using the method of the present invention are maintained by and readily available from for example the NCBI of the USA. Preferred mycobacterial species are those that are known to be fast-growing in culture, and thus capable of providing mycobacterial biomass in short periods of time. Also preferred are species that are known to be fast-growing and recognized as being non-pathogenic to immunocompetent individuals.

In one embodiment, the number of intact bacterial cells present in BRNC, MRNC, MpRNC, MbRNC, MsRNC, MapRNC and MvRNC can be controlled by the appropriate use of a defined high-pressure during homogenization and in conjunction with a defined number of homogenization cycles that are used in the preparation of BRNC, MRNC, MpRNC, MbRNC, MsRNC, MapRNC and MvRNC formulations containing bacterial, mycobacterial or *Mycobacterium phlei, Mycobacterium bovis* BCG, *Mycobacterium smegmatis, Mycobacterium avium* subspecies *paratuberculosis* or *Mycobacterium vaccae* cell walls. The inventors have unexpectedly found that varying the number of intact bacterial cells present in BRNC, MRNC, MpRNC, MbRNC, MsRNC, MapRNC and MvRNC can affect the immune stimulatory and anti-cancer activity of these compositions such that the desired and optimal immune modulating or desired and optimal anti-cancer activity can be achieved.

In one embodiment, the number of intact mycobacterial cells in mycobacterial, *Mycobacterium phlei, Mycobacterium bovis* BCG, *Mycobacterium smegmatis, Mycobacterium avium* subspecies *paratuberculosis* or *Mycobacterium vaccae* cell wall formulations of MRNC, MpRNC, MbRNC, MsRNC, MapRNC and MvRNC can be reduced at least 20-fold compared to an equivalent sample of mycobacteria that has not undergone high-pressure homogenization and low-speed centrifugation treatment. In another embodiment, the number of intact mycobacterial cells in, MpRNC, MbRNC, MsRNC, MapRNC and MvRNC can be reduced at least 30-fold compared to an equivalent sample of mycobacteria, *Mycobacterium phlei, Mycobacterium bovis* BCG, *Mycobacterium smegmatis, Mycobacterium avium* subspecies *paratuberculosis* or *Mycobacterium vaccae* that has not undergone high-pressure homogenization, low-speed centrifugation followed by additional high-pressure homogenization treatment of the bacterial cell preparation. In a further embodiment, the number of intact mycobacterial, *Mycobacterium phlei, Mycobacterium bovis* BCG, *Mycobacterium smegmatis, Mycobacterium avium* subspecies *paratuberculosis* or *Mycobacterium vaccae* cells in MRNC, MpRNC, MbRNC, MsRNC, MapRNC and MvRNC can be reduced at least 35-fold compared to an equivalent sample of the mycobacteria that has not undergone high-pressure homogenization, low-speed centrifugation followed by additional high-pressure homogenization treatment of the mycobacterial or *Mycobacterium phlei, Mycobacterium bovis* BCG, *Mycobacterium smegmatis, Mycobacterium avium* subspecies *paratuberculosis* or *Mycobacterium vaccae* cell preparation.

In one embodiment, MRNC, MpRNC, MbRNC, MsRNC, MapRNC and MvRNC compositions containing high levels of intact mycobacterial cell content or *Mycobacterium phlei, Mycobacterium bovis* BCG, *Mycobacterium smegmatis, Mycobacterium avium* subspecies *paratuberculosis* or *Mycobacterium vaccae* cell content, respectively, (e.g. above approximately 1-50% w/w) may be prepared. Such techniques include for example four cycles of high-pressure homogenization, wherein two of the four cycles of high-pressure homogenization are conducted before a high-speed centrifugation step, and two of the high-pressure homogenization steps are conducted after the high-speed centrifugation step.

In another embodiment, MRNC, MpRNC, MbRNC, MsRNC, MapRNC and MvRNC preparations containing intermediate levels of intact mycobacterial cell content, *Mycobacterium phlei, Mycobacterium bovis* BCG, *Mycobacterium smegmatis, Mycobacterium avium* subspecies *paratuberculosis* or *Mycobacterium vaccae* cell content, respectively, (e.g. between from about 0.2 to about 0.9% w/w) may be prepared. Such techniques include, for example seven cycles of high-pressure homogenization, wherein five of the seven cycles of high-pressure homogenization are conducted before a high-speed centrifugation step, and two high-pressure homogenization steps are conducted after the high-speed centrifugation step.

In a further embodiment, MRNC, MpRNC, MbRNC, MsRNC, MapRNC and MvRNC preparations containing ultra-low levels of intact mycobacterial cell content, *Mycobacterium phlei, Mycobacterium bovis* BCG, *Mycobacterium smegmatis, Mycobacterium avium* subspecies *paratuberculosis* or *Mycobacterium vaccae* cell content (e.g. less than from about 0.2% w/w) may be prepared. Such techniques include for example ten cycles of high-pressure homogenization, wherein five of the ten cycles of high-pressure homogenization are conducted before a low-speed centrifugation step, three cycles of high-pressure homogenization are conducted after the low-speed centrifugation and two high-pressure homogenization steps are conducted after the high-speed centrifugation step.

In the above techniques, 'high-pressure homogenization' means a cycle of high-pressure homogenization sufficient to cause the efficient rupture of mycobacteria, *Mycobacterium phlei, Mycobacterium bovis* BCG, *Mycobacterium smegmatis, Mycobacterium avium* subspecies *paratuberculosis* or *Mycobacterium vaccae* such that cell wall fragment compositions containing RNA are obtained. Other procedures that are comparable to high-pressure homogenization such as, but not limited to, microfluidization can also be used. It is to be understood that one of ordinary skill in the art of bacterial and mycobacterial cell disruption, after reading the present invention, can readily determine the optimal pressure for the specific mycobacterial species, strain, substrain, or complex that is to be disrupted.

As defined herein, low-speed centrifugation refers to a relative centrifugal force (RCF) sufficient to sediment undisrupted bacteria, mycobacteria, *Mycobacterium phlei, Mycobacterium bovis* BCG, *Mycobacterium smegmatis, Mycobacterium avium* subspecies *paratuberculosis* or *Mycobacterium vaccae*. It is to be understood that one of ordinary skill in the art of centrifugation, after reading the present invention, can readily determine the optimal RCF for sedimentation of any intact bacteria or mycobacteria that remain following cell disruption as described above.

High-speed centrifugation, as defined herein, refers to a relative centrifugal force sufficient to sediment bacterial, mycobacterial, *Mycobacterium phlei, Mycobacterium bovis* BCG, *Mycobacterium smegmatis, Mycobacterium avium* subspecies *paratuberculosis* or *Mycobacterium vaccae* cell walls. It is to be expected that one of ordinary skill in the art of centrifugation, after reading the present invention, can readily determine the optimal relative centrifugal force for the sedimentation of cell walls from the bacterium or *mycobacterium* following disruption and removal of the desired amount of intact bacteria and mycobacteria by low speed centrifugation as described above.

The use of the above high-pressure homogenization techniques can be used to prepare MRNC containing different levels of intact mycobacteria (for example, of high, intermediate or low) by the appropriate use of high pressure homogenization pressures, low speed centrifugation and high-speed centrifugation, or combinations thereof. Additionally, the high-pressure homogenization techniques described have been used to prepare MRNC, MpRNC, MbRNC, MsRNC, MapRNC and MvRNC containing high, low or intermediate levels of mycobacteria, *Mycobacterium phlei, Mycobacterium bovis* BCG, *Mycobacterium smegmatis, Mycobacterium avium* subspecies *paratuberculosis* or *Mycobacterium vaccae*, respectively.

In one embodiment, MRNC, MpRNC, MbRNC, MsRNC, MapRNC and MvRNC preparations, prepared via the high-pressure homogenization methods described above, contain reduced numbers of intact mycobacterial cells, *Mycobacterium phlei, Mycobacterium bovis* BCG, *Mycobacterium smegmatis, Mycobacterium avium* subspecies *paratuberculosis* or *Mycobacterium vaccae* cells, respectively, as compared to mycobacterial preparations that have undergone differential centrifugation to remove intact mycobacterial cells, *Mycobacterium phlei, Mycobacterium bovis* BCG, *Mycobacterium smegmatis, Mycobacterium avium* subspecies *paratuberculosis* or *Mycobacterium vaccae* cells from the preparation (i.e., no high pressure homogenization treatment). In one embodiment, the percent of intact mycobacterial cells, *Mycobacterium phlei, Mycobacterium bovis* BCG, *Mycobacterium smegmatis, Mycobacterium avium* subspecies *paratuberculosis* or *Mycobacterium vaccae* cells per MRNC, MpRNC, MbRNC, MsRNC, MapRNC and MvRNC preparation (w/w), respectively, is less than about 50% w/w, less than about 40% w/w, less than about 30% w/w, less than about 20% w/w, less than about 10% w/w, less than about 5% w/w, less than about 1% w/w, or less than about 0.5% w/w.

In another embodiment, MRNC, MpRNC, MbRNC, MsRNC, MapRNC and MvRNC preparations are subjected to a process of heat treatment such as but not limited to, for example, heating at 95° C. for 5-30, min or for example heating at 121° C. for 5-30 min, that is sufficient to inactivate any intact mycobacteria, *Mycobacterium phlei, Mycobacterium bovis* BCG, *Mycobacterium smegmatis, Mycobacterium avium* subspecies *paratuberculosis* or *Mycobacterium vaccae* remaining in the composition.

In another embodiment, heat treatment (for example 121° C., 5-30 min or other conditions known to those of skill in the art) of MRNC, MpRNC, MbRNC, MsRNC, MapRNC and MvRNC preparations is used to generate oligoribonucleotides and polyribonucleotides in the range of about 2 to 150, of about 10 to 100, or about 20 to 40 bases in length.

In one embodiment, a method of making MRNC, MpRNC, MbRNC, MsRNC, MapRNC and MvRNC comprises disrupting a mycobacterial cell biomass, *Mycobacterium phlei, Mycobacterium bovis* BCG, *Mycobacterium smegmatis, Mycobacterium avium* subspecies *paratuberculosis* or *Mycobacterium vaccae* to prepare cell walls there from and associated oligoribonucleotides and polyribonucleotides, separating intact non-disrupted mycobacterial, *Mycobacterium phlei, Mycobacterium bovis* BCG, *Mycobacterium smegmatis, Mycobacterium avium* subspecies *paratuberculosis* or *Mycobacterium vaccae* cells; and separating the soluble, cytosolic contents of the portion of the disrupted bacterial mycobacterial, *Mycobacterium phlei, Mycobacterium bovis* BCG, *Mycobacterium smegmatis, Mycobacterium avium* subspecies *paratuberculosis* or *Mycobacterium vaccae* cells from the cell walls and oligoribonucleotides and polyribonucleotides to obtain a bacterial, mycobacterial, *Mycobacterium phlei, Mycobacterium bovis* BCG, *Mycobacterium smegmatis, Mycobacterium avium* subspecies *paratuberculosis* or *Mycobacterium vaccae* cell wall RNC (BRNC, MRNC, MpRNC, MbRNC, MsRNC, MapRNC and MvRNC).

In another embodiment, a method of making MRNC, MpRNC, MbRNC, MsRNC, MapRNC and MvRNC preparations comprises disrupting mycobacterial cell biomass to release oligoribonucleotides and polyribonucleotides; separating the oligoribonucleotides and polyribonucleotides from the non-disrupted, intact mycobacterial, *Mycobacterium phlei, Mycobacterium bovis* BCG, *Mycobacterium smegmatis, Mycobacterium avium* subspecies *paratuberculosis* or

*Mycobacterium vaccae* cells; repeating the steps to control the number of intact mycobacterial, *Mycobacterium phlei*, *Mycobacterium bovis* BCG, *Mycobacterium smegmatis*, *Mycobacterium avium* subspecies *paratuberculosis* or *Mycobacterium vaccae* cells; and, then heating the oligoribonucleotides and polyribonucleotides to a temperature sufficient to obtain an oligoribonucleotide and polyribonucleotide length of about 20 to 40 nucleotide bases.

Nucleic Acid Content of the Compositions

The nucleic acid content of these compositions, MRNC, MpRNC, MbRNC, MsRNC, MapRNC and MvRNC, is from about 500 to 50000 ng/mg, from about 500 to 5000 ng/mg or from about 500 to 3000 ng/mg. In different embodiments, the length of extracted oligoribonucleotides and polyribonucleotides of MRNC, MpRNC, MbRNC, MsRNC, MapRNC and MvRNC is about 2 to about 4000 bases in length, about 2 to about 150 bases in length, or greater than 150 bases in length. In different embodiments, the length of extracted oligoribonucleotides and polyribonucleotides of MRNC, MpRNC, MbRNC, MsRNC, MapRNC and MvRNC is about 150 bases to about 4000 bases in length, or about 10 to about 50 bases in length, or about 20 to about 40 bases in length. In different embodiments, the length of the extracted oligoribonucleotides and polyribonucleotides of MRNC, MpRNC, MbRNC, MsRNC, MapRNC and MvRNC is less than 150 bases, or less than 100 bases.

It will be apparent to one of ordinary skill in the art, that the above procedures may be modified such that other steps are included, providing they do not negatively impact the quality and overall recovery of MRNC, MpRNC, MbRNC, MsRNC, MapRNC and MvRNC.

MRNC, MpRNC, MbRNC, MsRNC, MapRNC and MvRNC increase in their therapeutic effectiveness upon high-pressure homogenization and low-speed centrifugation, because the high-pressure homogenization procedure reduces the length of the extracted RNA molecules by generating oligoribonucleotides and polyribonucleotides, and removes intact mycobacterial, *Mycobacterium phlei*, *Mycobacterium bovis* BCG, *Mycobacterium smegmatis*, *Mycobacterium avium* subspecies *paratuberculosis* or *Mycobacterium vaccae* cells from the respective preparation. Further reductions in the oligoribonucleotide and polyribonucleotide length can be readily achieved by the use of, but not limited to heat treatment (for example, by heat treatment at 121° C. for 30 min) or by the appropriate use of base-sequence restricted endonucleases. The inventors have unexpectedly discovered that MRNC, MpRNC, MbRNC, MsRNC, MapRNC and MvRNC preparations are significantly reduced in their ability to act as immune stimulants or anticancer agents after RNase treatment, which digests RNA. Accordingly, MRNC, MpRNC, MbRNC, MsRNC, MapRNC and MvRNC, preparations have limited therapeutic effectiveness upon RNase treatment or inadvertent exposure to ribonucleases unless the RNA is protected by the use of formulations and carrier systems that restrict access of the RNA to the degradative action of RNase (endo or exo) or nucleases.

Immune Stimulatory and Anticancer Activity of MRNC, MpRNC, MbRNC, MsRNC, MapRNC and MvRNC Reduction in the total number of intact mycobacterial, *Mycobacterium phlei*, *Mycobacterium bovis* BCG, *Mycobacterium smegmatis*, *Mycobacterium avium* subspecies *paratuberculosis* or *Mycobacterium vaccae* cells present in MRNC, MpRNC, MbRNC, MsRNC, MapRNC and MvRNC preparations were found to have a significant effect on immune stimulatory activity as measured by cytokine induction assays. A reduction in the total number of intact mycobacterial cells present in MRNC, MpRNC, MbRNC, MsRNC, MapRNC and MvRNC was also found to have a significant positive effect on immune stimulatory activity, such as increased IL-10 and IL-12p40 induction in peripheral blood mononuclear cells. Furthermore, a reduction in the total number of intact mycobacterial, *Mycobacterium phlei*, *Mycobacterium bovis* BCG, *Mycobacterium smegmatis*, *Mycobacterium avium* subspecies *paratuberculosis* or *Mycobacterium vaccae* cells present in the above preparations was found to have a positive, enhancing effect on the anticancer activity of MRNC, MpRNC, MbRNC, MsRNC, MapRNC and MvRNC, as measured by the inhibition of cancer cell proliferation.

In one embodiment, the immune stimulatory activity of MRNC, MpRNC, MbRNC, MsRNC, MapRNC and MvRNC on hematopoietic and myeloid growth factors in an animal or human can be measured using cytokine induction assays. In another embodiment, MRNC, MpRNC, MbRNC, MsRNC, MapRNC and MvRNC induce immune stimulatory activity of cytokines, including but not limited to, IL-10 and IL-12.

In a further embodiment, therapeutic compositions comprising MRNC, MpRNC, MbRNC, MsRNC, MapRNC and MvRNC possess anti-cancer activity. In one embodiment, the anti-cancer activity of MRNC, MpRNC, MbRNC, MsRNC, MapRNC and MvRNC C may be determined using cancer cell proliferation assays known to those of ordinary skill in the art. The use of such assays to identify anticancer activity is known to those of ordinary skill in the art to be predictive of in vivo anticancer activity.

Administration of compositions comprising MRNC, MpRNC, MbRNC, MsRNC, MapRNC and MvRNC in a prophylactic or therapeutic setting is not in itself an immunization process. It is a prophylactic or therapeutic treatment that stimulates a response in responsive cells of the immune system, and that inhibits proliferation of, and induces apoptosis in responsive cells such as but not limited to cancer cells. This prophylactic or therapeutic treatment is useful to prevent, treat, abate or eliminate a disease including, but not limited to, cancer.

It is to be recognized however that administration of MRNC, MpRNC, MbRNC, MsRNC, MapRNC and MvRNC preparations will elicit an immune response against mycobacterial cell wall components when used in the formulation, that is additionally enhanced by the immune stimulatory activity of the MRNC, MpRNC, MbRNC, MsRNC, MapRNC and MvRNC (immune adjuvant effect). Those of ordinary skill in the art will recognize that such a response will be effective in treating opportunistic or pathogenic mycobacterial infections when the MRNC is prepared therefrom. Specifically, there is a need for a treatment that is capable of reducing the inflammation and morbidity associated with but not limited to tuberculosis, Johne's disease or Crohn's disease. More specifically the use of compositions comprising MapRNC with optimized immune stimulatory and vaccine antigen and vaccine adjuvant activity may be used with advantage to prevent or treat MAP infections in cattle and humans. Compositions comprising RNC from more than one mycobacterial species that contain antigens that cross-react with those of MAP may be used to give rise to a protective response that results in control of MAP infection.

The therapeutic effects of compositions comprising MRNC, MpRNC, MbRNC, MsRNC, MapRNC and MvRNC include, but are not limited to, stimulation of responsive cells of the immune system to produce cytokines, which can result in activation of immune system cells and subsequent cytolysis, or activation of caspases and apoptosis, in responsive cells. Cytolysis and apoptosis, both individually and in combination, have both anticancer activity and adjuvant activity.

That is, therapeutic compositions comprising MRNC, MpRNC, MbRNC, MsRNC, and MvRNC can be administered alone as an anti-cancer agent and that compositions comprising MRNC, MpRNC, MbRNC, MsRNC, MapRNC and MvRNC can be administered before, at the same time as, or after another anti-cancer agent to increase treatment effectiveness.

MRNC, MpRNC, MbRNC, MsRNC, MapRNC and MvRNC are effective prophylactic and therapeutic agents in preventing, treating, lessening and eliminating a variety of diseases including, but not limited to, malignant, autoimmune and immunodeficiency diseases, myelosuppression and hematopoietic and myeloid abnormalities. MRNC, MpRNC, MbRNC, MsRNC, MapRNC and MvRNC are also effective as adjuvants to enhance the effectiveness of other agents. Such agents include, but are not limited to, drugs, antibiotics, other immune stimulants, antigens, antibodies, vaccines, radiation and chemotherapeutic, genetic, biologically engineered and chemically synthesized agents, and agents that target cell death molecules for activation or inactivation, that inhibit proliferation of, and that induce apoptosis in cancer cells.

In each of the aforementioned aspects and embodiments of the invention, combination adjuvants or therapies other than those described above are also specifically contemplated herein.

In one embodiment, the compositions of the present invention may be administered with one or more of currently available chemotherapeutic agents known to one of ordinary skill in the art.

In another embodiment, the compositions of the present invention may be administered with one or more antibiotics, anti-fungicides, anti-viral agents, anti-parasitic agents, anti-inflammatory or immune stimulatory drugs or agents known to one of ordinary skill in the art.

In yet another embodiment, the compositions of the present invention may be administered with one or more drugs or agents known to one ordinary skill in the art for the prevention or treatment of myelosuppression or hematopoietic and myeloid abnormalities.

The compositions of the instant invention may be used for the treatment of animal subjects or patients, and more preferably, mammals, including humans, as well as mammals such as non-human primates, dogs, cats, horses, cattle, swine, rodents and fish.

Pharmaceutically Acceptable Carriers and Methods of Administering the Compositions The composition of MRNC, MpRNC, MbRNC, MsRNC, MapRNC and MvRNC may be readily formulated with, prepared with, or administered with, a pharmaceutically acceptable carrier. Such preparations may be prepared by various techniques. Such techniques include bringing into association the composition of MRNC, MpRNC, MbRNC, MsRNC, MapRNC and MvRNC and its carrier. In one embodiment, the MRNC, MpRNC, MbRNC, MsRNC, MapRNC and MvRNC compositions are prepared by uniformly and intimately bringing into association the MRNC, MpRNC, MbRNC, MsRNC, MapRNC and MvRNC compositions with liquid carriers, with solid carriers, or with both. Liquid carriers include, but are not limited to, aqueous formulations, non-aqueous formulations, or both. Solid carriers include, but are not limited to, biological carriers, chemical carriers, or both.

MRNC, MpRNC, MbRNC, MsRNC, MapRNC and MvRNC compositions may be administered in an aqueous suspension, an oil emulsion, water in oil emulsion and water-in-oil-in-water emulsion, and in carriers including, but not limited to, creams, gels, liposomes (neutral, anionic or cationic), lipid nanospheres or microspheres, neutral, anionic or cationic polymeric nanoparticles or microparticles, site-specific emulsions, long-residence emulsions, sticky-emulsions, micro-emulsions, nano-emulsions, microspheres, nanospheres, nanoparticles and minipumps, and with various natural or synthetic polymers that allow for sustained release of the composition including anionic, neutral or cationic polysaccharides and anionic, neutral cationic polymers or copolymers, the minipumps or polymers being implanted in the vicinity of where composition delivery is required. Polymers and their use are described in, for example, Brem et al. (Journal of Neurosurgery 1991, 74:441-446). Furthermore, MRNC, MpRNC, MbRNC, MsRNC, MapRNC and MvRNC can be used with any one, or any combination of, carriers. These include, but are not limited to, anti-oxidants, buffers, and bacteriostatic agents, and may include suspending agents and thickening agents.

In one embodiment, MRNC, MpRNC, MbRNC, MsRNC, MapRNC and MvRNC compositions or carrier-based preparations are administered as an RNase-free, aqueous suspension. For administration as an aqueous suspension MRNC, MpRNC, MbRNC, MsRNC, MapRNC and MvRNC are suspended in a RNase-free and nuclease free pharmaceutically acceptable excipient, buffer or carrier including, but not limited to, water for injection, physiological saline or dextrose solutions, or by techniques including, but not limited to, high-pressure homogenization, sonication and microfluidization, and can be aseptically processed or terminally sterilized. In another example, freeze-dried (lyophilized) MRNC, MpRNC, MbRNC, MsRNC, MapRNC and MvRNC can be stored in sealed ampoules or vials requiring only the addition of a pharmaceutically acceptable excipient, buffer or carrier, for example RNase-free and nuclease-free sterile water, immediately prior to use.

For administration in a non-aqueous carrier, MRNC, MpRNC, MbRNC, MsRNC, MapRNC and MvRNC may be emulsified with a mineral oil or with a neutral oil such as, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid can be suspended in the neutral oil. More specifically, use can be made of phosphatidylserine, which targets receptors on macrophages. Use can be made of MRNC, MpRNC, MbRNC, MsRNC, MapRNC and MvRNC formulated in aqueous media or of lyophilized MRNC, MpRNC, MbRNC, MsRNC, MapRNC and MvRNC powder in preparing emulsions using techniques known to those of ordinary skill in the art.

The invention thus provides MRNC, MpRNC, MbRNC, MsRNC, MapRNC and MvRNC compositions together with one or more pharmaceutically acceptable carriers and, optionally, other therapeutic and/or prophylactic ingredients. The carrier and other therapeutic ingredients must be acceptable in the sense of being compatible with the other ingredients of the composition and not deleterious to the recipient thereof.

The MRNC, MpRNC, MbRNC, MsRNC, MapRNC and MvRNC compositions are administered in an amount effective to induce a therapeutic response in an animal, including a human. The dosage of MRNC, MpRNC, MbRNC, MsRNC, MapRNC and MvRNC composition administered will depend on the condition being treated, the particular formulation, and other clinical factors such as weight and condition of the recipient and route of administration. In one embodiment, the amount of MRNC, MpRNC, MbRNC, MsRNC, MapRNC and MvRNC administered is from about 0.00001 mg/kg to about 100 mg/kg per dose. In another embodiment, the amount of MRNC, MpRNC, MbRNC, MsRNC, MapRNC and MvRNC administered is from about 0.0001 mg/kg to about 50 mg/kg per dose. In a further embodiment, the amount of MRNC, MpRNC, MbRNC, MsRNC, MapRNC and MvRNC administered is from about 0.001 mg/kg to about 10 mg/kg per dose. In another embodiment, the amount of MRNC, MpRNC, MbRNC, MsRNC, MapRNC and MvRNC administered is from about 0.01 mg/kg to about 5 mg/kg per dose. In a further embodiment, the amount of MRNC, MpRNC, MbRNC, MsRNC, MapRNC and MvRNC administered is from about 0.1 mg/kg to about 1 mg/kg per dose.

Useful dosages of the compounds of the present invention can be determined by comparing their in vitro activity, and in vivo activity in animal models. Methods for the extrapolation of effective dosages in mice, and other animals, to humans are known in the art; for example, see U.S. Pat. No. 4,938,949.

Modes of administration of the compositions used in the invention are exemplified below. However, the compositions can be delivered by any of a variety of routes including: by injection (e.g., subcutaneous, intramuscular, intravenous, intra-arterial, intraperitoneal), by continuous intravenous infusion, cutaneously, dermally, transdermally, orally (e.g., tablet, pill, liquid medicine, edible film strip), by implanted osmotic pumps, by suppository or aerosol spray. Routes of administration include, but are not limited to, topical, intradermal, intrathecal, intralesional, intratumoral, intrabladder, intravaginal, intra-ocular, intrarectal, intrapulmonary, intraspinal, dermal, subdermal, intra-articular, placement within cavities of the body, nasal inhalation, pulmonary inhalation, impression into skin and electroporation.

Depending on the route of administration, the volume of a composition comprising MRNC, MpRNC, MbRNC, MsRNC, MapRNC and MvRNC in an acceptable carrier, per dose, is about 0.001 ml to about 100 ml. In one embodiment, the volume of a composition comprising MRNC, MpRNC, MbRNC, MsRNC, MapRNC and MvRNC in an acceptable carrier, per dose is about 0.01 ml to about 50 ml. In another embodiment, the volume of a composition comprising MRNC, MpRNC, MbRNC, MsRNC, MapRNC and MvRNC in an acceptable carrier, per dose, is about 0.1 ml to about 30 ml. A composition comprising MRNC, MpRNC, MbRNC, MsRNC, MapRNC and MvRNC in an acceptable carrier may be administered in a single dose treatment or in multiple dose treatments, on a schedule, or over a period of time appropriate to the disease being treated, the condition of the recipient and the route of administration. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Methods for Activating Immune System Receptors

The present invention provides methods for activating immune system receptors comprising administering to a subject in need thereof a therapeutically effective amount of MRNC, MpRNC, MbRNC, MsRNC, MapRNC and MvRNC and a pharmaceutically acceptable carrier. Immune system receptors that can be activated by the present invention are (but not limited to) Nucleotide-binding oligomerization domain 2 (NOD2), a pattern recognition receptor (PRR) responsible for sensing the pathogen-associated molecular pattern (PAMP) molecule muramyl dipeptide, the minimal structural component of bacterial peptidoglycan with immune stimulant activity, and Toll-like receptor 2 (TLR2), a pattern recognition receptor (PRR) responsible for sensing a wide range of pathogen-associated molecular pattern (PAMP) molecules such as peptidoglycan, lipomannan (LM), lipoarabinomannan (LAM), and lipoproteins and lipopeptides containing a (palmitic acid)$_n$-derived N-terminus cysteine or cysteines. The activation of these two immune system receptors is known by those of ordinary skill in the art to result in the generation of anticancer activity and anti-infective activity (including but not limited to bacterial, fungal and viral infections), as well as a stimulation of vaccine adjuvant activity and the differentiation of human bone marrow CD14$^+$ cells. The ability of MRNC, MpRNC, MbRNC, MsRNC, MapRNC and MvRNC to function as an agonist for both of these receptors provides an unmet need and further provides significant advantages over monofunctional NOD2 or TLR2 agonists that are used as therapeutic agents in the fields of oncology, infectious diseases or vaccines.

Method for Treating Diseases Including Cancer and Disorders of the Immune System The present invention provides methods for treating cancer comprising administering to a subject in need thereof a therapeutically effective amount of MRNC, MpRNC, MbRNC, MsRNC, MapRNC and MvRNC and a pharmaceutically acceptable carrier.

In another aspect, the methods and compositions of the invention are useful in the therapeutic treatment of cancer, and diseases or disorders of the immune system. In yet a further embodiment, some cancers can be prevented by the timely administration of the compositions as a prophylactic, prior to onset of symptoms, or signs, or prior to onset of severe symptoms or signs of a cancer disease. Thus, a patient at risk for a particular cancer disease can be treated with one or more of the composition of the present invention as a precautionary measure.

In yet another aspect, the present invention is directed to a method of relieving or ameliorating cancer or tumor development, metastasis, cellular proliferation in cancer cells, and/or inhibition of symptoms associated with any one or more of the above-identified cancer diseases and/or cancer indications in a subject suffering from any one or more of the above-identified cancer diseases or cancer indication. This method comprises administering to the subject in need thereof of a therapeutically effective amount of MRNC, MpRNC, MbRNC, MsRNC, MapRNC and MvRNC in a pharmaceutically acceptable carrier. The MRNC, MpRNC, MbRNC, MsRNC, MapRNC and MvRNC may be administered with a pharmaceutically acceptable carrier, either alone or in combination with one or more anti-inflammatory compounds, immune stimulatory agents, or anti-cancer agents, wherein the MRNC, MpRNC, MbRNC, MsRNC, MapRNC and MvRNC is sufficient to inhibit the cancer or tumor development, metastasis, and/or cell proliferation in cancer cells.

MRNC, MpRNC, MbRNC, MsRNC, MapRNC and MvRNC are effective as therapeutic agents for treating, abating or eliminating a disease including, but not limited to, a cancer. Cancers include, but are not limited to, primary or metastatic cancers, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, cancer of the urethra, cervical cancer, endometrial cancer, ovarian cancer, prostate cancer, leukemia, lymphoma and metastases derived there from.

In one aspect, the cancer diseases and cancer disorders that may be treated using the MRNC, MpRNC, MbRNC, MsRNC, MapRNC and MvRNC compositions of the present invention include for example, but not limited to, AIDS-associated cancers, bladder cancer, bone cancer, brain and spinal cord cancers, metastatic brain tumors, pediatric brain tumors, breast cancer, male breast cancer, cervical cancer, colorectal cancer, endometrial and other uterine cancers, esophageal cancer, gallbladder and bile duct cancers, gastric (stomach) cancer, head and neck cancers, kidney cancer, leukemia, liver cancer, liver metastases, lung cancer, lymphomas, mammary adenocarcinoma, melanoma, multiple myeloma, myelodysplastic syndrome, neuroblastoma, osteosarcoma, ovarian cancer, pancreatic cancer, pediatric cancers, pituitary tumors, prostate cancer, hematological disorders, sarcoma, solid tumors, retinoblastoma, skin cancer, soft-tissue sarcoma, testicular cancer, thyroid cancer, uterine cancers, Wilms' tumor, bronchus cancer, colon and rectum cancer, urinary cancer, non-Hodgkin lymphoma, melanomas of the skin, kidney and renal cancer, pelvis cancer, pancreatic cancer, oral cavity cancer and pharynx cancer, stomach esophagus cancer, intrahepatic bile duct cancer, larynx cancer, acute myeloid leukemia, chronic lymphocytic leukemia, soft tissue cancer including heart, GIST (gastro-intestinal stromal tumors), small intestine cancer, chronic myeloid leukemia, acute lymphocytic leukemia, cancer of the anus and anal canal, anorectal cancer, vulva cancer, pleura cancer, malignant mesothelioma, cancer of the bones and joints, hypopharynx cancer, eye and orbit cancer, nose and nasal cavity cancer, middle ear cancer, nasopharynx cancer, ureteral cancer, peritoneum cancer, omentum and mesentery cancer, and gastrointestinal carcinoid tumors or any combination thereof.

In yet another aspect, the cancer diseases and cancer disorders that may be treated using the present invention include, but are not limited to, colorectal cancer, gastric cancer, ovarian cancer, osteosarcoma, hepatocellular carcinoma, Burkitt's lymphoma, primary effusion lymphomas, angioimmunoblastic lymphadenopathy, acquired immune deficiency syndrome (AIDS)-related lymphoma, T-cell lymphomas, oral hairy leukoplakia, lymphoproliferative disease, lymphoepithelial carcinoma, body-cavity-based lymphoma or B-cell lymphomas, non-keratinizing carcinoma, squamous cell nasopharyngeal carcinoma, kidney transplant-associated epithelial tumors, angiosarcoma, Kaposi's sarcoma, angiolymphoid hyperplasia, prostatic neoplasm, retinoblastoma, Li-Fraumeni syndrome, Gardner's syndrome, Werner's syndrome, nervoid basal cell carcinoma syndrome, neurofibromatosis type 1, cervical dysplasia, neuroblastoma, primary macroglobulinemia, insulinoma, mycosis fungoides, osteogenic sarcoma, premalignant skin lesions (topical), rhabdomyosarcoma, osteogenic, polycythemia vera, essential thrombocytosis or any combination thereof. MRNC, MpRNC, MbRNC, MsRNC, MapRNC and MvRNC, may be used as anti-infective agents. The invention is also useful for protecting animals upon exposure to pathogenic materials, such as viruses and bacteria. The present invention is useful for regulating mammalian hematopoiesis or inducing hematopoietic and myeloid recovery (leucopenia, neutropenia, thrombocytopenia or anemia) in animals with cancer recovering from irradiation, surgery or chemotherapeutic treatment. The present invention is useful for the prevention or treatment of diverse hematopoietic and myeloid abnormalities associated with medications or diseases, such as, but not limited to the acquired immunodeficiency syndrome (AIDS), myelodysplastic syndromes, autoimmune diseases, end-stage renal diseases or viral infections.

The present invention is also useful for the treatment or abatement of autoimmune disorders, inflammatory and infectious diseases. MRNC, MpRNC, MbRNC, MsRNC, MapRNC and MvRNC can be used to treat a wide variety of infections caused by viruses, bacteria, mycobacteria (such as but not limited to *Mycobacterium tuberculosis* or *Mycobacterium avium* subspecies *paratuberculosis*), or intracellular organisms including, but not limited to, infection by herpes virus such as equine rhinopneumonitis, infectious bovine rhinotracheitis, endometritis, herpes simplex, herpes zoster, ocular herpes, feline viral rhinotracheitis, and a herpes virus which infects the respiratory tracts of cats. The invention also is effective in the treatment of parvovirus infections of young dogs. The compositions of the present invention are efficacious as a therapeutic agent for genital herpes infections and acquired immune deficiency syndrome of humans, as well as other viral infections of animals and humans. For example, MRNC, MpRNC, MbRNC, MsRNC, MapRNC and MvRNC can be used to treat viral, bacterial, protozoa and fungal infections, such as, but not limited to, Equine Herpes Virus, Equine Influenza Virus, Herpes simplex, Streptococcal species such as but not limited to *Streptococcus zooepidemicus*, *E. coli*, and *Llama Babesia*

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. It is to be understood that one of skill in the art, will upon reading the detailed description and the examples of the present invention apply the findings therein to the preparation of immune stimulatory and anti-cancer RNC from Gram-positive and Gram-negative bacteria without departing from the spirit and intent of the present invention or the scope of the appended claims.

EXAMPLE 1

Cultivation of Mycobacteria in Synthetic Medium

The preparation of mycobacterial cell wall compositions as taught in U.S. Pat. No. 4,744,984 and U.S. Pat. No. 6,326,357 specified the use of BACTO™ AC broth (Difco Labs, now Becton Dickenson) for the preparation of mycobacterial cell mass. This broth contains proteose peptone No. 3, beef extract, yeast extract and malt extract (Difco™ & BBL™ Manual of Microbiological Culture Media, second edition, 2009, pp 35-36). In addition, seed stocks of *Mycobacterium phlei* used as the example in these patents were stored in bovine milk prior to generation of biomass. The aforementioned patents also teach that cultivation is static, and that the mycobacterial cultures grow as a surface pellicle on the culture medium.

In order to eliminate the potential for contamination of mycobacterial biomass by the aforementioned substances, a novel synthetic medium was developed for the cultivation of mycobacteria. Middlebrook 7H9 broth is known to those of ordinary skill in the art to be suitable for the cultivation of pure cultures of mycobacteria but requires the addition of supplements containing animal sourced material (Middlebrook ADC enrichment containing bovine serum albumin and catalase) and additionally benefits from the use of polysorbate 80 or glycerol (Difco™ & BBL™ Manual of Microbiological Culture Media, second edition, 2009, pp 355-356). However, it was unexpectedly found that efficient growth of mycobacteria occurred in Middlebrook 7H9 without the use of the exogenous proteins bovine albumin or catalase that are found in Middlebrook ADC enrichment medium, or of the non-ionic detergent polysorbate 80. It was also unexpectedly found that the use of additional iron (as ferric ammonium citrate) and a source of additional carbon and nitrogen (such as but not limited to asparagine or ammonium citrate) resulted in superior yields of mycobacterial mass when compared to cultivation with Middlebrook 7H9 broth alone. The use of additional carbon, nitrogen and iron in an appropriate ratio is used to facilitate metabolic activity and cell division through optimization of the carbon to nitrogen ratio for the synthesis of proteins, nucleic acids, and other cellular constituents, as well as enhancing metabolism through increased iron availability, thus increasing the mycobacterial division rate and mycobacterial cell mass.

The following results serve to demonstrate the impact of changing the C:N:Fe ratio in the cultivation medium on the growth of *Mycobacterium phlei*, used herein as an example of a representative mycobacterial species. It is to be realized that the findings described below may be replicated by using alternate sources of C, N and Fe, and can be applied to other mycobacteria without departing from the scope and intent of the present invention.

The composition of Middlebrook 7H9 broth and ADC is available in for example the Difco and BBL Manual of Microbiological Culture Media, $2^{nd}$ Edition, 2009, pages 355-356. The growth of *Mycobacterium phlei* was determined in the following newly developed cultivation media, which are defined hereafter as Mycobacterial Culture Media Compositions (MCMC):

A. MCMC composition containing Middlebrook 7H9 (BD Canada, Mississauga, Ontario), glucose and glycerol.

B. MCMC composition containing Middlebrook 7H9 glucose, glycerol and additional Fe (as ferric ammonium citrate) and asparagine as iron, carbon sources and nitrogen sources.

C. MCMC composition containing glucose, glycerol and containing Fe (as ferric ammonium citrate), asparagine and ammonium citrate (dibasic) as iron, carbon and nitrogen sources.

D. MCMC composition containing glucose, glycerol, Fe (as ferric ammonium citrate) and ammonium citrate (dibasic) as iron, carbon and nitrogen sources.

In a separate study the impact of an MCMC composition containing iron and asparagine as the L, DL or D stereoisomer was also determined using Composition C described above.

To prepare MCMC A and MCMC B, Middlebrook 7H9 broth, 9.4 g of Middlebrook 7H9 powdered media was combined with the additives with the exception of glucose, combined with glycerol and additives, dissolved in water (900 mL) and sterilized by steam autoclaving. Glucose was dissolved in water and always filter-sterilized separately and added afterwards to give a final volume of 1000 mL. MCMC C and MCMC D do not contain Middlebrook 7H9 powdered medium. Table 1 shows the mol content of C, N and Fe, per liter cultivation media for Middlebrook 7H9 broth containing glycerol, glucose and the additives described above, as well as the two cultivation media that do not contain Middlebrook 7H9 broth powder.

TABLE 1

C, N and Fe content of synthetic media used to prepare mycobacterial cell mass

| MCMC composition | Carbon* mMol/L | Ratio | Nitrogen** mMol/L | C:N Ratio | Iron*** mM/L | C:Fe Ratio |
|---|---|---|---|---|---|---|
| MCMC-A | 769.30 | 1 | 7.33 | $9.5 \times 10^{-3}$ | 0.14 | $1.8 \times 10^{-4}$ |
| MCMC-B | 792.65 | 1 | 18.80 | $23.71 \times 10^{-3}$ | 0.25 | $3.2 \times 10^{-4}$ |
| MCMC-C | 938.05 | 1 | 61.22 | $61.2 \times 10^{-3}$ | 0.25 | $2.7 \times 10^{-4}$ |

TABLE 1-continued

C, N and Fe content of synthetic media used to prepare mycobacterial cell mass

| MCMC composition | Carbon* mMol/L | Ratio | Nitrogen** mMol/L | C:N Ratio | Iron*** mM/L | C:Fe Ratio |
|---|---|---|---|---|---|---|
| MCMC-D | 915.33 | 1 | 49.86 | $54.5 \times 10^{-3}$ | 0.25 | $2.7 \times 10^{-4}$ |
| MCMC-C (D or L asparagine) | 938.05 | 1 | 61.22 | $61.2 \times 10^{-3}$ | 0.25 | $2.7 \times 10^{-4}$ |

*All available (metabolically) carbon has been used in the calculation.
**All available (metabolically) nitrogen has been used in the calculation.
***All available iron has been used in the calculation.
Ferric ammonium citrate is defined as $C_6H_{10}FeNO_8$ Middlebrook 7H9 powder was obtained from BD Canada, Mississauga, Ontario and is known to one of ordinary skill in the art. The approximate formula for making about 900 mL of Difco™ Middlebrook 7H9 Broth is as follows: Ammonium Sulfate (0.5 g), L-Glutamic Acid (0.5 g), Sodium Citrate (0.1 g), Pyridoxine (1.0 mg), Biotin (0.5 mg), Disodium Phosphate (2.5 g), Monopotassium Phosphate (1.0 g), Ferric Ammonium Citrate (0.04 g), Magnesium Sulfate (0.05 g), Calcium Chloride (0.5 mg), Zinc Sulfate (1.0 mg), Copper Sulfate (1.0 mg).

All other reagents were from Sigma, Oakville, Ontario. The composition in g/L of the cultivation media used to prepare MCMC-A, MCMC-B, MCMC-C and MCMC-D are shown below. However it is to be understood that while each specific number listed is for one recipe of MCMC-A, MCMC-B, MCMC-C and MCMC-D, each of these numbers may be increased or decreased by about 10% to about 20% to make variations of the MCMC-A, MCMC-B, MCMC-C and MCMC-D cultivation media, with corresponding changes in the C:N and C:Fe ratios.

MCMC-A.

| Middlebrook 7H9 powder | 9.5 g |
|---|---|
| Glycerol | 2 mL |
| Glucose | 20 g |
| Distilled water | to 1 L |

MCMC-B

| Middlebrook 7H9 powder | 9.5 g |
|---|---|
| DL-Asparagine | 0.75 g |
| Ferric ammonium citrate | 0.03 g |
| Glycerol | 2 mL |
| Glucose | 20 g |
| Distilled water | to 1 L |

MCMC-C

| Ammonium citrate | 4.84 g |
|---|---|
| DL-Asparagine | 0.75 g |
| L-Glutamic acid | 1.0 g |
| Pyridoxine | 0.002 g |
| Biotin | 0.0005 g |
| Disodium phosphate | 5 g |
| Monopotassium phosphate | 2.0 g |
| Ferric ammonium citrate | 0.12 g |
| Magnesium sulfate | 0.25 g |
| Calcium chloride | 0.0005 g |
| Zinc sulfate | 0.005 g |
| Oleic acid | 0.125 g |

-continued

| | |
|---|---|
| Glycerol | 2 mL |
| Glucose | 20 g |
| Distilled water | to 1 L |

MCMC-C (D-asparagine)

| | |
|---|---|
| Ammonium citrate | 4.84 g |
| D-Asparagine | 0.75 g |
| L-glutamic acid | 1.0 g |
| Pyridoxine | 0.002 g |
| Biotin | 0.0005 g |
| Disodium phosphate | 5 g |
| Monopotassium phosphate | 2.0 g |
| Ferric ammonium citrate | 0.12 g |
| Magnesium sulfate | 0.25 g |
| Calcium chloride | 0.0005 g |
| Zinc sulfate | 0.005 g |
| Oleic acid | 0.125 g |
| Glycerol | 2 mL |
| Glucose | 20 g |
| Distilled water | to 1 L |

MCMC-C (L asparagine)

| | |
|---|---|
| Ammonium citrate | 4.84 g |
| L-Asparagine | 0.75 g |
| L-glutamic acid | 1.0 g |
| Pyridoxine | 0.002 g |
| Biotin | 0.0005 g |
| Disodium phosphate | 5 g |
| Monopotassium phosphate | 2.0 g |
| Ferric ammonium citrate | 0.12 g |
| Magnesium sulfate | 0.25 g |
| Calcium chloride | 0.0005 g |
| Zinc sulfate | 0.005 g |
| Oleic acid | 0.125 g |
| Glycerol | 2 mL |
| Glucose | 20 g |
| Distilled water | to 1 L |

MCMC-D

| | |
|---|---|
| Ammonium citrate | 4.84 g |
| L-glutamic acid | 1.0 g |
| Pyridoxine | 0.002 g |
| Biotin | 0.0005 g |
| Disodium phosphate | 5 g |
| Monopotassium phosphate | 2.0 g |
| Ferric ammonium citrate | 1.2 g |
| Magnesium sulfate | 0.25 g |
| Calcium chloride | 0.0005 g |
| Zinc sulfate | 0.005 g |
| Oleic acid | 0.125 g |
| Glycerol | 2 mL |
| Glucose | 20 g |
| Distilled water | to 1 L |

The following procedure describes the preparation of mycobacterial cell mass from *Mycobacterium phlei*, and therefore serves as a general example for the preparation of mycobacterial cell mass from mycobacteria in general. It is recognized that one of ordinary skill in the art on reading this example will appropriately modify the procedures to address the specific needs of individual mycobacterial species, complexes and strains.

*Mycobacterium phlei* (strain 110) was stored as colonies on Petriagani slants at 4° C. or as a suspension in Middlebrook 7H9 containing 20% glycerol at −80° C. Determination of optimal cultivation carbon, nitrogen and iron ratios was conducted using seed cultures prepared from Petriagani slants. Colonies from the Petriagani slant were placed in 1.2 L of the M Medium and after dispersion were cultivated for 7 days (250 rpm, 37° C. in an orbital shaker, Lab-Line Instruments, Melrose Park, Ill., USA). After adjustment to a standardized OD, 200 mL were added to a series of culture flasks containing 1 L of the respective MCMC. Cultivation was continued (250 rpm, 37° C. in an LAB-Line orbital shaker), and replicate flasks were removed at intervals over a period of 10 days. Mycobacterial mass was isolated by low speed centrifugation washing, lyophilized and the dry weight determined. Where lyophilization was impractical, dry weight was calculated from wet cell mass using the conversion factor wet cell mass/6.81=dry cell mass (the mean±SD for this factor was previously determined by experimentation to be 6.81±1.16, n=7).

The results in Table 2 show the impact of different carbon, nitrogen and iron ratios in the MCMC on the yield of *Mycobacterium phlei*, as well as the time of optimal yield in days, and the results in Table 3 shows the impact of using racemic DL-, D- or L-asparagine on the yield of mycobacterial cell mass. It is to be understood that these studies were conducted at different times, and that the absolute yields of mycobacterial cell mass vary from study to study.

TABLE 2

Impact of C, N and Fe content on yield of *Mycobacterium phlei* cell mass

| MCMC Composition | Yield, g/L* (fold increase versus A) | Day |
|---|---|---|
| A | 4.52 | 10 |
| B | 4.16 (0.9) | 6 |
| C | 6.24 (1.4) | 6 |
| D | 6.20 (1.4) | 4 |

*Yield is expressed as g dry weight *mycobacterium phlei* per liter of culture broth.

TABLE 3

Impact of asparagine stereoisomer D, L or a DL racemic mixture on the yield of *Mycobacterium phlei*

| MCMC Composition | Yield, g/L (fold increase versus DL asparagine) | Optimal yield, day |
|---|---|---|
| C using DL-asparagine | 4.9 | 6 |
| C using D-asparagine | 4.9 (0) | 6 |
| C using L-asparagine | 5.73 (1.2) | 6 |

The results shown in Table 2 demonstrate that increasing the amount of available carbon, nitrogen and iron gives rise to increases in the yield of cell mass, as well as decreasing the time required to obtain maximal yield. The results also show that the use of, for example, but not limited to asparagine or ammonium citrate (i.e., an available source of nitrogen, whether it is in the form of an organic or inorganic molecule) increases the yield. Two advantages associated with the use of ammonium citrate rather than ammonium sulfate, are the relatively slow metabolism of the carbons of citrate (the salt of a weak acid, which provides substantial buffering capacity to the medium) and the observed reduced fluctuations in the pH of the broth during cultivation that are consistent with the generation of sulfuric acid from the non-metabolizable sulfate (the salt of a strong acid).

The results shown in Table 3 demonstrate that the use of D-asparagine or a racemic mixture if DL asparagine gave lower mycobacterial cell mass yield than when the L-stereoisomer was used. These data are consistent with a more efficient utilization of the L-stereoisomer of asparagine rather than the D-stereoisomer or the racemic mixture. Ammonium citrate would appear to possess a further advantage as a source of nitrogen in that the ammonium ions are not racemic.

A third study was conducted using the optimized MCMC-C where *Mycobacterium phlei* and *Mycobacterium smegmatis* yields were compared. *Mycobacterium smegmatis* (ATCC, Manassas, Va., strain ATCC14468) was prepared as described for *Mycobacterium phlei*, and head-to-head cultivations were performed as described above.

TABLE 4

Use of MCMC-C for the preparation of *Mycobacterium phlei* and *Mycobacterium smegmatis* cell mass

| Mycobacterium | Yield, g dry weight/L | Optimal yield, day |
|---|---|---|
| Mycobacterium phlei | 7.6 | 6 |
| Mycobacterium smegmatis | 9.6 | 6 |

The results shown in Table 4 demonstrate that the use of the MCMC composition C results in significant quantities of mycobacterial cell mass in a relatively short period of time, and that such yields are not restricted to *Mycobacterium phlei*

A separate study was performed in order to determine the effect of additional aeration of the medium during cultivation. Cultivation of *Mycobacterium phlei* was carried out as described above, except that tripled baffled Fermbach flasks were used in order to increase mixing of the medium and access to atmospheric oxygen. The growth of *Mycobacterium phlei* in MCMC-C medium was compared with its growth in Bacto™ AC broth and MCMC-A. *Mycobacterium phlei* cell mass yield at 120 hours was determined as g dry weight mycobacterial cell mass/liter cultivation medium. The results showed that using Bacto™ AC broth the yield was 5.0 g/L, using MCMC-A the yield was 3.15 g/L, and using MCMC-C the yield was 9.2 g/L (2.9-fold increase versus MCMC-A and 1.84-fold increase versus Bacto™ AC broth). These data demonstrate that under cultivation conditions that increase mixing and aeration (such as but not limited to Fermbach flasks) there are further increases in the yield of *Mycobacterium phlei*, and that the yield in the new medium composition is greater than that found with either Bacto™ AC broth or MCMC-A.

Preparation of mycobacterial cell wall RNC of the present invention was conducted using seed cultures of mycobacteria prepared from frozen stocks. A seed culture was prepared from frozen stock by adding 1 vial of the frozen stock to 600 mL of the modified culture medium, and cultivation was carried out for 7 days at 37° C. with agitation in an orbital shaker at 160-250 rpm (Lab-Line, Melrose Park, Ill., USA). The seed culture was then used to inoculate a larger culture volume at a 1:10 dilution, and cultivation carried out using the same conditions for 7 days. Mycobacterial biomass was harvested by low speed centrifugal washing, after which the pelleted mycobacteria were resuspended in water for injection (nuclease-free) to give a 10% w/v suspension. The compositions of the present invention were prepared from this suspension as described in the Examples below.

Typically, the cultivation of *Mycobacterium phlei* as described in U.S. Pat. No. 6,326,357 takes between 7-10 days for the generation of a seed culture and an additional 10 to 20 days for the generation of mycobacterial cell biomass (cultivation total time between 17-30 days). The yield of this manufacturing process is approximately 20 g wet weight *Mycobacterium phlei*/liter of culture medium, corresponding to a dry weight of approximately 2-3 g *Mycobacterium phlei*/liter. The new manufacturing process described above using the MCMC compositions and cultivation conditions takes 14 days in total, and the yield is approximately 6.5-7.6 g dry weight *Mycobacterium phlei*/liter, thus providing a significant decrease in the time required to prepare the biomass in addition to a significant increase in the yield of mycobacterial cell mass. Such improvements provide unexpected increases in biomass production efficiency when compared to previous teachings.

It is to be realized that the important principles described in this example are the use of a cultivation medium for the preparation of mycobacterial cell mass that does not contain exogenous animal, plant or fungal material, and a cultivation process that optimizes the growth of the mycobacteria through the use of an optimized medium in conjunction with agitation to maintain the mycobacteria in suspension, rather than as a pellicle that is characteristic of stationary growth cultivation conditions. Modification to these principles may be made by one of ordinary skill in the art after reading this example that result in optimal growth of a particular mycobacterial species, complex or strain without departing from the spirit of the present invention and/or the scope of the appended claims.

EXAMPLE 2

Controlling the Number of Intact Mycobacteria During the Preparation of Immune Stimulatory and Anticancer Compositions The following example identifies new procedures for the preparation of the compositions of the present invention that use working volumes that are scalable, range from several mL to multi-liter volumes, and that result in the efficient production of new bacterial compositions comprising nucleic acids and cell walls.

Mycobacterial cell mass (*Mycobacterium phlei* is used as an illustrative and representative example of mycobacterial cell mass) was prepared as described in Example 1. After pelleting by low-speed centrifugation to remove culture medium components, *M. phlei* cells (prepared as a 10% w/v suspension in DNase- and RNase-free water for injection) was disrupted by high-pressure homogenization (18,000 pounds per square inch [PSI], 5 cycles, at a temperature of 4° C.) using an Avestin EmulsiFlex-05 high-pressure homogenizer (Avestin, Ottawa, Ontario, Canada). Resort may be made to similar or equivalent systems without departure from the present invention. The homogenate was then centrifuged at a relative centrifugal force identified as being optimal for the removal of intact mycobacteria (3,160×g for 30 min at 4° C.). In this example, samples of the 10% w/v *M. phlei* suspension, the homogenate after high-pressure homogenization, the supernatant from the low-speed centrifugation (containing intact and contaminating *M. phlei*) and the supernatant from the low-speed centrifugation that had been subjected to additional cycles of high-pressure homogenization were serially diluted (dilutions of $10^{-2}$ to $10^{-7}$ in water for injection) and the number of colony-forming units (CFU) determined by plating on tryptic soy agar growth media, incubating for 72-96 h at 37° C., and counting the colonies and expressing them as CFU/mL.

The Avestin high-pressure homogenization system has been reported to achieve ~100% disruption of yeast and *Escherichia coli* cells after 1-3 cycles. The failure of 5 homogenization steps to achieve 100% disruption of *Mycobacterium phlei* would indicate to those of skill in the art that this would be the limit of efficiency for this microorganism. Unexpectedly however it was found that subjecting the low-speed centrifugation supernatant containing intact *Mycobacterium phlei* cells that were apparently resistant to 5 cycles of high-pressure homogenization to additional steps (2-3) of high-pressure homogenization at 18,000 PSI at a temperature of 4° C. resulted in further reductions in intact *Mycobacterium phlei* cells (Table 5). The unexpected benefits of additional high-pressure homogenization steps are further controlled reductions in the number of intact *Mycobacterium phlei* cells and an increase in the yield of mycobacterial cell wall-RNC.

As *Mycobacterium phlei* grows in aggregates of cells in suspension culture, it is impossible to directly determine the number of CFUs in the mycobacterial suspension (determined to be an approximately 100-fold underestimation). Use was made of a calculated estimation determined as follows: The size of the microorganism as shown in FIG. 1 is similar to that of *Escherichia coli* (0.5×2 µm: Imaging whole *Escherichia coli* bacteria by using single-particle x-ray diffraction. Miao J, et al. PNAS 2003, 100:110-112), thus allowing a calculation of the estimated CFU of a 10% w/v suspension of *Mycobacterium phlei* based on the weight of individual *Escherichia coli*, which is 665 femtograms (fg) (Single cell detection with micromechanical oscillators. Illic, B, et al., J. Vac. Sci. Technol. B. 2001, 19(6):2825-2828)

TABLE 5

Effect of high pressure homogenization on the number of intact mycobacteria

| Sample | CFU/mL |
| --- | --- |
| 10% w/.v suspension (calculated estimation) | $1.5 \times 10^{11}$ |
| High-pressure homogenization (5 cycles) | $8.7 \times 10^{8}$ |
| Low-speed centrifugation supernatant | $3.0 \times 10^{7}$ |
| Low-speed centrifugation supernatant following by 3 additional high-pressure homogenization cycles | $1.9 \times 10^{7}$ |

The results shown in Table 5 demonstrate that the use of 5 cycles of high-pressure homogenization is consistent with the efficient disruption of the mycobacteria in the suspension (99.42%—based on the above calculation). The low-speed centrifugation after 5 cycles of high-pressure homogenization resulted in a 5.000-fold reduction in the number of intact, viable mycobacterial cells as compared to an equivalent *M. phlei* sample that had not undergone high-pressure homogenization. The use of further high-pressure homogenization steps using the supernatant from the low-speed centrifugation resulted in an additional 0.007% content representing a 2.895-fold reduction in the number of intact, viable mycobacterial cells as compared to an equivalent *Mycobacterium phlei* samples that had not undergone high-pressure homogenization.

It is to be realized that the important principles demonstrated in this example are the unexpected benefits arising from the use of additional homogenization steps are further disruption of intact mycobacteria, which as Gram-positive microorganisms are considered to be resistant to high-pressure homogenization, and the ability to control through the use of differing homogenization steps the level of intact mycobacteria in the mycobacterial cell wall RNC fraction contained in the low-speed centrifugation supernatant.

EXAMPLE 3

Preparation of Compositions Comprising Mycobacterial Cell Walls and RNA (MpRNC)

To further demonstrate the utility of the new approach described above to prepare mycobacterial cell wall compositions, new procedures were developed that required the use of different homogenization pressures and number of homogenization cycles that enabled the preparation of new mycobacterial cell wall-RNA compositions (MRNC) formulated with mycobacterial cell walls and comprising: a) a controlled reduction in the intact mycobacterial cell content; b) the generation of oligoribonucleotides and polyribonucleotides of defined length, and c) the generation of unexpected immune stimulant activity.

In this example mycobacterial cell mass (*Mycobacterium phlei* is used as an illustrative and representative example of mycobacterial cell mass, and it is to be realized that the manufacturing procedures described in this example are applicable to both bacteria and mycobacteria) was prepared as described in Example 1. Intact *Mycobacterium phlei* cells were first washed by low-speed centrifugation to remove culture medium components, and were then disrupted using high-pressure homogenization with an Avestin EmulsiFlex-C5 high-pressure homogenizer (Avestin, Ottawa, Ontario, Canada). After high-pressure homogenization the remaining intact mycobacterial cells were removed by differential centrifugation using relative centrifugal forces that were optimized for the controlled removal of any residual, intact and undisrupted mycobacteria as well as the elimination of soluble material (cytoplasmic contents including proteins). The intact mycobacterial cell-free preparation, comprising the RNA of the *mycobacterium* in the form of oligoribonucleotides and polyribonucleotides associated with mycobacterial cell wall fragments, was further purified by centrifugation washing at a higher relative centrifugal force, in order to remove soluble contaminants. The MpRNC fraction was isolated as a pellet following centrifugation washing at high relative centrifugal force. The number of live mycobacteria in the MpRNC fraction was determined by plating serial dilutions of the mycobacterial intact cell-free fraction on tryptic soy agar growth media, incubating for 72-96 h at 37° C., and determining the number of colony forming units (CFUs). The MpRNC suspension was then heat-treated at 121° C. for between 5-30 min. Table 6 shows the steps used to prepare MpRNC with a high-, an intermediate-, or with a low intact mycobacterial cell content (hereafter referred to as MpRNC High, MpRNC Intermediate and MpRNC Low, respectively).

TABLE 6

Preparation of MpRNC containing High, Intermediate and Low levels of intact *Mycobacterium phlei*

| Step | MpRNC High | MpRNC Intermediate | MpRNC Low |
| --- | --- | --- | --- |
| 1 | High-pressure homogenization, 10,000 PSI, 2 cycles | High-pressure homogenization, 18,000 PSI, 5 cycles | High-pressure homogenization, 27,000 PSI, 5 cycles |

TABLE 6-continued

Preparation of MpRNC containing High, Intermediate and Low levels of intact *Mycobacterium phlei*

| Step | MpRNC High | MpRNC Intermediate | MpRNC Low |
|---|---|---|---|
| 2 | High-speed centrifugation, 38,400 × RCF, to pellet MpRNC and any remaining intact cells | Low-speed centrifugation, 3,160 × RCF to remove intact cells | Low-speed centrifugation, 3,160 × RCF to remove intact cells |
| 3 | High-pressure homogenization, 10,000 psi, of resuspended MpRNC pellet 2 cycles | High-speed centrifugation, 38,400 × RCF to pellet MpRNC and any remaining intact cells | High-pressure homogenization, 27,000 psi, to further reduce intact cell content 3 cycles |
| 4 | MpRNC High | High-pressure homogenization, 18,000 psi, of resuspended MpRNC pellet 2 cycles | High-speed centrifugation, 38,400 × RCF to pellet MpRNC and any remaining intact cells |
| 5 |  | MpRNC Intermediate | High-pressure homogenization, 27,000 psi, of resuspended MpRNC pellet 2 cycles |
| 6 |  |  | MpRNC Low |

The results shown in Table 7 show the number of CFUs in MpRNC prepared using the various procedures described in Table 6.

TABLE 7

Preparation of MpRNC with differing levels of intact mycobacterial cell content

| MpRNC | Homogenization pressure, psi | Differential centrifugation RCF (low; high) | Mycobacterial CFU/mg MpRNC | % Intact mycobacteria (w/w)* |
|---|---|---|---|---|
| A) High *Mycobacterium phlei* cell content | 10,000, 4 cycles (2 before high-speed centrifugation, 2 after) | None; 38,400 | $2.94 \times 10^8$ | 19.6% |
| B) Intermediate *Mycobacterium phlei* cell content | 18,000, 7 cycles (5 before low-speed centrifugation, 2 cycles after high-speed centrifugation) | 3,160; 38,400 | $1.00 \times 10^7$ | 0.66% |
| C) Low *Mycobacterium phlei* cell content | 27,000, 10 cycles (5 before low-speed centrifugation, 3 cycles after low-speed centrifugation, 2 cycles after high-speed centrifugation) | 3,160; 38,400 | $2.88 \times 10^6$ | 0.19% |

*Based on an intact bacterial weight of 665 fg/bacterium (Single cell detection with micromechanical oscillators. Illic, B, et al., J. Vac. Sci. Technol. 2001, B. 19(6): 2825-2828)

The data show that by increasing the homogenization pressure and the number of homogenization cycles that the MpRNC undergoes a significant and more importantly a controlled reduction in the number of viable intact *Mycobacterium phlei* cells present in the MpRNC. Calculation of the % weight of intact mycobacteria (based on a bacterial weight of 665 fg) showed a controlled range of <0.2% (MpRNC low) to 19.6% (MpRNC high). Those of skill in the art will recognize that the number of viable mycobacterial cells in the MpRNC can therefore be readily controlled over a 100-fold range by the appropriate use of a defined method, such as the controlled use of homogenization pressure, the number of homogenization cycles and the use of differential centrifugation as described in the present invention.

EXAMPLE 4

Preparation of MRNC from *Mycobacterium bovis* Strain BCG, *Mycobacterium smegmatis* and *Mycobacterium vaccae*

In this example, three different mycobacteria, one known to be slow growing in culture and two known to be fast growing in culture, were used to prepare different MRNC compositions. As such, this example in conjunction with Examples 1, 2 and 3 of the present invention teaches one of skill in the art how to prepare MRNC from any mycobacterial species or strain. In order to preserve the nucleic acid composition nuclease-free (RNase-free and DNase-free) reagents were used throughout. One of ordinary skill in the art on reading the present invention will also recognize that application of the use of different homogenization cycles and pressures, and the selective use of differential centrifugation, as described in detail in Examples 1, 2 and 3 for the preparation of MpRNC from *Mycobacterium phlei*, enables the preparation of RNC compositions containing the optimal level of intact mycobacterial cells from other species for the desired application.

*Mycobacterium bovis* BCG from mycobacterial biomass or from commercially available sources can be used to prepare MbRNC compositions. In this example the Connaught strain of BCG was used. BCG is available commercially as a lyophilized power containing $2-10 \times 10^8$ CFU/mg (Immucyst, Aventis, Toronto, ON, Canada). The lyophilized powder was first resuspended in water for injection (Wisent) for 30 min 20° C. with intermittent vortexing. The suspended cells were pelleted by low-speed centrifugation and then disrupted using high-pressure homogenization with an Avestin EmulsiFlex-05 high-pressure homogenizer followed by differential centrifugation to isolate MbRNC as described for MpRNC Intermediate with minor modification. Specifically, a 0.243% w/v *Mycobacterium bovis* BCG suspension in water for injection was subjected to 5 cycles of high-pressure homogenization at 18,000 psi with a heat exchanger circulating water at 4° C. The homogenate was then centrifuged at 3,160×g for 30 min to sediment any residual, intact and undisrupted *Mycobacterium bovis* BCG. The supernatant, containing RNC of the *mycobacterium* associated with mycobacterial cell wall fragments, was then centrifuged at 38,400×g for 1 hour to remove soluble contaminants and to pellet RNC and *Mycobacterium bovis* BCG cell walls (MbRNC). The pellet was then re-suspended in water for injection and was homogenized for two additional cycles as described above. The suspension containing *Mycobacterium bovis* MbRNC was heat-treated at 121° C. for between 5-30 min.

*Mycobacterium smegmatis* (obtained from the ATCC, Manassas, Va., strain 14468) from cultivated mycobacterial biomass was used to prepare MsRNC. *Mycobacterium smegmatis* cells were prepared as described in Example 1. Intact mycobacteria (*Mycobacterium smegmatis*) were first washed by low-speed centrifugation to remove culture medium components, and were then disrupted using high-pressure homogenization with an Avestin EmulsiFlex-05 high-pressure homogenizer followed by differential centrifugation as described in for MpRNC. In detail, a 10% w/v *Mycobacterium smegmatis* cell suspension in water for injection was subjected to 5 cycles of high-pressure homogenization at 18,000 psi. The homogenate was then centrifuged at 3,160×g for 30 min at 4° C. to sediment intact and undisrupted *mycobacterium*. The supernatant, containing RNA of the *mycobacterium* associated with mycobacterial cell wall fragments, was then centrifuged at 38,400×g for 1 hour at 4° C. to remove soluble contaminants and to pellet MsRNC. The MsRNC pellet was then re-suspended in water for injection and was homogenized for two additional cycles as described above. The suspension containing *Mycobacterium smegmatis* RNC (MsRNC) was heat-treated at 121° C. for between 5-30 min.

*Mycobacterium vaccae* (strain ATCC15483, American Typing Culture Collections, Manassas, Va., USA) was cultivated in Middlebrook 7H9 broth supplied with OADC enrichment (BD Diagnostic System, Sparks, Md., USA). The pelleted bacteria were stored at −20° C. prior to use). The use of Middlebrook 7H9 broth supplied with OADC enrichment (BD) allowed optimal growth of *Mycobacterium vaccae* as compared to the growth in the synthetic medium due to the presence of as yet unknown growth factor(s) in the OADC enrichment. In this example, use was made of the new manufacturing method described herein to ensure no additional exposure to exogenous materials. The cells were first washed by low-speed centrifugation to remove culture medium components, and were then disrupted using high-pressure homogenization with an Avestin EmulsiFlex-05 high-pressure homogenizer followed by differential centrifugation as described for MpRNC. In detail, a 10% w/v *Mycobacterium vaccae* suspension in water for injection was subjected to 5 passages of high-pressure homogenization at 18,000 psi. The supernatant, containing RNA of the *mycobacterium* associated with mycobacterial cell wall fragments, was then centrifuged at 38,400×g for 1 hour to remove soluble contaminants and to pellet MvRNC. The pellet was then re-suspended in water for injection and was homogenized for two additional cycles as described above. The suspension containing *Mycobacterium vaccae* RNC (MvRNC) was heat-treated at 121° C. for between 5-30 min.

EXAMPLE 5

Preparation of BRNC from Gram-Negative Bacteria

The BRNC compositions of the present invention can be prepared from one or several Gram negative bacteria by for example disruption of the bacterium followed by phenol/chloroform/isoamyl alcohol extraction and ethanol precipitation (as described in Short Protocols in Molecular Biology, 3rd Edition, Ausubel et al. Eds., John Wiley & Sons Inc., New York, USA). Use may be made of enzymatic procedures that are designed to digest unwanted chemical species prior to extraction of nucleic acid-containing compositions and thus optimize the yield. For example, Gram-negative bacteria were suspended in 5 mL RNase-free 50 mM Tris-HCl, 5 mM EDTA, pH 8.0, adding RNase-free lysozyme (Sigma-Aldrich) to a concentration of 1 mg/mL and incubating for 90 min at 37° C. RNase-free proteinase K (Invitrogen, Burlington, Ontario, Canada) was then added to give a final concentration of 0.1 mg/mL, RNase-free sodium dodecyl sulfate (BioRad, Richmond, Calif.) was added to give a final concentration of 1% w/v, and the incubation continued for 10 min at 65° C. Nucleic acid is then isolated by phenol/chloroform/isoamyl alcohol extraction. RNA-containing compositions can optionally be treated (for example, by the use of high-pressure homogenization, mechanical shearing, sonication, or autoclaving) to generate the oligoribonucleotides and polyribonucleotides of the present invention.

The bacterial RNA can optionally be used to prepare bacterial cell wall RNC formulations (BRNC), by the use of high-pressure homogenization and differential centrifugation and heat treatment as described in Examples 1, 2, 3 and 4 of the present invention, such that they have anticancer and immune stimulant activity. The BRNC can be further combined with pharmaceutical carriers such as but not limited to cationic liposomes or nanoparticles as described in Examples 36 and 37.

EXAMPLE 6

Preparation of BRNC or MRNC from Gram-Positive Bacteria

The BRNC compositions and the MRNC compositions of the present invention can be prepared from one or several Gram positive bacteria (including mycobacteria) by, for example, disruption of the bacterium or *mycobacterium* followed by phenol/chloroform/isoamyl alcohol extraction and ethanol precipitation (as described in Short Protocols in Molecular Biology, 3rd Edition, Ausubel et al. Eds., John Wiley & Sons Inc., New York, USA). Use may be made of enzymatic procedures that are designed to digest unwanted chemical species prior to extraction of RNA and thus optimize the yield. As an example of the applicability of the novel procedures described above. Gram-positive bacteria are suspended in 5 mL RNase-free 50 mM Tris-HCl, 5 mM EDTA, pH 8.0, adding RNase-free lysozyme (Sigma-Aldrich) to a concentration of 1 mg/mL and incubating for 90 min at 37° C. RNase-free proteinase K (prepared from *Tritirachium album*. Invitrogen, Burlington, Ontario, Canada) is then added to give a final concentration of 0.1 mg/mL, RNase-free sodium dodecyl sulfate (BioRad, Mississauga, Ontario, Canada) is added to give a final concentration of 1% w/v, and the incubation continued for 10 min at 65° C. RNA is then isolated by phenol/chloroform/isoamyl alcohol extraction and ethanol precipitation The BRNC and MRNC can optionally be treated (for example, by the use of high-pressure homogenization, mechanical shearing, sonication, or heat treatment) to generate the oligoribonucleotides and polyribonucleotides of the present invention.

The bacterial RNA can optionally be used to prepare BRNC formulations, by the use of high-pressure homogenization and differential centrifugation and heat treatment as described in Examples 1, 2, 3 and 4 of the present invention, such that they have anticancer and immune stimulant activity. The bacterial RNC can be further combined with pharmaceutical carriers such as but not limited to cationic liposomes or nanoparticles as described in Examples 36 and 37.

The mycobacterial RNA can optionally be used to prepare MRNC formulations, by the use of high-pressure homogenization and differential centrifugation and heat treatment as described in Examples 1, 2, 3 and 4 of the present invention, such that they have anticancer and immune stimulant activity. The MRNC can be further combined with pharmaceutical carriers such as but not limited to cationic liposomes or nanoparticles as described in Examples 36 and 37.

EXAMPLE 7

Morphological Examination of Mycobacterial Cell Wall Compositions for Intact Mycobacterial Cells A morphological comparison of mycobacterial cell wall compositions was carried out using transmission electron microscopy (TEM). It is to be realized that in this example MpRNC is used as an illustrative and representative example of the intact cell content of BRNC and MRNC.

A sample of *Mycobacterium phlei* biomass was prepared as described in Example 1, a sample of MpRNC High, Intermediate and Low was prepared as described in Example 3, a sample of MCC was prepared as described in U.S. Pat. No. 6,326,357, a sample of MCWE was prepared as described in U.S. Pat. No. 5,759,554. Both of the two latter methods of manufacturing use procedures that utilize PRONASE (*Streptomyces griseus* protease)/trypsin digestion and phenol/urea treatment. All samples were examined morphologically using TEM. Samples prepared as a suspension in water for injection (1 mg/mL w/v) were prefixed with 5% w/v glutaraldehyde (volume ratio: 1:1) for 1 hour. Following centrifugation (8,000×g for 10 min) the pellets were suspended in fresh 2.5% v/v glutaraldehyde and incubated overnight at 4° C. After incubation, the samples were washed with washing buffer and kept in washing buffer at 4° C. prior to further processing. After washing three times in washing buffer, the samples were pre-stained with osmium tetroxide and potassium ferrocyanide for 2 hours, washed, and dehydrated in acetone. Samples were then infiltrated with increasing concentrations of EPON™ (epoxy resin) in acetone, and polymerized at 58° C. for 48 hours. Thick sections (90-100 nm) were placed on 200-mesh copper grids, and stained with uranyl acetate followed by Reynolds lead. Samples were examined in either a JEOL JEM-2011 200 kV w/Fas TEM w/Quartz XOne Microanalytical System and a Gatan DualView 300 W 1.3 k×1 k CCD Camera or a Philips CM200 200 kV TEM equipped with an AMT 2 k×2 k CCD camera.

The results of the morphologic analysis are shown in FIG. 1. FIG. 1a shows intact *Mycobacterium phlei* (used as a reference material), FIG. 1b shows MCC prepared according to U.S. Pat. No. 6,326,357, and FIG. 1c shows MCWE prepared according to U.S. Pat. No. 5,759,554. Undisrupted *M. phlei* cells were observed as an electron dense structure, and contained very few if any cell membrane or cell wall fragments. Unexpectedly, given the differential centrifugation step used in the preparation of MCWE and MCC it was observed that their compositions were a mixture of electron dense and electron transparent structures consistent with a mixture of intact mycobacteria and cell wall fragments (estimated to be 8.5 and 3.0% of intact bacteria respectively). FIGS. 1d, 1e and 1f show that the number of intact mycobacteria in MpRNC low, medium and high respectively is controlled through the use of the manufacturing procedures in Example 3 of the present invention (estimated to be 0.0, 2.5 and 12.5% respectively).

The results of this morphological analysis demonstrate that the manufacturing process of the present invention results in a controllable intact mycobacterial cell content of MpRNC formulations.

EXAMPLE 8

Manufacturing Contaminants in Mycobacterial Cell Wall Compositions

Mycobacterial cell walls manufacturing according to U.S. Pat. No. 5,759,554 (MCWE) and U.S. Pat. No. 6,326,357 (MCC) both use proteolytic enzyme digestion (*Streptomyces griseus* protease PRONASE/bovine trypsin) in conjunction with a phenol/urea treatment step. Such a procedure could result in proteolytic enzyme and phenol contamination of the final cell wall composition, even though both of these patents teach the use of washing procedures to eliminate these and other contaminants.

In this example the phenol content/contamination of mycobacterial cell walls manufactured according to U.S. Pat. No. 5,759,554, U.S. Pat. No. 6,326,357, and MRNC manufactured according to Example 3 of the present invention was determined by HPLC. MpRNC intermediate was used as a representative example of MRNC, and it is to be realized that the manufacturing principles taught in Example 3 of the present invention are applicable to all MRNC as well as to BRNC.

Suspensions of the different mycobacterial cell wall compositions (1 mg/mL in water for injection) or appropriate phenol standards in water (0-10 µg/mL) were treated with 12 M HCl at 100° C. for 60 min. After cooling, the mycobacterial cell wall compositions or phenol standards were extracted with diethyl ether (2 mL diethyl ether/mg cell wall composition). The diethyl ether phase was removed and mixed with 0.05 M NaOH in methanol (3 mL/mg cell wall composition). After evaporation to dryness using a stream of nitrogen, the residue was dissolved in water (0.2 mL/mg mycobacterial cell wall), and 100 μL was analyzed by HPLC for phenol content. The HPLC system for analysis utilized a Waters Breeze HPLC system consisting of a 717 plus auto sampler, a Waters 1525 Binary HPLC Pump and a Waters 248L Dual wavelength absorbance detector connected to a C-18 reverse phase analytical 4.6×150 mm column (Waters, Nova-Pak C18, WAT 044375), packed with 4 μm silica (Waters Ltd., Lachine, Quebec, Canada). HPLC separations were performed at room temperature using 100 μL sample volumes and at a flow-rate of 1.0 mL/min using the following gradient elution conditions: Eluent A was water acidified with 1% acetic acid (v/v) and Eluent B was 100% acetonitrile. Eluent A was maintained at 95% for 2 min and then decreased linearly to 60% over 15 min, where it was held for 3 min. UV detection of phenol was performed at 270 nm.

For the detection of exogenous proteins, 20 mL of the different mycobacterial cell wall compositions were lyophilized for a period of 72 h. Proteins were extracted from the lyophilized mycobacterial cell wall compositions using a modified RIPA extraction buffer (1% Triton X-100, 0.5% NP-40%, 1% SDS, 150 mM NaCl, 1 mM EDTA, 10 mM Tris pH 7.5 at 4° C.). The total protein content of the extract was measured according to the Macart method (Macart and Gerbaut, 1982 Clin. Chim. Acta 122:93-101). Samples were diluted with Laemmli sample buffer (62.5 mM Tris-HCl, pH 6.8, 2% SDS, 25% glycerol, 0.01% bromophenol blue and 5% mercaptoethanol) to give a concentration of 1 mg of protein per mL. A total of 60 μL of diluted samples were loaded onto 10%-20% gradient SDS-PAGE gels (Bio-Rad, Mississauga, Ontario, Canada) and electrophoresis was carried out at room temperature at 140V for 6 h to 8 h hours. For calibration, molecular-weight standard mixtures (Bio-Rad, Mississauga, Ontario, Canada) were run in parallel with the samples. Gels were stained for protein using colloidal blue staining (Invitrogen, Carlsbad, Calif., USA) for 38 h at room temperature. Bands of interest (80, containing proteins of differing molecular weights) were excised from the gels and placed in 96-well plates and then washed with water. Tryptic digestion was performed on a MassPrep liquid handling robot (Waters, Milford, Mass., USA) according to the manufacturer's specifications. Briefly, proteins were reduced with 10 mM DTT and alkylated with 55 mM iodoacetamide. Trypsin digestion was performed using 105 mM modified porcine trypsin (Sequencing grade, Promega, Madison, Wis., USA) at 58° C. for 1 h. Digestion products were extracted using 1% formic acid, 2% acetonitrile followed by 1% formic acid, 50% acetonitrile. The recovered extracts were pooled, vacuum centrifuge dried and then suspended into 8 μL of 0.1% formic acid and 4 μL were analyzed by mass spectrometry. Peptide samples were separated by online reversed-phase (RP) nanoscale capillary liquid chromatography (nanoLC) and analyzed by electrospray mass spectrometry (ES MS/MS). The experiments were performed with a Thermo Surveyor MS pump connected to a LTQ linear ion trap mass spectrometer (ThermoFisher, San Jose, Calif., USA) equipped with a nanoelectrospray ion source (ThermoFisher). Peptide separation took place on a PicoFrit column BioBasic C18, 10 cm×0.075 mm internal diameter, (New Objective, Woburn, Mass.) with a linear gradient from 2-50% solvent B (acetonitrile, 0.1% formic acid) in 30 min, at 200 mL/min (obtained by flow-splitting). Mass spectra were acquired using a data dependent acquisition mode using Xcalibur software version 2.0. Each full scan mass spectrum (400 to 2000 m/z) was followed by collision-induced dissociation of the seven most intense ions. The dynamic exclusion (30 second exclusion duration) function was enabled, and the relative collisional fragmentation energy was set to 35%. All MS/MS samples were analyzed using Mascot (Matrix Science, London, UK; version 2.2.0). Mascot was set up to search the Uniref100 database assuming the digestion enzyme was trypsin. Mascot was searched with a fragment ion mass tolerance of 0.50 Da and a parent ion tolerance of 2.0 Da. Iodoacetamide derivative of cysteine was specified as a fixed modification and oxidation of methionine was specified as a variable modification. Two missed tryptic digestion cleavage sites were allowed. Scaffold (Proteome Software Inc., Portland, Oreg.) was used to validate MS/MS based peptide and protein identifications. Peptide identifications were accepted if they could be established at greater than 95.0% probability as specified by the Peptide Prophet algorithm (Keller, A et al Anal. Chem. 2002; 74(20):5383-92). Protein identifications were accepted if they could be established at greater than 95.0% probability and contained at least 2 identified peptides. Protein probabilities were assigned by the Protein Prophet algorithm (Nesvizhskii, A I Anal Chem. 2003 Sep. 1; 75(17):4646-58). Proteins that contained similar peptides and could not be differentiated based on MS/MS analysis alone were grouped to generate the least number of proteins.

The results obtained (Table 8) show that both MCWE and MCC are contaminated with phenol and the protease aminopeptidase, a major proteolytic enzyme found in the PRONASE of *Streptomyces griseus*. MpRNC manufactured as described in Example 3, Table 7, did not contain phenol or any detectable PRONASE (*Streptomyces griseus* protease) components.

TABLE 8

Phenol, PRONASE (*Streptomyces griseus* protease) and trypsin contamination of mycobacterial cell wall compositions

| Mycobacterial cell wall composition | Phenol, ppm (ng/mg cell wall) | *Streptomyces griseus* PRONASE (aminoptidase protein) (aminopeptidase)* |
|---|---|---|
| MCWE U.S. Pat. No. 5,759,554 | 652.53 | YES |
| MCC U.S. Pat. No. 6,326,357 | 657.89 | YES |
| MpRNC Example 3, present invention | 0.00 | NO |

The data in Table 8 demonstrate that the use of phenol in the manufacture of mycobacterial cell walls leads to a detectable phenol and exogenous protein (PRONASE (*Streptomyces griseus* protease) aminopeptidase) contamination that in the case of MCWE and MCC was comparable. One advantage of using the manufacturing procedures of the present invention whereby only RNase-free water for injection is used in obtaining MRNC compositions is that the resulting compositions are free of phenol and exogenous protein contamination.

Phenol is amphiphilic and its subsequent presence in the mycobacterial cell walls is consistent with localization in the hydrophobic regions of the mycobacterial cell wall (covalently linked mycolic acids), where it remains trapped in spite of repeated centrifugation-based washes.

Analysis of contaminating proteins in MCWE and MCC, specifically *Streptomyces griseus* aminopeptidase, were positive, thus confirming that the enzymatic treatment used in the preparation of mycobacterial cell walls results in the presence of exogenous and potentially immunogenic proteins.

EXAMPLE 9

Nucleic Acid Content and Profile of MpRNC Compositions Determined by Electrophoresis MpRNC intermediate was used as a representative example of MRNC, and it is to be realized that analyses taught in this example are applicable to all MRNC and BRNC compositions.

MpRNC Intermediate suspension in water for injection collected before and after heat treatment (121° C., 30 min) was analyzed electrophoretically for its nucleic acid profile using the Bioanalyzer system (Bioanalyzer model #2100, Agilent, Santa Clara, Calif., USA). The nucleic acid fraction was obtained as described in Example 6. The nucleic acid fraction was diluted to a concentration of 30 ng/µL. Electrophoretic analysis of the length of the extracted nucleic acid was accomplished with the Bioanalyzer electrophoresis unit using the RNA 6000 nano kit (Agilent #5067-1511). This kit provides information on the quality of RNA ranged from 25 to 6000 nucleotides. MpRNC Intermediate following autoclaving was then further analyzed using the Small RNA Kit (Agilent Technologies Canada Inc., St. Laurent, Québec, Canada, kit #5067-1548), which is designed for the analysis of small nucleic acids in the size range of 6 to 150 nucleotides. MpRNC High and MpRNC Low were also analyzed after heat treatment (121° C., 30 min) using the Small RNA kit (Agilent). The results of the different electrophoretic analyses are shown in FIG. 2a and FIG. 2b.

FIG. 2a demonstrates that MpRNC Intermediate prior to autoclaving possesses a nucleic acid profile of between approximately 25 bases and close to 4000 bases when analyzed using the RNA nano 6000 kit. The result demonstrates that the use of high-pressure homogenization steps (different pressurization and number of cycles) to prepare MpRNC Intermediate results in a composition that contains a polyribonucleotide chain length of 25-4000 bases. Following autoclaving, MpRNC Intermediate shows a more compact nucleic distribution ranged between 25 bases and 200 bases (FIG. 2b). Further analysis using the Small RNA Kit demonstrated, in contrast to the profile obtained from the preparation prior to autoclaving, that all MpRNC preparations (High, Intermediate and Low) possess a nucleic acid profile that is comparable (FIG. 2b) but that differs in quantity (High>Intermediate>Low).

FIG. 2b demonstrates that MpRNC Intermediate possess an oligoribonucleotide peak that is maximal between 20-40 bases, and with a nucleic acid profile of between 5 and 60 bases in length. The MpRNC compositions had only minor amounts of nucleic acid material eluting at 100 bases, and even less oligoribonucleotide material eluting at about 150 bases in length. The results demonstrate that the use of high-pressure homogenization and heat treatment steps (different pressurization and number of cycles along with heat treatment) to prepare MpRNC results in a composition that contains an oligoribonucleotide and polyribonucleotide chain length of less than 60 bases. Comparable nucleic acid profiles are also observed in MpRNC Low and MpRNC High (FIG. 2b).

EXAMPLE 10

Analysis of Nucleic Acids in *Mycobacterium phlei* and MpRNC Compositions

In this example the nucleic acid content of *Mycobacterium phlei* and MpRNC compositions (high-, low- and intermediate-) were determined. MpRNC compositions were prepared as described in Example 3. It is to be realized that in this example MpRNC is used as an illustrative and representative example of the nucleic acid content of MRNC.

Nucleic acids were extracted from the respective compositions using the following procedure. An aliquot of the respective composition (700 µL at a concentration of 1 mg/ml) was digested with DNase- and RNase-free lysozyme, followed by inactivation and further digestion with DNase- and RNase-free proteinase K (both from Sigma-Aldrich Canada, Oakville, Ontario). Nucleic acids were extracted by phenol/chloroform/isoamyl alcohol (25:24:1 v/v), and precipitated by the addition of glycogen, sodium acetate and ethanol. The precipitates were washed with 80% ice-cold ethanol, and solubilized in 50 µL at distilled water. The concentration was determined by measurement of the absorbance at 260/280 nm in a UV spectrophotometer. The nucleic acid content of each composition is shown in Table 9.

TABLE 9

Nucleic acid content of MpRNC

| Composition | Nucleic acid content, ng/mg |
| --- | --- |
| *Mycobacterium phlei* | 44,786 |
| MpRNC Low | 2,683 |
| MpRNC Intermediate | 4,470 |
| MpRNC High | 15,686 |

These results demonstrate that an increasing amount of intact mycobacteria cells in MpRNC (e.g. MpRNC high) is associated with an increasing amount of nucleic acids in the MpRNC composition. The results also show that the nucleic acid content of MpRNC (2,683-15,686 ng/mg) is significantly different to that of intact *Mycobacterium phlei* (44,786 ng/mg).

EXAMPLE 11

Determination of the DNA to RNA Ratio in MpRNC and Autoclaved *Mycobacterium phlei*

MpRNC compositions were used as representative examples of MRNC, and it is to be realized that analyses taught in this example are applicable to all MRNC and BRNC compositions.

Analysis of the DNA to RNA ratio of MpRNC High, MpRNC Intermediate and MpRNC Low prepared as in Example 3 as well as autoclaved *Mycobacterium phlei* cells (prepared as described in Example 1) was first performed using enzymatic digestion with RNase-A of the extracted nucleic acids followed by Bioanalyzer 2100 electrophoresis profiling and oligoribonucleotide content quantification by using the Agilent Small RNA Kit (kit #5067-1548).

RNase-A digestion of the extracted nucleic acids (1260 ng/µL in RNase buffer) was carried out using DNase-free Ribonuclease A (RNAse-A, treated at 100° C. for 30 min to remove DNase activity) (0.1 µg enzyme, 2 h at 37° C.). The RNAse-A was obtained from Ameresco (Solon, Ohio, USA). A sample (20 ng/µL) of RNase A-treated nucleic acid was analyzed using the Bioanalyzer. The amount of DNA and RNA was determined in MpRNC High, MpRNC Intermediate and MpRNC Low as well as intact autoclaved *Mycobacterium phlei* cells using the equation:

DNA content=(Total Nucleic Acid Content−Nucleic Acid Content after RNase-A treatment).

The results of the Bioanalyzer analysis are shown in FIG. 3a for MpRNC High, FIG. 3b for MpRNC Intermediate, 3c for MpRNC Low and 3d for autoclaved *Mycobacterium phlei* whole cells. The results of the analysis of MpRNC (high-, low- and intermediate-) with respect to RNA and DNA content are shown in Table 10.

TABLE 10

DNA and RNA content of MpRNC compositions

| Composition | DNA content (% total nucleic acid) | RNA content (% total nucleic acid |
|---|---|---|
| MpRNC Low | 0 | 100 |
| MpRNC Intermediate | 0.24 | 99.76 |
| MpRNC High | 3.6 | 96.4 |
| Autoclaved *Mycobacterium phlei* | 4.0 | 96.0 |

Second, analysis of the nucleic acid content and DNA to RNA ratio of the MpRNC's of the present invention (Low, Intermediate and High) was performed using a more sensitive quantitative methods as follows: The nucleic acid fraction obtained in Example 6 was recovered by ultrafiltration using a Microsep 1K unit (molecular weight cutoff=1000 Da, Pall® Life Sciences, Ann Arbor, Mich., USA). The nucleic acid solution was then digested to a mixture of nucleoside 5'-monophosphates using nuclease P1 (Sigma-Aldrich, Oakville, ON, Canada) following the procedure reported by Liang (Liang et al., Ann. Chim. Acta 2009, 650:106-110). To ensure optimal nuclease P1 digestion, a total of 50 µL of the nucleic acid aqueous solutions to be investigated were heated in a water bath at 95-100° C. for 10 min, followed by immediate chilling on ice. Nuclease P1 was prepared at 5 units/µL in 30 mM sodium acetate buffer containing 0.5 mM $ZnCl_2$, pH 5.3. For enzymatic digestion, 50 µL of nucleic acid in aqueous solution was mixed with the same volume of nuclease P1 solution and then incubated at 50° C. for 30 min. The resulting mixture was cooled to room temperature and filtered through a Nanosep 10K filter by centrifugation at 10,000 g for 20 min at room temperature prior to HPLC analysis.

Serial dilutions of a mixture of mononucleotide standards (deoxyribo- and ribonucleotides, Sigma-Aldrich) containing 100, 10, 5, 2.5, 1 ng/µL each of the mononucleotide present in DNA and RNA were also treated to nuclease P1 treatment and filtered for use as standards in HPLC analysis. The elution order of these nucleotides was confirmed by comparing the retention time of individual nucleotides under the same HPLC condition. HPLC analysis was performed using a 1200 series HPLC system (Agilent, St-Laurent, Quebec, Canada), which was equipped with a quaternary pump with degasser, an auto sampler, a column heater, and a multi-wavelength UV detector. A ZORBAX Bonus-RP (reverse phase) column (Agilent Technologies) was used and the mobile phases comprised a linear gradient of 10 mM potassium phosphate buffer, pH 7.2 and methanol (0-10% methanol). The mononucleotides were detected at 260 nm.

The DNA:RNA ratio was determined after quantification of DNA and RNA deoxyribonucleotides and ribonucleotides (Table 11).

TABLE 11

Quantity and DNA/RNA ratio in MpRNC High, MpRNC Intermediate and MpRNC Low

| Sample | DNA ng/mg | RNA ng/mg | Total ng/mg | DNA:RNA ratio |
|---|---|---|---|---|
| MpRNC High | 969.9 | 1241.3 | 2211.2 | 0.78 |
| MpRNC Intermediate | 907.1 | 542.6 | 1449.7 | 1.67 |
| MpRNC Low | 649.7 | 309.5 | 959.2 | 2.10 |

These results demonstrate that in going from MpRNC high to MpRNC low there is an overall decrease in the nucleic acid content of ~50%, consistent with a reduced intact *Mycobacterium phlei* cell content. All MpRNC compositions in this analysis possessed both DNA and RNA, with the ratio in MpRNC intermediate and MpRNC low being comparable. These data are consistent with whole mycobacterial cell nucleic acid being removed in going from MpRNC high to MpRNC low, such that RNA in MpRNC is cell wall-bound and therefore optimally active with respect to biological activity.

EXAMPLE 12

RNA and DNA Proportions of MpRNC, MbRNC, MsRNC and MvRNC

Mycobacterial RNC compositions were analyzed electrophoretically for their RNA:DNA ratio using denaturing polyacrylamide gel electrophoresis (PAGE). It is to be understood that the mycobacteria used in this example are used as representatives for mycobacteria in general. MRNC from *Mycobacterium phlei*, *Mycobacterium bovis* strain BCG, *Mycobacterium smegmatis* and *Mycobacterium vaccae* was prepared as described in Examples 3 and 4. The nucleic acid fraction was prepared as described in Example 6. The nucleic acid fraction (50 µL) was divided into two aliquots of 25 µL each. One aliquot was treated with 10 µg of RNase A (Amresco, Solon, Ohio, USA) and the other was treated with water for injection (Wisent, RNase and DNase-free) at 37° C. for 2 hours before loading onto a pre-run denatured urea-PAGE gel at 25V/cm for 2.5 hour. The gel was stained with SYBRGold® solution (Invitrogen) diluted 10,000× in 1× Tris borate buffer (89 mM Tris, 89 mM boric acid, 2 mM EDTA, pH 8.0) for 15 min before being visualized by UV at a wavelength of 312 nm. The gel image was digitized using ImageJ image processing and analysis software from the NIH (Bethesda, Md., USA). The results are shown in FIG. 4. The size distribution of the nucleic acids demonstrated by denaturing PAGE electrophoresis (FIG. 4a) was confirmed by microfluidic chip RNA analysis as described in example 11 for *Mycobacterium phlei* RNC.

The proportion of RNase-susceptible RNA is shown in FIG. 4b. The treatment of the RNA fraction of the mycobacterial RNCs with RNase A resulted in a 26.3% reduction in signal intensity for MbRNC, in a 46.1% reduction for MsRNC, in a 53% reduction for MpRNC, and a 60% reduction for *Mycobacterium smegmatis* RNC. The MRNC compositions of the present invention therefore contain RNAse-susceptible RNA.

The higher proportion of RNA in *Mycobacterium vaccae* RNC, *Mycobacterium phlei* RNC and *Mycobacterium smegmatis* RNC when compared to *Mycobacterium bovis* BCG RNC is consistent with the fact that *Mycobacterium phlei*, *Mycobacterium smegmatis* and *Mycobacterium vaccae* are all rapidly growing species when compared to *Mycobacterium bovis* BCG, and that they have a stronger ribosomal RNA expression promoter and an additional ribosomal RNA operon (Gonzalez-Y-Merchand, et al. 1997. J. Bacteriol. 179 (22): 6949-6958). Such data are consistent with an increased metabolic requirement, expressed as increased RNA levels in both the mRNA and rRNA pools of the faster-growing mycobacterial species.

EXAMPLE 13

Lipid Content of MpRNC

The lipid content of and the molecular classes present in MpRNC were determined. It is to be realized that in this example MpRNC Intermediate is used as an illustrative and representative example of the lipid content of MRNC manufactured using the procedures described in Examples 2 and 3 of the present invention. It also to be realized that different mycobacterial species have different mycolic acid profiles, but that the principles taught in this example are applicable to the family mycobacteriaceae and genus *mycobacterium*.

Cell wall compositions from mycobacteria are often treated in their preparation with solvents to remove lipids (see for example Ribi et al., 1966, J. Bacteriol., 91:975-983, where the use of petroleum ether or acetone is described). Such procedures carry the risk of solvent contamination due to solubilization of the chemicals in covalently attached and non-extractable lipid species. Lipids of mycobacteria are conventionally divided into 2 groups: those that are non-covalently bound, and that are therefore organic solvent or detergent extractable (including trehalose mono- and dimycolates and lipoproteins), and those that are covalently bound to the cell wall (mycolic acids). Unless saponification is performed, organic solvent or detergent extraction only removes non-covalently bound lipids. The impact of the manufacturing process for MpRNC described in Example 3 of the present invention to on the lipid content of MpRNC was determined.

A modification of the Dole procedure for extraction of non-covalently bound free lipids, including phospholipids, glycolipids and free fatty acids was used (Dole and Meinertz, 1960, J. Biol. Chem. 235:2595-2599, as modified by Puttmann et al., 1993 Clin. Chem. 39:825-832). One mL of MpRNC Intermediate pellet or supernatant from step 3 of the manufacturing process in Example 3 prepared from a 10 mg/mL MpRNC Intermediate suspension in water for injection and subjected to high-speed centrifugation was added to 3 mL of the solvent mixture n-heptane/isopropanol/phosphoric acid (10/40/1, v/v/v) and mixed vigorously in a glass tube with a Teflon® lined cap. The mixture was incubated at room temperature for 30 min. After adding 1 mL of n-heptane, followed by 1 mL of water, the tube was capped tightly, mixed thoroughly and was left to settle. The upper organic phase was collected and the remaining aqueous phase containing delipidated cell wall or supernatant was extracted by the addition of 1 mL of heptane. The two heptane phases, containing extractable, non-covalently attached free lipids, were then pooled and dried at 50° C. under a stream of nitrogen in a glass tube with a Teflon® lined cap until thoroughly dried. The dry lipid extracts were stored at 4° C. protected from light until derivatization. The residue containing free lipid-depleted MpRNC was collected, kept at −20° C. and used for the extraction of covalently bound lipids (defined as the covalently linked mycolic acid cell wall fraction).

The derivatization of the fatty acids for HPLC was carried out as follows. First, 0.1 mL of $KHCO_3$ solution (4 g $KHCO_3$ dissolved in 98 mL water and 98 mL methanol) was added to dry free lipid extracts and air dried at 50° C. under stream of filtered air. Then 1 mL of n-heptane and 50 µl of p-bromophenacyl-8 reagent (Pierce Chemical Co. Rockford, Ill., USA) was added, and mixed thoroughly. The Tubes were sealed and heated for 30 min at 85° C. After cooling to room temperature, the solution was clarified by adding 1 mL of an HCl (6 M)-methanol-water mixture (1:2:1), and vortexing vigorously. The tubes were left to stand for 5 min and then the organic layer collected in a glass vial and dried under stream of nitrogen. The dry p-bromophenacyl derivatized free lipids were kept at 4° C. protected from light until reverse-phase-HPLC with UV detection analysis (RP-HPLC-UV).

RP-HPLC-UV analysis of p-bromophenacyl ester derivatives of the non-covalently bound lipids and free fatty acids was carried out using a Waters Breeze HPLC system with a binary pump, and a dual wavelength absorbance UV detector (Waters Ltd., Lachine, Quebec, Canada). A 4 micron reverse phase separation column (Waters, Nova-Pak, C18 4.6 mm×150 mm) was used for analysis. The dried p-bromophenacyl-ester fatty acid derivatives were dissolved in 100 µL acetonitrile and 5 µL was injected into the column for separation using a gradient mixture of 77% acetonitrile and 23% water for 0 to 20 min: from 20 min to 25 min the concentration of acetonitrile was raised from 77% to 96% and then decreased from 96% to 77% for the last 5 min of analysis at a flow rate of 0.25 mL/min. The column temperature was at 30° C. and the peaks were detected at 254 nm. Myristic acid (C14:0) (Sigma-Aldrich, Oakville, Ontario, Canada) was used as fatty acid standard for quantification of free lipids.

The fraction from the step 3 pellet and the step 3 supernatant remaining after the extraction of non-covalently bound lipid was dried under a stream of nitrogen at 50° C., then hydrolyzed with 2 mL hydrolysis reagent (50% w/v potassium hydroxide in water and 50% methanol, 1:1, v/v) for 1 hour at 100° C. in a glass tube with a Teflon® lined cap to release covalently-bound lipid. After cooling to room temperature, 2 mL of chloroform was added followed by 1.5 mL acidification reagent (concentrated HCl/methanol (1:1, v/v)). After vigorous mixing the tubes were left to stand for 5 min for phase separation. The chloroform phase (lower phase) was recovered and transferred into a new glass tube with a Teflon®-lined cap. The remaining aqueous phase was then re-extracted with 1 mL chloroform 2 more times. The 3 chloroform phases were pooled and dried at 80° C. under a stream of nitrogen and kept at 4° C. protected from light until derivatization.

The derivatization of the hydrolyzed covalently attached fatty acids was carried out as described for the extractable lipids except chloroform was used instead of n-Heptane. Dry p-bromophenacyl derivatized fatty acids were kept at 4° C. protected from light until RP-HPLC-UV free lipid analysis.

The RP-HPLC-UV analysis p-bromophenacyl ester derivatives of the covalently attached lipids (defined as the mycolic acid fraction in this analysis) was carried out using a Waters Breeze HPLC system with a binary pump, and a dual wavelength absorbance UV detector. A 4 micron reverse phase separation column (Waters, Nova-Pak, C18 4.6 mm×150 mm) was used for separation. The dried p-bromophenacyl ester mycolic acid derivatives were dissolved in 100 µL dichloromethane, 20 µL injected into the column and detection was at 254 nm. Behenic acid (C22:0, Sigma-Aldrich) was used as an internal standard for quantification of covalently bound lipids. The column was eluted with using a methanol/dichloromethane gradient (98% methanol/2% dichloromethane to 20% methanol/80% dichloromethane over 20 min) at a flow rate of 2.5 mL/min. Behenic acid (C22:00, Sigma-Aldrich, Oakville, Ontario, Canada) was used as internal standard for quantification, and internal low and high mycolic acid standards (generally accepted as being ~C40:n and ~C110:n respectively, and originally supplied by the Corixa Corporation Seattle, Wash., USA) were used to estimate the carbon chain length of the mycolic acids in cluster 1 and cluster 2.

The results of the noncovalently-linked lipid (extractable) and covalently-linked lipid analyses for MpRNC Intermediate are shown in FIG. 5a and FIG. 5b and in Table 5. FIG. 5A shows that the bound lipids after extraction and hydrolysis are comprised of a majority of short-chain fatty acids with a carbon chain length less than C22, and that the 2 clusters of mycolic acid are present that are characteristic of *Mycobacterium phlei*. FIG. 5B shows that the hydrolysable lipid obtained after saponification is composed of both low and high molecular weight species, and that the 2 mycolic acid clusters fall between the 2 mycolic acid standards (FIG. 5b). The relationship between retention time and carbon chain length for the mycolic acid standards was determined to be linear.

Lipids peaks obtained after saponification were classified as short-chain fatty acids (defined in this analysis as the result of the breakdown of mycolic acid wax esters during hydrolysis into lower molecular weight dicarboxylic acids and an alcohol) with an elution time of 0.5-5 min, mycolic acid cluster 1 (elution time 7-9 min, comprising mycolic acids of between 45 and 55 carbons) and mycolic acid cluster 2 (elution time 10.5-13.5 min comprising mycolic acids of between 70-85 carbons). The amounts of each of these fractions in the step 3 pellet and supernatant are shown in Table 12 phase) was recovered and transferred into a new glass tube with a Teflon®-lined cap. The remaining aqueous phase was then re-extracted with 1 mL chloroform 2 more times. The 3 chloroform phases were pooled and dried at 80° C. under a stream of nitrogen and weighed. The extraction was carried out twice and the lipid content of was 14.1±5.1 mg/30 mg MCC and 9.7±0.14 mg/30 mg MpRNC Intermediate.

The presence of such a high lipid content (and low mycolic acid content) in the supernatant is consistent with the liberation of non-cell wall lipids (extractable, non-covalently-bound fatty acids and non-covalently linked mycolates) following disruption of the mycobacteria by high pressure homogenization, and which are removed from the cell wall composition by the differential high-speed centrifugations steps described in Example 3. This procedure therefore eliminates the necessity of organic solvent or detergent extraction and the risk of contamination as a means of reducing the lipid content of mycobacterial cell wall compositions. The covalently attached mycolic acids, an integral component of mycobacterial cell walls, were however conserved by the manufacturing method of Example 3, thus providing the benefit of definitive identification of cell walls from a given mycobacterial species by mycolic acid cluster analysis.

EXAMPLE 14

Diaminopimelic Acid (DAP) and Alanine Content of MpRNC High, MpRNC Intermediate, MpRNC Low and of Autoclaved *Mycobacterium phlei*

In this example the MpRNC intermediate composition was used as a representative example of MRNC, and it is to be

TABLE 12

Non-covalent and covalently-bound lipids in MpRNC Intermediate

| MpRNC prepared as in Example 2 | Extractable, non-covalently bound lipid, µg/mL | Non-extractable, covalently bound cell wall lipid (including mycolic acids), µg/mL | | Total Lipid, µg/mL) | |
|---|---|---|---|---|---|
| | | Short chain | Total mycolic acid (cluster 1 + cluster 2) | Total covalent | Total covalent + extractable |
| MpRNC (high speed centrifugation pellet) | 15.4 | 104.4 | 31.1 | 135.5 | 151.0 |
| MpRNC high speed centrifugation | 307.4 | 22.1 | 1.7 | 23.7 | 331.2 |

The high-speed centrifugation pellet of MpRNC Intermediate from step 3 of Example 3, containing MpRNC composition, contained extractable lipid, as well as covalently bound lipid. The covalently-bound lipid, considered to represented mycolic acids, represented 90% of the total lipid. The high-speed supernatant, in contrast, contained very little covalently bound lipid, with most of the lipid being non-covalently bound (93%).

In another experiment, a total of 30 mg of MpRNC Intermediate and MCC were dried under a stream of nitrogen at 50° C., then hydrolyzed with 2 mL hydrolysis reagent (50% w/v potassium hydroxide in water and 50% methanol, 1:1, v/v) for 1 hour at 100° C. in a glass tube with a Teflon® lined cap to release covalently-bound lipid. After cooling to room temperature, 2 mL of chloroform was added followed by 1.5 mL acidification reagent (concentrated HCl/methanol (1:1, v/v)). After vigorous mixing the tubes were left to stand for 5 min for phase separation. The chloroform phase (lower realized that analyses taught in this example are applicable to all MRNC, and many BRNC compositions prepared from but not limited to *Nocardia* species, *Rhodococcus* species, and *Corynebacteria* species.

Diaminopimelic acid (2,6-diaminoheptanedioic acid, DAP) and alanine (ALA) are major constituents of the peptidoglycan of *Mycobacterium phlei*. Peptidoglycan is itself a major component of mycobacterial cell walls. DAP is involved in interpeptide chain linkages, and ALA is a component of the peptide chain of peptidoglycan. The measurement of DAP and ALA content thus provides an indirect determination of the degree of intact mycobacterial cell content whereby increasing mycobacterial cell content results in a decreased DAP content. The DAP and ALA content of MpRNC High, MpRNC Intermediate MpRNC Low and autoclaved *Mycobacterium phlei* cells were determined by HPLC analysis. MpRNC High, MpRNC Intermediate, MpRNC Low and autoclaved *Mycobacterium phlei* cells were diluted in HPLC grade water to a concentration of 0.2 mg/mL. A 20 μL aliquot of each diluted sample preparation along with a respective hydrolysis blank and bovine serum albumin control were dried under vacuum in pyrolysis tubes and hydrolyzed at 165° C. for 60 min using 6M HCl vapor. DAP and ALA were derivatized with 6-aminoquiolyl-N-hydroysuccinimidyl carbamate (AQC) (AccQ Fluor Reagent kit, Waters, Milford, Mass., USA). Standard curves were prepared using synthetic and commercially available DAP and ALA. The DAP and ALA content of MpRNC High, MpRNC Intermediate, MpRNC Low and of autoclaved *Mycobacterium phlei* cells was determined using triplicate samples by HPLC (5 μL injection volume of each sample using an ACCQ-Tag Novo-Pak $C_{18}$ 4 μm, 3.9×150 mm column [Waters] and an Agilent Model 1100, Santa Clara, Calif., USA HPLC equipped with fluorescence and UV detectors). The results of the DAP and ALA content determinations are shown in Table 13.

TABLE 13

DAP and ALA content of MpRNC High, MpRNC Intermediate, MpRNC Low and autoclaved *Mycobacterium phlei*.

| Composition | ALA (mol %)* | DAP (mol %)* |
|---|---|---|
| MpRNC High | 15.8 | 2.6 |
| MpRNC Intermediate | 21.6 | 7.0 |
| MpRNC Low | 23.8 | 10.1 |
| Autoclaved *Mycobacterium phlei* | 14.8 | 2.7 |

*The results for ALA and DAP are expressed as the mol % of the amino acid analysis.

Table 13 demonstrates that with a decreasing number of intact mycobacterial cells present in MpRNC (High to Low), there is a corresponding increase in both the ALA and DAP content. The results are consistent with an increase in cell wall peptidoglycan content in the MpRNC compositions in going from MpRNC High to MpRNC Low concomitant with a decrease in intact mycobacterial cells. Table 11 and Table 13 together also show that isolation of an oligoribonucleotide/polyribonucleotide formulation composition containing cell walls is associated with increasing amounts of peptidoglycan (as determined by DAP and alanine measurements, or by alanine measurements (for those bacteria and mycobacteria that do not contain DAP) and that decreasing amounts of DAP and alanine are associated with increasing levels of intact mycobacteria. Such measurements can therefore be used to accurately verify and control the intact mycobacterial (or bacterial) content of such compositions

EXAMPLE 15

MpRNC Protein Content

In this example the MpRNC Intermediate composition was used as a representative example of MRNC, and it is to be realized that the analyses taught in this example are applicable to all MRNC and BRNC compositions.

The protein content of MpRNC Intermediate prepared as described in Example 3 of the present invention was compared with that of *Mycobacterium phlei* cells. To ensure an accurate determination of protein content the samples were prepared as 1 mg/mL suspension in water for injection and subjected to probe ultrasonication to ensure disruption of any intact mycobacteria and thus ensure an accurate determination of protein. Protein content was determined before and after sonication. *M. phlei* intact cells (grown according to Example 1 of the present invention using MCMC-C) and MpRNC Intermediate manufactured according to Example 3 of the present invention (both at a concentration of 1 mg/mL in water for injection) were subjected to probe sonication (Misonix Inc, ¼" probe, setting 8, 1-15 min on ice). Samples were removed at various times for protein analysis using the Macart method. Briefly, the protein content was determined by mixing 15 μL of appropriately *Mycobacterium phlei* or MpRNC Intermediate with 300 μL of MACART solution (L. Gerbaut and M. Macart, Clinical Chemistry (1982) 32, 353-355) in the wells of microtiter plates and incubating for 5 min at room temperature, after which the OD was determined at 630 nm using a microplate reader. The amount of protein in each sample was determined using as a reference serial dilution of bovine serum albumin (2 mg/mL Protein Standard, Sigma). The results of the analysis are shown in Table 14.

TABLE 14

Protein content of *Mycobacterium phlei* and MpRNC Intermediate

| | Protein content (μg/100 μg)* | |
|---|---|---|
| Sonication time (min) | *Mycobacterium phlei* | MpRNC Intermediate |
| 0 | 25 | 13 |
| 1 | 29 | 10 |
| 5 | 36 | 12 |
| 15 | 45 | 17 |
| Fold change (0 min-15 min) | 1.8 | 1.3 |

*Mean protein content of a triplicate analysis.

The data shown in Table 14 show that MpRNC Intermediate manufactured according to the method described in Example 3 had a significantly different protein content when compared to *Mycobacterium phlei* (13% w/v versus 45% w/v respectively), thus demonstrating that the manufacturing process results in a decrease in protein content when compared with the starting cell biomass. These data show also that without the use of an additional disruption procedure, the protein content of MpRNC was underestimated by approximately 30%. The slight increase in protein obtained after sonication of MpRNC Intermediate is consistent with the presence of 3 protein-containing compartments—cell wall fragment proteins accessible to the protein analysis reagent, proteins within cell wall fragments that are not accessible to the protein analysis reagent, and proteins within residual, intact mycobacteria, and are also not accessible to the protein analysis reagent. These proteins become accessible following disruption of the cell wall fragments or cells by sonication or other means. It is to be understood that the protein level of MpRNC Low and MpRNC Intermediate and MpRNC High will be a reflection of the ratio of intact cells to cell wall fragments in the respective formulations.

EXAMPLE 16

MpRNC Induces the Activation of the Human Pathogen-Associated Molecular Pattern Receptor (PAMP) NOD2

Nucleotide-binding oligomerization domain 2 (NOD2) is a pattern recognition receptor (PRR), one of a diverse family of receptors responsible for sensing pathogen-associated molecular patterns (PAMPs) associated with microbial pathogens or cellular stress. NOD2 is a receptor for muramyl dipeptide (MDP), known to be the minimal structure of bacterial peptidoglycan that possesses immune stimulant activity. NOD2 MDP agonists are known to activate innate immune system cells (monocytes, macrophages and dendritic cells), modulate inflammation, have analgesic activity, possess anticancer activity, possess anti-infection activity, induce the differentiation of human bone marrow CD34+ cells and increase vaccine protection through their immune adjuvant activity. MDP and a large number of analogs and derivatives have been shown to be effective agents for the treatment of cancer and infection, and can act as vaccine adjuvants.

The NOD2 activating activity of MpRNC was evaluated using HEK-293 cells engineered to express the human NOD2 receptor and a downstream signalling marker IL-8 under the control of NOD2-driven NF-κB. It is to be understood that MpRNC is used as an example of MRNC, and that the principles taught in this Example are applicable to MRNC from the mycobacteriaceae family. The ability of MpRNC Intermediate to activate NOD2 was compared with MCC prepared according to U.S. Pat. No. 6,326,357.

The human HEK293-NOD2 cell line (InvivoGen, San Diego, Calif., USA) was cultured and maintained in high glucose DMEM, supplemented with 10% fetal bovine serum (both from Wisent, St-Bruno, Québec, Canada), 100 μg/mL Normocin™ and 10 μg/mL blasticidin (both from InvivoGen) at 37° C. in a humidified atmosphere containing 5% $CO_2$. HEK293-NOD2 cells were seeded at $5\times10^5$ cells/mL in a volume of 0.2 mL in sterile 96-well flat-bottomed tissue culture microplates in the cell culture medium described above, and incubated for 48 hours with 0.625, 1.25, 2.5, 5, 10, 20, 40, 80 and 160 μg/mL MpRNC Intermediate or MCC at 37° C. in a humidified atmosphere containing 5% $CO_2$. Supernatants were collected after incubation, centrifuged at 4,000×RCF for 5 min at 4° C. to remove cells and debris and the supernatant was stored at −20° C. for analysis. Human IL-8 in the supernatant was measured after 48 hours cultivation with MpRNC Intermediate suspension by means of a commercial enzyme-linked immunosorbent assay (ELISA) from BioSource, Camarillo, Calif., USA. Data were captured from an ELISA plate reader (ELx-808IU BioTek Instruments, Winooski, Vt., USA) using the KC Junior software package (BioTek Instruments, Winooski, Vt., USA) and expressed in pg/mL of IL-8 synthesized.

Table 15 shows that MpRNC Intermediate functions in a dose-related manner as a potent NOD agonist by inducing NOD2-driven IL-8 release in a concentration-dependent manner, while MCC prepared according to U.S. Pat. No. 6,326,357 was significantly less potent as a NOD agonist, with marginal activity only being seen at the highest concentration tested.

TABLE 15

NOD2 activating activity of Mycobacterial cell wall compositions

| Composition | IL-8 (pg/mL) Cell wall concentration, μg/mL | | | | | | | | |
|---|---|---|---|---|---|---|---|---|---|
| | 0.625 | 1.25 | 2.5 | 5.0 | 10 | 20 | 40 | 80 | 160 |
| MpRNC Intermediate | 45.1 | 42.7 | 51.7 | 78.3 | 110.0 | 124.7 | 133.2 | 160.1 | 186.9 |
| MCC (U.S. Pat. No. 6,326,357) | 27.7 | 20.5 | 23.8 | 16.3 | 14.9 | 11.2 | 13.4 | 16.3 | 36.6 |

It is clear that MpRNC has significant and unexpected advantages over other mycobacterial cell wall compositions such as MCC with respect to immune stimulant activity mediated through the NOD2 receptor.

In a separate study the NOD2-activating activity of MpRNC High, MpRNC Intermediate and MpRNC Low was compared by determining the potency of MpRNC High and MpRNC Low relative to that of MpRNC Intermediate. NOD2-activating activity was determined in the dose range 0.625, 1.25, 2.5, 5, 10, 20, 40 and 80 μg/mL as described above, and relative potencies were calculated using PHARM/PCS version 4.2 software (Microcomputer Specialists, Philadelphia, Pa., USA). The results shown in Table 16 demonstrate that the NOD2 activation activity of MpRNC High and of MpRNC Low is not different to that of MpRNC Intermediate.

TABLE 16

The relative potencies of MpRNC (high, intermediate and low) for the activation of NOD2

| MpRNC | Relative potency |
|---|---|
| MpRNC Intermediate | 1.0 |
| MpRNC High | 0.9 |
| MpRNC Low | 1.1 |

These data demonstrate that the presence of variable levels of intact mycobacteria in the different MpRNC compositions has no effect on their ability to activate NOD2, and that all MpRNC compositions (High, Intermediate and Low) possess the same ability to activate this innate immune system receptor.

EXAMPLE 17

Mycobacterial RNC Induce the Activation of the Human Pathogen-Associated Molecular Pattern Receptor (PAMP) NOD2

The NOD2 activation activity of mycobacterial RNC prepared from *Mycobacterium bovis* BCG, *Mycobacterium smegmatis* and *Mycobacterium vaccae* was compared with RNC from *Mycobacterium phlei* using HEK-Blue™-NOD2 cells engineered to express the human NOD2 receptor (InvivoGen, San Diego, Calif., USA) activation of which drives the synthesis of secretory embryonic alkaline phosphate (SEAP) under the control of NOD2-driven NF-κB. Measurement of SEAP in the supernatant provides a measure of NOD2 activation.

It is to be understood that MRNC from *Mycobacterium phlei*, *Mycobacterium bovis* BCG, *Mycobacterium smegmatis* and *Mycobacterium vaccae* are used as examples representative of the mycobacteriaceae family, and that the principles taught and data shown in this Example are applicable to MRNC from other mycobacteria. The MRNC Intermediate composition from *Mycobacterium phlei* (MpRNC) were used in this example, given the demonstration of comparability of activity between MpRNC High, Intermediate and Low in Example 16.

Figure 6:
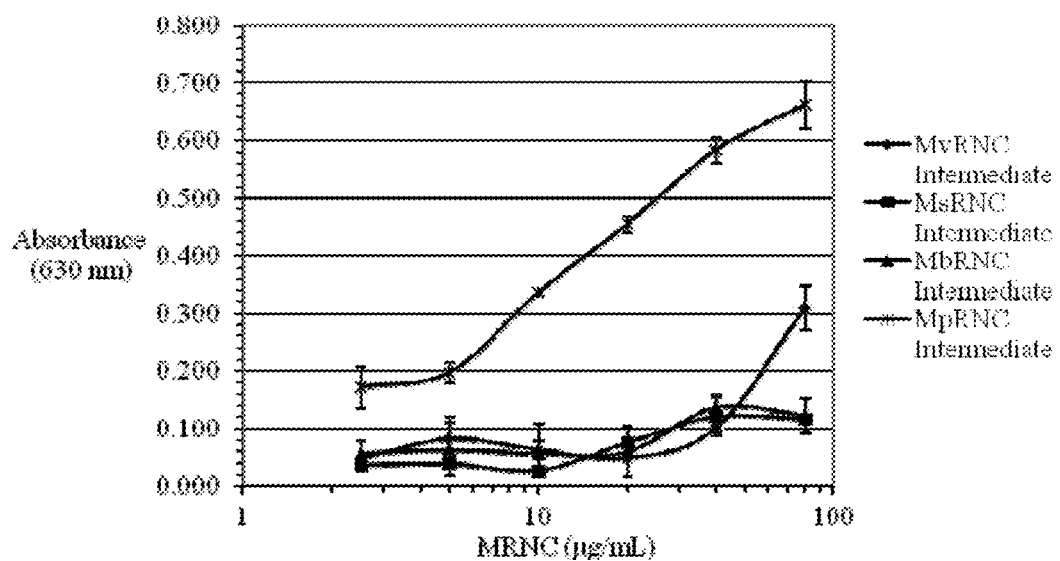
FIG. 6. NOD2 activation by mycobacterial RNC. HEK293 cells expressing NOD2 were used to determine the NOD2 agonist activity of RNC prepared from 4 mycobacterial species—*Mycobacterium phlei*, *Mycobacterium bovis* strain BCG, *Mycobacterium smegmatis*, and *Mycobacterium vaccae*. NOD2 activation results in NF-κB-driven secretory embryonic alkaline phosphatase (SEAP) induction. Following hydrolysis of the substrate by SEAP in the cell culture supernatant, enzymatic activity is expressed as the O.D. at 630 nm, and is proportional to NOD2 activation. Mean±of triplicate determinations.

The HEK293-NOD2 cell line was cultured and maintained in high glucose DMEM, supplemented with 10% fetal bovine serum (both from Wisent, St-Bruno, Québec, Canada), 30 μg/mL blasticidin, 100 μg/mL of Normocin™ and Zeocin™ (both from InvivoGen) as well as 50 U/mL penicillin and 50 μg/mL streptomycin (all from Wisent) at 37° C. in a humidified atmosphere containing 5% $CO_2$. The cells were seeded at $1\times10^5$ cells/mL in a volume of 0.2 mL in sterile 96-well flat-bottomed tissue culture microplates in the cell culture medium described above, and incubated for 72 hours with 0.625, 1.25, 2.5, 5, 10, 20, 40, and 80 μg/mL of MRNC Intermediate. Supernatants were collected for analysis after incubation, and were centrifuged at 4,000×RCF for 5 min at 4° C. to remove cells and debris. Twenty μL of supernatant was mixed with 180 μL of QUANTI-Blue™ (InvivoGen) in a 96-well flat-bottomed microtiter plates at 37° C. for 2 hours. SEAP expression was measured at 630 nm using an ELx-808IU microplate reader (BioTek Instrument, Winooski, Vt.) using the KC Junior software package (BioTek Instruments). FIG. 6 shows the dose-related activation of NOD2 by all four MRNC compositions.

All MRNC compositions demonstrated NOD2 activating activity. *Mycobacterium phlei* RNC was the most effective activator of NOD2, followed by *Mycobacterium smegmatis*, *Mycobacterium bovis* BCG and *Mycobacterium vaccae*. Both *Mycobacterium bovis* BCG and *Mycobacterium vaccae* showed marginal activation of NOD2 at the highest dose tested (80 μg/mL). The potency of the mycobacterial RNC compositions relative to *Mycobacterium phlei* RNC for the activation of NOD2 was determined using PharmPC V4.2 (Microcomputer Specialists, Philadelphia, Pa.) and is shown in Table 17.

TABLE 17

Mycobacterial RNC NOD2 activation relative to *Mycobacterium phlei* MpRNC

| Mycobacterial RNC | NOD2 potency relative to *Mycobacterium phlei* RNC |
|---|---|
| MpRNC intermediate | 1.00 |
| MbRNC intermediate | 0.014 |
| MsRNC intermediate | 0.021 |
| MvRNC intermediate | 0.013 |

EXAMPLE 18

MpRNC Induces the Activation of the Human Pathogen-Associated Molecular Pattern Receptor (PAMP) TLR2

Toll-like receptor 2 (TLR2) is a pattern recognition receptor (PRR) responsible for sensing pathogen-associated molecular patterns (PAMPs) commonly associated with microbial pathogens. Bacterial and mycobacterial cell wall structural components such as peptidoglycan, lipomannan (LM), lipoarabinomannan (LAM), lipoproteins and lipopeptides appear to be largely responsible for the activation of TLR2. It is known by those skilled in the art that TLR2 is expressed on many immune system cells, including macrophages, and that agonists of TLR2 are capable of inducing the synthesis of a number of chemokines and cytokines by such cells. The TLR2 activation activity of MpRNC Intermediate prepared as described in Example 3 of the present invention and MCC prepared according to U.S. Pat. No. 6,326,357 were compared using HEK293 cells engineered to express the human TLR2 receptor, thus providing a convenient and accepted method of determining immune stimulant potential.

It is to be understood that MpRNC Intermediate is used as an example of MRNC, and that the principles taught in this Example are applicable to MRNC from other mycobacteria, as well as to the mycobacteriaceae family.

The human HEK293-TLR2 cell line was obtained from InvivoGen, San Diego, Calif., USA. HEK293-TLR2 cells are stably transfected with the TLR2 gene and a receptor-driven secreted embryonic alkaline phosphatase gene (SEAP), placed under the control of the NF-kB gene. Activation of TLR2 thus results in the generation of alkaline phosphate activity in the cell culture medium, which is used to quantify receptor activation. The cells were cultured and maintained in high glucose DMEM, supplemented with 10% fetal bovine serum (both from Wisent, St-Bruno, Québec, Canada) and 1× Normocin™ (InvivoGen) at 37° C. in a humidified atmosphere containing 5% $CO_2$. HEK293-TLR2 cells were seeded at $5\times10^5$ cells/mL in a volume of 0.2 mL in sterile 96-well flat-bottomed tissue culture microplates in HEK-Blue™ Detection medium (InvivoGen), and incubated for 18 hours with 0.625, 1.25, 2.5, 5, 10, 20, 40, 80 and 160 μg/mL MpRNC Intermediate or MCC at 37° C. in a humidified atmosphere containing 5% $CO_2$. The HEK-Blue™ Detection medium added to the wells is designed for the detection of NF-kB induced soluble embryonic alkaline phosphatase enzyme activity (SEAP activity). After an 18 hour incubation, the optical density (which is proportional to the activation of NF-kB through TLR2 engagement) was determined at 630 nm using a microplate reader (ELx-808IU model, BioTek Instrument, Winooski, Vt., USA). Data was captured using the KC Junior software package (BioTek Instruments).

Table 18 shows the activation of TLR2 (expressed as the OD at 630 nm) and demonstrates that MpRNC Intermediate prepared using the procedure described in Example 3 has dose-related TLR2 activating activity. Determination of the potency of MpRNC Intermediate relative to MCC showed that although the activities were comparable to that of MCC prepared as described in U.S. Pat. No. 6,326,357. MpRNC Intermediate was 10.6 fold more potent than MCC as a TLR2 activator (determined using PHARM/PCS version 4.2 software, Microcomputer Specialists, Philadelphia, Pa., USA).

TABLE 18

TLR2 activating activity of MpRNC Intermediate and MCC

| | TLR2 activation (SEAP O.D.) Mycobacterial cell wall composition, μg/mL | | | | | | | | | |
|---|---|---|---|---|---|---|---|---|---|---|
| Composition | 0 | 0.625 | 1.25 | 2.5 | 5.0 | 10 | 20 | 40 | 80 | 160 |
| MpRNC Intermediate | 0.15 | 0.60 | 0.38 | 0.52 | 0.50 | 0.59 | 0.55 | 0.64 | 0.71 | 0.74 |
| MCC, U.S. Pat. No. 6,326,357 | 0.15 | 0.42 | 0.40 | 0.40 | 0.49 | 0.45 | 0.56 | 0.51 | 0.57 | 0.61 |

These data in conjunction with the data from the evaluation of the ability of MpRNC to activate NOD2 as shown in Example 16, demonstrate that MpRNC cell wall compositions possess dual agonist activity towards 2 key receptors of the innate immune system, specifically the ability to activate both NOD2 and TLR2 without resort to the use of synthetic agonists.

EXAMPLE 19

Mycobacterial RNC Induces the Activation of the Human Pathogen-Associated Molecular Pattern Receptor (PAMP) TLR2

The TLR2 activating activity of the mycobacterial RNC compositions as prepared in Example 4 was determined using the HEK-293 cell reporter system engineered to express the human TLR2 receptor and compared with *Mycobacterium phlei* RNC Intermediate.

The human HEK293-TLR2 cell line was obtained from InvivoGen, San Diego, Calif., USA. The HEK293-TLR2 cells are stably transfected with the TLR2 gene and a receptor-driven secreted embryonic alkaline phosphatase gene (SEAP), placed under the control of NF-kB. Activation of TLR2 thus results in the generation of alkaline phosphate activity in the cell culture medium, which is used to quantify receptor activation. The cells were cultured and maintained in high glucose DMEM, supplemented with 10% fetal bovine serum (both from Wisent, St-Bruno, Québec, Canada) and 1× Normocin™ (InvivoGen) at 37° C. in a humidified atmosphere containing 5% $CO_2$. HEK293-TLR2 cells were seeded at $5\times10^5$ cells/mL in a volume of 0.2 mL in sterile 96-well flat-bottomed tissue culture microplates in HEK-Blue™ Detection medium (InvivoGen), and incubated for 18 hours with 2.5, 5, 10, 20, 40, and 80 μg/mL mycobacterial RNC at 37° C. in a humidified atmosphere containing 5% $CO_2$. The HEK-Blue™ Detection medium added to the wells is designed for the detection of TLR2/NF-kB induced soluble embryonic alkaline phosphatase enzyme activity (SEAP activity). After an 18 hour incubation, the optical density (which is proportional to the activation of NF-kB through TLR2 engagement) was determined at 630 nm using a microplate reader (ELx-808IU model, BioTek Instrument, Winooski, Vt.). Data was captured using the KC Junior software package (BioTek Instruments).

Figure 7:
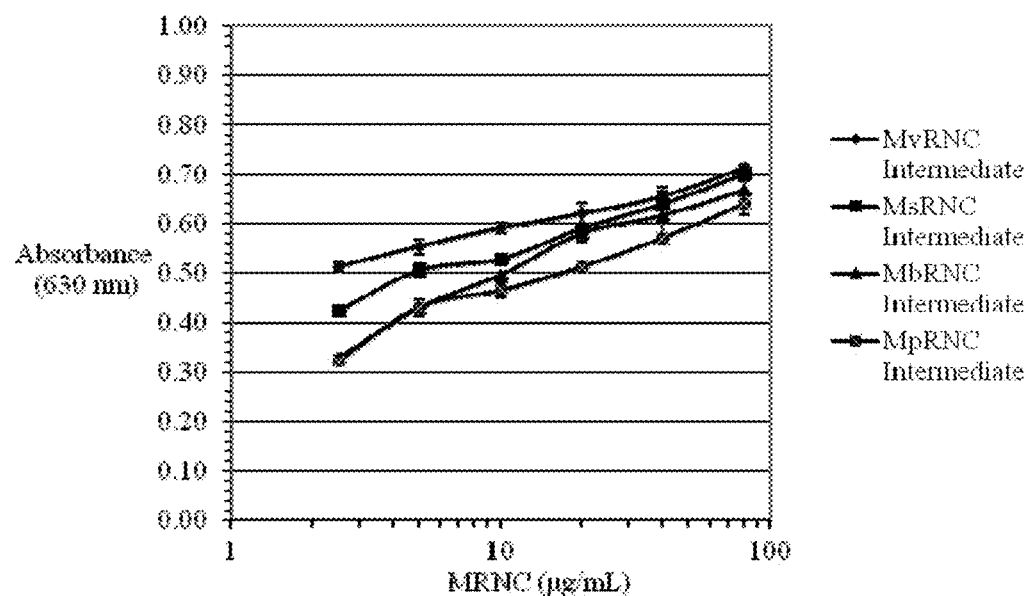
FIG. 7. TLR2 activation by mycobacterial RNC. HEK293 cells expressing the TLR2 receptor were used to determine the TLR2 agonist activity of MRNC prepared from 4 mycobacterial species—*Mycobacterium phlei*, *Mycobacterium bovis* strain BCG, *Mycobacterium smegmatis*, and *Mycobacterium vaccae*. TLR2 activation results in NF-κB-driven SEAP induction. Following hydrolysis of the substrate by SEAP in the cell culture supernatant, enzymatic activity is expressed as the O.D. at 630 nm, and is proportional to NOD2 activation. Mean±of triplicate determinations.

FIG. 7 shows that all 4 mycobacterial RNC induced the activation of TLR2 in a dose-related manner in the dose range 2.5-80 μg/mL. *Mycobacterium vaccae* RNC was the most active, followed in decreasing order of activity by *Mycobacterium smegmatis*, *Mycobacterium bovis* BCG and *Mycobacterium phlei* RNC. The potency of the mycobacterial RNC compositions relative to *Mycobacterium phlei* RNC for the activation of TLR2 was determined using PharmPC v4.2 (Microcomputer Specialists, Philadelphia, Pa., USA) and is shown in Table 19.

TABLE 19

Mycobacterial RNC TLR2 activation relative to *Mycobacterium phlei* MpRNC

| Mycobacterial RNC | TLR2 activation potency relative to *Mycobacterium phlei* RNC Intermediate |
|---|---|
| MpRNC Intermediate | 1.00 |
| MbRNC Intermediate | 1.56 |
| MsRNC Intermediate | 3.06 |
| MvRNC Intermediate | 5.86 |

The range of potencies observed for the activation of TLR2 (<6-fold difference range) indicate that all 4 mycobacterial RNC compositions have comparable TLR2 agonist activity. It is clear that one skilled in the art upon reading this and other examples in the present application (for example NOD2 activation) will make use of the most appropriate combination of immune stimulant activities and immune system receptor agonist function associated with a particular mycobacterial RNC composition in determining the applicability of a specific mycobacterial RNC or combination thereof for a particular or specific prophylactic or therapeutic application.

EXAMPLE 20

Stimulation of TLRs by MpRNC Intermediate

TLR2 agonists are generally recognized as being associated with cell wall PAMPs from Gram positive bacteria and mycobacteria. TLR3 agonists are generally recognized as double-stranded viral RNA. TLR4 agonists are generally recognized as being lipopolysaccharide. TLR5 interacts specifically with bacterial flagellin. TLR7 and TLR8 agonists are generally recognized as being single-stranded RNA. TLR9 agonists are generally recognized as being unmethylated DNA containing CpG dinucleotide sequences (CpG motif). Example 18 showed that MpRNC Intermediate stimulated TLR2. MpRNC Intermediate also contains both RNA and DNA (Example 10). The ability of MpRNC Intermediate to stimulate TLR2, TLR3, TLR4, TLR5, TLR7, TLR8 and TLR9 was therefore determined to see if the presence of RNA and DNA in MpRNC Intermediate resulted in activation of nucleic acid-specific TLRs, or of any other TLR. It is to be understood that MpRNC Intermediate is used as an example of MRNC, and that the principles taught in this Example are applicable to MRNC from the mycobacteriaceae family.

The TLR stimulating activity of MpRNC Intermediate was tested on HEK293 cells that are engineered to express one specific TLR (InvivoGen). Activation of a given TLR results in the NF-κB driven synthesis of SEAP, the enzymatic activity of which is detected in the supernatant as described in Example 19. Treatment of HEK293 cells expressing the different TLRs with MpRNC Intermediate was carried out as described in Example 18 using a final concentration of 90 μg/mL. The positive control TLR agonists used in this study are shown in Table 20, as well as the final concentration used in the assay.

TABLE 20

TLR agonist positive controls

| TLR | Agonist | Final concentration |
|---|---|---|
| TLR2 | Heat-killed *Listeria monocytogenes* | $10^8$ cells/mL |
| TLR3 | Poly(I:C) | 1.0 μg/mL |
| TLR4 | *Escherichia coli* K12 LPS | 0.1 μg/mL |
| TLR5 | *Staphylococcus typhimurium* flagellin | 0.1 μg/mL |
| TLR7 | Gardiquimod (imidazoquinoline TLR7 agonist) | 1.0 μg/mL |
| TLR8 | CLO75 (thiazoloquinolone TLR8 agonist) | 1.0 μg/mL |
| TLR9 | CpG oligonucleotide 2006 | 0.1 μg/mL |

The results of the evaluation are shown in Table 21. All of the TLR agonist controls gave positive responses. Significant stimulation of HEK293 cells expressing TLR2 was seen with MpRNC Intermediate, and although some weak stimulation of HEK293 cells expressing TLR3 or TLR5 was observed this was significantly lower than the respective positive controls, poly(I:C) and flagellin (3% and 4% of the positive control activity respectively). The apparent stimulation of TLR3 and TLR5 was subsequently shown not to be reproducible or dose-related, and not active at the concentrations of the standards, and was therefore considered to be an artifact. MpRNC Intermediate did not stimulate any other TLR, including RNA-specific TLR7 and TLR8, as well as the DNA CpG-motif specific TLR9.

TABLE 21

TLR agonist activity of MpRNC Intermediate

| HEK293 expressing TLR: | SEAP activity, OD 630 | |
|---|---|---|
| | MpRNC Intermediate* | Positive control |
| 2 | 3.787 | 3.315 |
| 3 | 0.101 | 3.212 |
| 4 | −0.001 | 2.205 |
| 5 | 0.129 | 3.231 |
| 7 | 0.042 | 2.384 |
| 8 | 0.020 | 3.446 |
| 9 | 0.026 | 2.334 |

*Mean of 4 manufactured samples tested.

Three conclusions are to be drawn from these data. First, MpRNC only activates the TLR TLR2; second the presence of RNA in MpRNC Intermediate does not result in activation of the RNA-specific TLRs TLR3, TLR7 or TLR8; and third that the presence of DNA in MpRNC Intermediate does not result in activation of the CpG receptor TLR9, demonstrating an absence of functional CpG motifs in MpRNC Intermediate.

EXAMPLE 21

Impact of Intact *Mycobacterium phlei* Cells on the Immune Stimulatory Activity of MpRNC Compositions The impact of the presence of intact *Mycobacterium phlei* cells on the immune stimulatory activity of MpRNC prepared as described in example 2 was determined using a cytokine/chemokine-induction assay. Specifically, the immune stimulant activity of MpRNC compositions containing various proportions of intact *Mycobacterium phlei* cells was determined. It is to be realized that this example is used as an illustrative and representative example of the influence of intact mycobacterial cells on the immune stimulatory activity of MRNC. It is to be understood that MpRNC is used as an example of MRNC, and that the principles taught in this Example are applicable to MRNC from the mycobacteriaceae family.

Peripheral blood mononuclear cells (PBMC) were isolated from 6 healthy individuals by density-centrifugation on Ficoll-Hypaque (GE Healthcare, Step-Anne-de-Bellevue, Québec, Canada). Anticoagulated blood (lithium salt of heparin) was centrifuged at low speed to remove platelets, and PBMC were isolated by cushion centrifugation using Ficoll-Hypaque. The isolated PBMC were washed by low-speed centrifugation (150×RCF for 10 min at 4° C.) in RPMI 1640 (Wisent Inc., St Bruno, Québec, Canada) containing 10% heat-inactivated fetal bovine serum (Wisent Inc.) and 10 µg/mL gentamycin (Sigma-Aldrich, Oakville, Ontario, Canada), and suspended at a concentration of $5 \times 10^5$ viable cells/mL medium. One mL was plated in the wells of 24-well tissue culture plates. The cells were allowed to incubate for 24 hours at 37° C. in an atmosphere of 5% $CO_2$. MpRNC Intermediate or MpRNC Intermediate containing varying amounts of heat treated *Mycobacterium phlei* cells (121° C., 30 min) were added to the tissue culture plates (final concentration 10 µg/mL for IL-10 induction, 1 µg/mL for IL-12p40 induction), and the cells incubated at 37° C. in an atmosphere of 5% $CO_2$ for a further 48 hours. The supernatants were removed, clarified by 0.2 micron membrane filtration and the levels of IL-10 and IL-12p40 determined by kit ELISA (BioSource, Camarillo, Calif., USA, catalog numbers KHC0102 and KHC0122 respectively) using the suppliers' recommended procedures.

The results are shown in FIG. 8. It can be seen that MpRNC Intermediate (containing a calculated 0.7% w/w intact mycobacteria), containing varying proportions of intact autoclaved *Mycobacterium phlei* cells (the range tested being 100% MpRNC Intermediate through to 100% intact autoclaved *Mycobacterium phlei* cells to reflect the potential levels of intact mycobacteria inherent in the new manufacturing procedures and compositions) induced IL-10 production (FIG. 8*a*) with a bell-shaped response, with the optimal proportion of intact autoclaved *Mycobacterium phlei* cells being in the range of about 5 to 30% w/w. IL-10 induction with MpRNC Intermediate containing intact autoclaved *Mycobacterium phlei* cells in the proportion of about 5-30% w/w was found to be higher than the 100% MpRNC Intermediate composition or a composition comprising 100% intact autoclaved *Mycobacterium phlei* cells.

FIG. 8*b* shows that the MpRNC Intermediate composition containing varying proportions of intact autoclaved *Mycobacterium phlei* cells (range tested: 100% MpRNC Intermediate through to 100% intact autoclaved *Mycobacterium phlei*) induced IL-12p40 production with a bell-shaped response, with the optimal proportion of intact autoclaved *Mycobacterium phlei* cells being in the range of about 10-50% w/w. IL-12 induction with MpRNC Intermediate composition containing intact autoclaved *Mycobacterium phlei* cells in the proportion of about 10 to 50% w/w was higher than a composition comprising 100% MpRNC Intermediate or a composition comprising 100% intact autoclaved *Mycobacterium phlei* cells.

Analysis of variance (ANOVA, two-way without replicates) showed that the proportion of intact *Mycobacterium phlei* cells in MpRNC significantly influenced cytokine induction ($p<0.025$ at an alpha of 0.05), and that the levels of IL-10 and IL-12 induced by MpRNC were statistically different ($p<0.05E^{-6}$ at an alpha of 0.05).

EXAMPLE 22

MpRNC Induces Chemokine and Cytokine Synthesis in Immune Effector Cells

The chemokine- and cytokine-inducing activity of MpRNC was analyzed by the use of a Milliplex® chemokine/cytokine analysis kit. It is to be understood that MpRNC is used as an example of MRNC, and that the principles taught in this Example are applicable to MRNC from the mycobacteriaceae family.

Human PBMC were isolated by Ficoll density-gradient centrifugation of whole blood (13 healthy individuals in total). PBMC were prepared in RPMI 1640 medium containing 10% v/v heat-inactivated fetal bovine serum (56° C./30 min) (both from Wisent, St-Bruno, Québec, Canada) and 50 µg/mL gentamicin sulfate (Sigma-Aldrich Canada, Oakville, Ontario, Canada). PBMC ($1 \times 10^6$ cells) were seeded in a volume of 1.0 mL in 6-well flat-bottomed microplates and incubated at 37° C./5% $CO_2$/100% humidity in the cell culture medium described above with or without (untreated controls) 160 µg/mL final concentration MpRNC Intermediate. The cytokine, chemokine and hematopoietic growth factor levels in the culture medium were measured after 48 hours incubation using a Milliplex® MAP kit for human chemokines/cytokines (Millipore Corporation, Billerica, Mass., USA) on a Bio-Plex 200 system (BioRad Laboratories, Hercules, Calif., USA). The results shown are expressed as the mean fold-increase in chemokine/cytokine levels versus untreated PBMC.

The results shown in Table 22 demonstrate that MpRNC Intermediate has the ability to stimulate a range of chemokines, cytokines and cellular growth factors from immune effector cells present in PBMC, thus demonstrating its ability to act as an immune stimulant for the induction of chemokines, cytokines and cellular growth factors.

TABLE 22

Chemokine, cytokine and cellular growth factor induction by MpRNC Intermediate

| Chemokine/Cytokine | Family | Mean ± SD fold increase versus untreated PBMC |
|---|---|---|
| G-CSF | Hematopoietic growth factor | 128.5 ± 101.4 |
| GM-CSF | Hematopoietic growth factor | 41.0 ± 27.0 |
| IL-1a (alpha) | Cytokine | 16.2 ± 9.6 |
| IL-1b (beta) | Cytokine | 116.3 ± 151.3 |
| IL-10 | Cytokine | 23.4 ± 12.5 |
| TNF-a (alpha) | Cytokine | 42.4 ± 37.3 |
| IL-6 | Cytokine | 254.6 ± 374.7 |
| MIP-1b (beta) | Chemokine | 39.2 ± 50.3 |
| MIP-1a (alpha) | Chemokine | 27.3 ± 33.9 |
| GRO | Chemokine | 36.9 ± 61.1 |
| MDC | Chemokine | 16.5 ± 26.4 |

EXAMPLE 23

Stimulation of GM-CSF, MU-CSE, M-CSF, G-CSF, SDF-1a and LIF Synthesis in Human Peripheral Blood Mononuclear Cells by MpRNC Multi-Colony Stimulating Factor (MU-CSF; also known as IL-3), which stimulates the differentiation of pluripotent hematopoietic cells into myeloid progenitor cells in addition to stimulating the production of erythrocytes, dendritic cells, granulocytes, megakaryocytes and monocytes, Macrophage Colony Stimulating Factor (M-CSF), Granulocyte-Macrophage Colony Stimulating Factor (GM-CSF), Granulocyte Colony Stimulating Factor (G-CSF), Stromal Cell Derived Factor-1alpha (SDF-1a) and Leukemia Inhibitory Factor (LIF) are human hematopoietic growth factors showing a wide range of biologic activities that include the growth promotion and cell differentiation of different types of target cells (progenitor cells), stimulation of hematopoiesis and stem cell mobilization. The ability of MpRNC Intermediate to stimulate the synthesis of these growth factors from immune cell was determined. It is to be understood that MpRNC Intermediate is used as an example of MRNC, and that the principles taught in this Example are applicable to MRNC from the mycobacteriaceae family.

Peripheral blood mononuclear cells (PBMC) were isolated from 6 healthy individuals by density-centrifugation on Ficoll-Hypaque. PBMC were incubated at $0.5 \times 10^6$ cells per mL in 6-well tissue culture plates with 1.6-160 µg/mL MpRNC Intermediate (prepared as described herein, see Tables 2 and 3) for 48 hours. Levels of MU-CSF, M-CSF, GM-CSF, G-CSF, SDF-1a and LIF were measured after 48 hours in the supernatants using a Bioplex® system (Bio-Rad, Mississauga, Ontario, Canada) with appropriate beads and antibodies using Bi-Rad or Millipore reagents. An increase of 50% in the level of the growth factor in the supernatant following treatment of the PBMC with MpRNC Intermediate versus control-treated cells (≥1.5-fold increase) was used to define a positive stimulatory effect.

Table 23 shows that MpRNC Intermediate induced a dose-related stimulation (>1.5-fold increase) in the synthesis of all the growth factors measured.

TABLE 23

Stimulation of GM-CSF, MU-CSF, M-CSF, G-CSF, SDF-1a and LIF synthesis in human PBMC by MpRNC Intermediate

| Growth factor | Fold increase in growth factor* MpRNC Intermediate (µg/mL) | | |
|---|---|---|---|
| | 1.6 | 16 | 160 |
| MU-CSF | 2.6 ± 3.6 | 3.7 ± 4.3 | 14.4 ± 7.3 |
| M-CSF | 2.0 ± 0.5 | 3.5 ± 1.2 | 5.0 ± 1.5 |
| GM-CSF | 1.0 ± 0.0 | 1.5 ± 1.5 | 24.1 ± 26.8 |
| G-CSF | 3.5 ± 3.9 | 20.9 ± 22.5 | 197.0 ± 163.6 |
| SDF-1a | 2.6 ± 1.5 | 3.8 ± 2.5 | 3.8 ± 2.7 |
| LIF | 1.5 ± 0.7 | 1.8 ± 0.8 | 3.4 ± 3.4 |

*The fold increase is expressed as the mean ± SD, n = 6

The data from Table 23 shows that MpRNC stimulates the synthesis of hematopoietic growth factors from immune cells found in peripheral blood, with the greatest fold increases being seen with GM-CSF and G-CSF, followed by the pluripotent growth factor MU-CSF. M-CSF, SDF-1a and LIF also showed increases above the defined response threshold level.

EXAMPLE 24

Stimulation of GM-CSF, MU-CSF and LIF Synthesis in Normal Human Urinary Tract Epithelial Cells by MpRNC The ability of MpRNC Intermediate to stimulate growth factor synthesis by non-immune cells was examined using human urinary bladder epithelial cells. These were used as an example of epithelial cells in general. It is to be understood that MpRNC Intermediate is used as an example of MRNC, and that the principles taught in this Example are applicable to MRNC from the mycobacteriaceae family.

The normal human urinary tract epithelial cell line SV-HUC-1 (obtained from the ATCC, Manassas, Va.) was incubated at $1.0 \times 10^5$ cells per mL tissue culture medium (as recommended by the ATCC) in 96-well tissue culture plates with 0.016-160 µg/mL final concentration MpRNC Intermediate (prepared as described in Example 3) for 48 hours. MU-CSF, M-CSF, GM-CSF, G-CSF, SDF-1a and LIF were measured after 48 hours in the supernatants using a Bioplex® system (Bio-Rad Laboratories (Canada) Inc., Mississauga, Ontario, Canada) with appropriate Milliplex® beads and antibodies (Millipore Corporation, Billerica, Mass., USA). An increase of 50% in the level of growth factor versus control-treated cells was used to identify positive stimulation following MpRNC Intermediate treatment (≥1.5-fold increase).

Table 24 shows the increase in growth factor production from normal human bladder epithelial cells following treatment with MpRNC Intermediate.

TABLE 24

Stimulation of growth factor synthesis in human SV-HUC-1 cells following treatment with MpRNC Intermediate

| Growth factor | Fold increase in growth factor MpRNC Intermediate (µg/mL) | | |
|---|---|---|---|
| | 0.016 | 1.6 | 160 |
| MU-CSF | 0.6 | 2.5 | 1.6 |
| M-CSF | 1.2 | 1.1 | 1.1 |
| GM-CSF | 1.0 | 1.0 | 4.0 |
| G-CSF | 1.0 | 1.0 | 1.0 |
| SDF-1a | 1.0 | 1.1 | 1.0 |
| LIF | 1.2 | 3.1 | 2.7 |

The data from Table 24 shows that treatment of normal human urinary tract epithelial cells with MpRNC Intermediate resulted in a dose-related stimulation of the synthesis of MU-CSF (bell-shaped response), GM-CSF and LIF (bell-shaped response), as defined by the threshold value of >1.5-fold increase

EXAMPLE 25

Stimulation of GM-CSF and MU-CSF Synthesis in Human Bladder Cancer Cells by MpRNC The ability of MpRNC Intermediate to stimulate growth factor synthesis in non-immune cells was examined using human urinary bladder cancer cells. These were used as an example of cancer cells in general. It is to be understood that MpRNC Intermediate is used as an example of MRNC, and that the principles taught in this Example are applicable to MRNC from the mycobacteriaceae family.

The human bladder cancer cell lines SV-HUC-2 and T24 (both obtained from the ATCC, Manassas, Va.) were incubated at $1.0 \times 10^5$ cells per ml in 96-well tissue culture plates (using the tissue culture medium recommended by the ATCC) with 0.016-160 µg/ml final concentration MpRNC Intermediate for 48 hours. Levels of MU-CSF, M-CSF, GM-CSF, G-CSF, SDF-1a and LIF were measured after 48 hours in the supernatants using a Bioplex® 200 system with appropriate beads and antibodies using Bio-Rad and/or Millipore reagents. An increase of 50% in the level of growth factor versus control-treated cells (≥1.5-fold increase) was used to identify positive stimulation following MpRNC Intermediate treatment.

Table 25 shows the increase in growth factor production from SV-HUC-2 cells following treatment with MpRNC Intermediate, and Table 23 shows the increase in growth factor production from T24 cells following treatment with MpRNC Intermediate.

TABLE 25

Stimulation of Growth Factor synthesis in human SV-HUC-2 cells following treatment with MpRNC

| Growth factor | Fold increase in growth factor MpRNC Intermediate (µg/mL) | | |
|---|---|---|---|
| | 0.016 | 1.6 | 160 |
| MU-CSF | 1.3 | 3.4 | 2.4 |
| M-CSF | 1.0 | 1.0 | 1.1 |
| GM-CSF | 1.0 | 1.0 | 1.9 |
| G-CSF | 1.0 | 1.0 | 1.0 |
| SDF-1a | 1.1 | 1.1 | 1.2 |
| LIF | 1.3 | 1.2 | 1.2 |

It is apparent from the data shown in Table 26 that incubation of the human bladder cancer cell line SV-HUC-2 with MpRNC Intermediate resulted in a dose-related stimulation of the synthesis of GM-CSF and MU-CSF.

TABLE 26

Stimulation of Growth Factor synthesis in human T24 cells following treatment with MpRNC

| Growth factors | Fold increase in growth factor MpRNC Intermediate (µg/mL) | | |
|---|---|---|---|
| | 0.016 | 1.6 | 160 |
| MU-CSF | 0.6 | 1.4 | 0.8 |
| M-CSF | 0.9 | 1.0 | 1.0 |
| GM-CSF | 0.9 | 1.5 | 2.0 |
| G-CSF | 1.0 | 1.0 | 1.0 |
| SDF-1a | 0.9 | 1.1 | 1.2 |
| LIF | 0.7 | 1.4 | 1.2 |

The data shown in Table 26 demonstrate that treatment of the human bladder cancer cell line T24 with MpRNC Intermediate stimulates the induction of GM-CSF synthesis in a dose-related manner (50% increase at 1.6 µg/mL MpRNC and 100% increase at 160 µg/mL MpRNC). MpRNC therefore stimulates hematopoietic growth factor synthesis from cancer cells.

EXAMPLE 26

Stimulation of Colony Stimulating Factors by MpRNC Following Intraperitoneal (IP) Administration in Mice This example serves to show that MpRNC Intermediate stimulates the production of growth factors in vivo. It is to be understood that MpRNC Intermediate is used as an example of MRNC, and that the principles taught in this Example are applicable to MRNC from the mycobacteriaceae family.

Groups of 2 female C57BL/6 mice were treated with 1.0 mg/kg body weight MpRNC Intermediate (prepared at a concentration of 1 mg/mL in water for injection as described in Example 3) via the IP route. Levels of granulocyte-monocyte colony stimulating factor (GM-CSF) and granulocyte colony stimulating factor (G-CSF) in the sera were determined using a Bioplex® system with appropriate beads and antibodies (Bio-Rad and/or Millipore reagents) 1, 4, 7 and 24 hours after injection. An increase of 50% in the level of growth factor versus control-treated mice (≥1.5-fold increase threshold level) was used to identify positive growth factor stimulation following MpRNC treatment.

Table 27 shows the increase in GM-CSF and G-CSF levels in the sera of the treated mice at various times following the injection of MpRNC Intermediate.

TABLE 27

Stimulation of GM-CSF and G-CSF synthesis following IP administration of MpRNC Intermediate to female C57BL/6 mice

| Hours post injection | Fold increase (mean ± SD)* | |
|---|---|---|
| | GM-CSF | G-CSF |
| 1 | 7.6 ± 9.3 | 16.5 ± 3.3 |
| 4 | 56.2 ± 28.6 | 307.1 ± 97.8 |
| 7 | 0.7 ± 0.5 | 296.2 ± 287.8 |
| 24 | 2.5 ± 2.1 | 50.3 ± 34.1 |

*2 mice per treatment group.

The data from Table 27 shows that MpRNC Intermediate stimulates the synthesis of GM-CSF and G-CSF in vivo, peaking at 4 hours post-treatment for GM-CSF and at 4-7 hours post-treatment for G-CSF. The results showed that there was a mean maximal 56-fold increase in GM-CSF serum levels 4 hours after MpRNC Intermediate injection when compared with control-treated mice, and a mean maximal 300-fold increase in G-CSF serum levels 4-7 hours post injection when compared with control mice. These data demonstrate that MpRNC Intermediate has immune stimulant activity (colony stimulating factor induction) in vivo following systemic administration.

EXAMPLE 27

Anti-Cancer Activity of MpRNC and Impact of Intact *Mycobacterium phlei* Cells

This example serves to show that MpRNC has anticancer activity. It is to be understood that MpRNC Intermediate is used as an example of MRNC, and that the principles taught in this example are applicable to MRNC from the mycobacteriaceae family. The impact of the presence of intact *Mycobacterium phlei* cells on the anticancer activity of MpRNC Intermediate or MpRNC Low as prepared in Example 3 (that is, using a mycobacterial RNC cell wall formulation) was determined using a cancer cell inhibition of proliferation assay. It is to be understood that this example is used as an illustrative and representative example of the influence of intact mycobacterial cells on the anticancer activity of MRNC in general.

RT4 human bladder cancer cells (ATCC, Manassas, Va., catalog #HTB-2™) were plated in DMEM culture medium supplemented with 10% heat-inactivated FBS (both from Wisent) and 10 µg/mL gentamycin (Sigma-Aldrich) at a concentration of $5\times10^5$ cells/ml in 96-well tissue culture plates (50 µL volume), and allowed to adhere to the surface of the wells overnight at a temperature of 37° C. in an atmosphere of 5% $CO_2$. Autoclaved *Mycobacterium phlei* cells (121° C., 30 min), heat-treated MpRNC intermediate or low (121° C., 30 min) or combinations of autoclaved *Mycobacterium phlei* cells mixed with autoclaved MpRNC intermediate or low in a volume of 50 µL tissue culture medium were added to the cells to give final concentrations of 0.01, 0.1, 1.0 and 10 µg/mL MpRNC. The cells were then incubated for 48 hours at 37° C. in an atmosphere of 5% $CO_2$. Anti-proliferative activity against the RT4 bladder cancer cell line was determined using an MTT ((3-(4,5-Dimethylthiazol-2-yl)-2,5-diphenyltetrazolium bromide) reduction assay. Briefly, 10 µL of an MTT solution (5 mg/mL in PBS) was added to each well after 48 hours incubation, and incubation continued for a further 4 hours. The reaction was then stopped by the addition of 100 µL isopropanol:HCl (24:1 v/v). The reduction of MTT leads to the production of formazan. Formazan was solubilized by use of a micropipette, and the optical density (O.D.) determined in a microplate reader at a wavelength of 570 nm against appropriate controls. The percentage inhibition of cell proliferation was determined using the equation:

% Inhibition=100−[(Test O.D.−Control O.D.)/Control O.D.].

The results obtained with MpRNC Low (see Example 3, Table 6; the third composition) plus controlled *Mycobacterium phlei* cell content and MpRNC Intermediate (Example 3, Table 6; the second composition) plus controlled *Mycobacterium phlei* cell content using the human bladder cancer cell line RT4 are shown in Tables 28 and 29 respectively. Potency determinations relative to *Mycobacterium phlei* were determined using PharmPC v4.2 (Microcomputer Specialists, Philadelphia, Pa., USA).

TABLE 28

Inhibition of RT4 bladder cancer cell proliferation by autoclaved MpRNC low, autoclaved *Mycobacterium phlei* or a combination of autoclaved MpRNC (low) and autoclaved *Mycobacterium phlei* in various proportions

| *Mycobacterium phlei*: MpRNC Low: | % Inhibition of proliferation Concentration, µg/mL | | | | Relative |
|---|---|---|---|---|---|
| (proportion) | 0.01 | 0.1 | 1.0 | 10 | Potency |
| 100:0 | 17.6 | 18.1 | 25.8 | 33.8 | 1 |
| 99:1 | 11.9 | 16.2 | 24.2 | 34.5 | 2.5 |
| 90:10 | 18.3 | 20.0 | 30.4 | 35.5 | 2.2 |
| 70:30 | 18.0 | 25.5 | 35.8 | 43.7 | 1 |
| 50:50 | 19.1 | 25.4 | 35.6 | 40.2 | 24.1 |
| 30:70 | 16.2 | 23.2 | 34.6 | 36.6 | 8.1 |
| 10:90 | 23.9 | 32.5 | 42.4 | 48.7 | 5.9 |
| 5:95 | 20.6 | 30.6 | 43.01 | 46.7 | 37.4 |
| 1:99 | 20.2 | 29.7 | 41.9 | 46.3 | 145. |
| 0:100 | 17.6 | 30.8 | 38.8 | 42.9 | 91.0 |

TABLE 29

Inhibition of RT-4 bladder cancer cell proliferation by MpRNC Intermediate, autoclaved *Mycobacterium phlei* or a combination of autoclaved MpRNC Intermediate and autoclaved *Mycobacterium phlei* in various proportions

| *Mycobacterium phlei*: MpRNC Intermediate | % Inhibition of proliferation Concentration, µg/mL | | | | Relative |
|---|---|---|---|---|---|
| (proportion) | 0.01 | 0.1 | 1.0 | 10 | Potency |
| 100:0 | 8.2 | 16.9 | 24.7 | 33.3 | 1 |
| 99:1 | 13.2 | 17.8 | 27.6 | 37.3 | 2.6 |
| 90:10 | 15.8 | 22.0 | 34.4 | 40.4 | 11.6 |
| 70:30 | 20.6 | 24.2 | 37.5 | 38.8 | 6.2 |
| 50:50 | 22.3 | 27.5 | 38.6 | 43.4 | 72.0 |
| 30:70 | 18.9 | 26.0 | 33.1 | 32.4 | 8.8 |
| 10:90 | 22.6 | 33.2 | 38.8 | 43.2 | 37.1 |
| 5:95 | 19.4 | 32.5 | 40.9 | 43.5 | 39.7 |
| 1:99 | 23.6 | 34.6 | 43.1 | 47.9 | 151.0 |
| 0:100 | 24.4 | 33.0 | 43.0 | 47.1 | 263.3 |

The results show that MpRNC Low and MpRNC Intermediate have anticancer activity, and that autoclaved *Mycobacterium phlei* (i.e., a preparation that comprises intact mycobacterial cells) has less anti-proliferative activity against RT4 bladder cancer cells than MpRNC containing either added *Mycobacterium phlei* equivalent to that in MpRNC low or MpRNC high. Moreover, MpRNC compositions with intact *Mycobacterium phlei* had less than optimum anti-proliferative activity. Calculation of the relative potency of MpRNC without added intact mycobacterial cells relative to MpRNC with increasing intact mycobacterial cell content demonstrated that both mycobacterial RNCs were considerably more potent than intact *Mycobacterium phlei* (91-fold and 263-fold for MpRNC Low and Intermediate respectively). The addition of intact mycobacterial cells resulted in a significant decrease in potency when 10% w/w or greater, and the optimal intact mycobacterial cell content was ≤1.0% w/w depending on the initial degree of intact mycobacterial cell content (0% for MpRNC Intermediate, and 1% for MpRNC Low. MRNC compositions and formulations intended for anticancer applications therefore benefit from a low intact mycobacterial cell content.

EXAMPLE 28

Anticancer Activity of MpRNC Intermediate Towards Lewis Lung Carcinoma

This example serves to show that MpRNC Intermediate possesses anticancer activity both in vitro and in vivo. It is to be understood that MpRNC Intermediate is used as an example of MRNC, and that the principles taught in this Example are applicable to MRNC from the mycobacteriaceae family.

The direct anticancer activity of MpRNC Intermediate manufactured according to the method of the present invention and formulated in RNase-free water was determined using the Lewis lung carcinoma (LLC) cell line. LLC cells were obtained from the ATCC (Manassas, Va., USA). LLC is used extensively in the development of chemotherapeutic and immunotherapeutic anticancer agents (see for example Kimura, Y. New Anticancer agents: In vitro and in vivo evaluation of antitumor and antimetastatic action of various compounds isolated from medicinal plants. in vivo 2005; 19:37-60). The LLC cells were maintained in DMEM medium containing 10% v/v heat-inactivated fetal bovine serum (56° C. for 30 min) (both from Wisent, St-Bruno, Québec, Canada), and 10.0 µg/mL gentamycin sulfate (Sigma-Aldrich, Oakville, Ontario, Canada) at 37° C. in an atmosphere of 5% $CO_2$. LLC cells in DMEM/10% heat-inactivated FBS without gentamycin were seeded at $4.0 \times 10^4$ cells in a volume of 0.1 mL in 96-well flat-bottomed tissue culture microplates, and MpRNC Intermediate suspension (0.1 mL) was added to triplicate wells to give final concentrations of 0.01-100.0 µg/mL. The plates were then incubated for 48 hours at 37° C. in an atmosphere of 5% $CO_2$. The antiproliferative activity of MpRNC was determined as described for the RT4 bladder cancer cell line (formazan reduction) in Example 27. The results are shown in Table 30.

TABLE 30

Inhibition of LLC cellular proliferation by MpRNC Intermediate

| | MpRNC Intermediate (µg/mL) | | | | |
|---|---|---|---|---|---|
| | 0.01 | 0.1 | 1.0 | 10 | 100 |
| % inhibition of LLC proliferation | 9.5 ± 4.9 | 23.0 ± 5.7 | 38.5 ± 9.2 | 45.0 ± 11.3 | 49.0 ± 5.7 |

The results shown are the mean ± SD of 2 experiments.

The results shown in Table 30 demonstrate that MpRNC has dose-related anticancer activity against LLC cells, as determined by measurement of inhibition of proliferation. Example 27 and this Example (Example 28) therefore demonstrate that the direct anticancer activity of MpRNC is not cancer cell type- and by extension not cancer specific.

Distant site metastases are the leading cause of cancer-associated mortality (Kim et al., Carcinoma produced factors activate myeloid cells via TLT2 to stimulate metastasis. Nature 2009; 457:102-106). Experimental liver metastases can be produced by the injection of LLC cells into the spleen (Ligo et al., Therapeutic activity and tissue distribution of ME2303, a new anthracycline containing fluorin, and its metabolites in mice bearing hepatic metastases of Lewis lung carcinoma. Anti-Cancer Drugs 1990; 1:77-82 and Alino et al Morpho-functional study of vascular fluorochrome delivery to lung and liver metastases of Lewis lung carcinoma (3LL), Tumori 1991; 77:206-211). The tumor loci induced in the liver by the intrasplenic injection of LLC cells are regarded as a model of metastatic spread to the liver, and where the number of tumor foci is increased by blocking the activity of Kupffer cells (specialized macrophages lining the sinusoids of the liver) with carrageenan. This model therefore provides a useful tool for studying different aspects of liver metastases, (Kopper et al., Experimental model for liver metastasis formation using Lewis lung tumor. J. Cancer Res and Clin. Oncol. 1982; 103:31-38). The objective of the following studies was to determine the efficacy of MpRNC suspension, following intravenous (IV) administration, as a treatment for experimental hepatic metastases induced by the intrasplenic injection of LLC cells in C57BL/6 mice.

LLC cells were maintained in DMEM medium containing 10% v/v heat-inactivated fetal bovine serum as described above. The cells were serially passaged every 3-4 days, and were used at passage 2-3. The cells were harvested, by trypsinization (4 min at 37° C.), washed twice in DMEM medium without fetal bovine serum and gentamycin sulfate, centrifuged at 250×g for 5 min at 4° C. and the cell pellet suspended in DMEM medium without fetal bovine serum and gentamycin sulfate. The number of cells was adjusted to the required concentration after cell viability was determined using trypan blue exclusion and counting in a hemacytometer. The cells were kept on ice until intrasplenic injection.

Female C57BL/6 mice, 10-12 weeks of age, were obtained from Charles River Laboratories Ltd., St. Constant, Québec, Canada. This mouse strain is syngeneic for LLC cells. Hepatic metastases were induced by the intrasplenic injection, under general anesthesia, of LLC cells ($1.0-3.0 \times 10^5$ LLC cells in a volume of 100 µL). The spleen was excised after cancer cell injection. The effect of treating the mice prior to LLC injection (prophylactic treatment) or after LLC cell injection (therapeutic treatment) was firstly examined. MpRNC Intermediate was injected 1 day before (prophylactic regimen), on days 2, 5, 7, 9 and 12 (therapeutic regimen), or on days −1, 2, 45, 7, 9 and 12 (prophylactic and therapeutic regimen) following LLC cell injection using groups of 10 mice. MpRNC Intermediate formulated in RNase-free water for injection as described in Example 3 was administered in a dose volume of 100 µL, corresponding to a dose of 5 mg/kg body weight. The number of hepatic metastases was determined on day 15 following LLC cell injection. The results (Table 31) show that the therapeutic+prophylactic administration protocol was the most effective treatment regimen, followed by the prophylactic treatment regimen, and that the therapeutic treatment regimen was the least effective. Thus a combination of prophylactic and therapeutic therapy is the most effective for the treatment of hepatic LLC metastases.

TABLE 31

Treatment of experimental LLC hepatic metastases by MpRNC Intermediate

| | Group 1: Untreated | Group 2: MpRNC Intermediate Prophylactic | Group 3: MpRNC Intermediate Therapeutic | Group 4: MpRNC Intermediate Prophylactic + Therapeutic |
|---|---|---|---|---|
| Mean number of tumors | 26 | 11 | 21 | 6 |

These data demonstrate that the use of MRNC Intermediate as a stand alone therapy or in neoadjuvant and adjuvant settings for the treatment of cancer would be beneficial in reducing tumors resulting from the metastasis of primary carcinoma. The results shown in Table 31 are consistent with activation of host-defense mechanisms in the target organ prior to exposure to cancer cells (prophylactic activity), thus resulting in decreased tumor cell seeding in the liver, as well as a therapeutic effect on the cancer cells following their initial implantation in the target organ (therapeutic activity). The demonstration of direct anticancer towards LLC cell targets demonstrated in Table 30 supports such a mode of action.

A second study was conducted to determine the effect of MpRNC Intermediate suspension treatment on LLC hepatic metastases using the prophylactic/therapeutic regimen in a larger number of animals. Experimental LLC hepatic metastases were established as described above using groups of 20 mice, and prophylactic/therapeutic treatment with MpRNC Intermediate at a dose of 5 mg/kg body weight carried out.

The results of this study showed that there were 141±72 (mean±SD) metastases in the control group, and that by using a prophylactic and therapeutic treatment protocol as described above, MpRNC Intermediate treatment significantly reduced the number of metastases to 62±41 (mean±SD, p<0.0002, Mann-Whitney U-test), thus demonstrating a significant anticancer activity in vivo against experimentally-induced hepatic metastases. The anticancer activity demonstrated against LLC cells in vitro is therefore confirmed as a predictive measure of the inhibitory effect against the development of hepatic metastases in vivo.

EXAMPLE 29

Anti-Cancer Activity of Mycobacterial RNC

This example serves to show that MRNC possess anticancer activity. It is to be understood that the principles taught in this Example are applicable to MRNC from the mycobacteriaceae family.

The anticancer activity of the mycobacterial RNC as prepared in Example 3 and 4 was determined using an inhibition of cancer cell proliferation assay. Those of skill in the art recognize that such studies are known to be predictive of anticancer activity in vivo. In this example, bladder cancer cell lines were used as being representative of cancer cell lines in general, and it is to be understood that one skilled in the art will immediately appreciate that anticancer activity studies using such cancer cell lines can be readily extrapolated to other cancer cell lines.

A total of four human bladder cancer cells were used in the example, and all were obtained from the ATCC (Manassas, Va., USA). Cultivation of the cell lines was carried out as recommended by the ATCC. Details of the bladder cancer cell lines are shown in Table 32.

TABLE 32

Bladder cancer cell line characteristics

| Cell Line | ATCC/E CACC NO. | Ethnicity/ Sex/Age | Molecular characteristics | Reference |
|---|---|---|---|---|
| HT-1376 Transitional, Grade-III | CRL-1472 | Caucasian/ F/58 yrs | Mutated p53 & p21, lack of pRb expression | Rasheed et al. 1977. JNCI 58: 881. |
| RT4 Papilloma, Benign | HTB-2 | Caucasian/ M/63 yrs | WT p53 & p21 | Rigby & Franks. 1970. Br. J. Cancer 24: 746. |
| SCaBER Squamous, Grade unknown | HTB-3 | African/ M/58 yrs | No expression of pRb, mutated p53 | O'Toole et al. 1976. Int. J. Cancer. 17: 707. |
| SW780 Transitional, Grade-I | CRL-2169 | Caucasian/ F/80 yrs | N/A | Kyriazis et al. 1986. Cancer Res. 44: 3997. |

Bladder cancer line cells were plated in DMEM culture medium supplemented with 10% heat-inactivated FBS (both from Wisent) and 10 µg/mL gentamycin (Sigma-Aldrich) at a concentration of $5\times10^5$ cells/ml in 96-well tissue culture plates (50 µL volume), and allowed to adhere to the surface of the wells overnight at a temperature of 37° C. in an atmosphere of 5% $CO_2$. Mycobacterial RNC Intermediate prepared as described in Example 3 and Example 4 in a volume of 50 µL tissue culture medium was added to the cells to give final concentrations of 0.0016, 0.016, 0.16, 1.6, 16, and 80 µg/mL MpRNC. The cells were then incubated for 48 hours at 37° C. in an atmosphere of 5% $CO_2$. Anti-proliferative activity was determined using an MTT ((3-(4,5-Dimethylthiazol-2-yl)-2,5-diphenyltetrazolium bromide) reduction assay. Briefly, 10 µL of an MTT solution (5 mg/mL in PBS) was added to each well after 48 hours incubation, and incubation continued for a further 4 hours. The reaction was then stopped by the addition of 100 µL isopropanol:HCl (24:1 v/v). The reduction of MTT leads to the production of formazan. Formazan was solubilized by use of a micropipette, and the optical density (O.D.) determined using ELx-808IU microplate reader (BioTek Instrument, Winooski, Vt., USA) using the KC Junior software package (BioTek Instruments) at a wavelength of 570 nm against appropriate controls. The percent inhibition of cancer cell proliferation was determined using the equation:

% Inhibition=100−[(Test O.D.−Control O.D.)/Control O.D.].

The potency of the MRNC compositions was determined using PharmPC v4.2 (Computer Associates, Philadelphia, Pa.)

The results obtained with the MRNC using the four human bladder cancer cell lines are shown in Table 33. All MRNC compositions demonstrated dose-dependent anti-proliferative activity against the bladder cancer cell lines. MbRNC from *Mycobacterium bovis* strain BCG was the least effective, demonstrating dose-related anti-proliferative activity, with ~20-40% inhibition (depending on the bladder cancer cell line) at the highest dose tested. All of the other MRNC demonstrated dose-related anti-proliferative activity, with ~35-70% inhibition (depending on the bladder cancer cell line) at the highest dose tested. For this reason the potency of the different MRNC relative to MRNC from *Mycobacterium bovis* strain BCG was determined, and the results are shown in Table 33.

TABLE 33

Antiproliferative potency of MRNC relative to *Mycobacterium bovis* BCG MbRNC

| Mycobacterial RNC | Potency relative to *Mycobacterium bovis* BCG MbRNC | | | | Mean potency, 4 cancer cell lines (±SD) |
|---|---|---|---|---|---|
| | HT1376 | RT4 | ScaBER | SW780 | |
| MbRNC Intermediate | 1 | 1 | 1 | 1 | 1 |
| MpRNC Intermediate | 716.00 | 1430.00 | 7590 | 6220 | 3987 ± 3428 |
| MsRNC Intermediate | 214.00 | 145.00 | 637 | 1530 | 631 ± 635 |
| MvRNC Intermediate | 4190.00 | 1170.00 | 11900 | 9890 | 6794 ± 4978 |

The most potent MRNC for inhibition of bladder cancer proliferation was that obtained from *Mycobacterium vaccae*, followed in decreasing order of potency by MpRNC from *Mycobacterium phlei*, MsRNC from *Mycobacterium smegmatis*, and MbRNC from *Mycobacterium bovis* strain BCG. The magnitude of and the order of potency for the mycobacterial RNC compositions was maintained for all 4 bladder cancer cell lines, irrespective of their origin (low-grade, high-grade) or mutational status, with *Mycobacterium vaccae* MvRNC and *Mycobacterium phlei* MpRNC being some ~6800-fold and ~4000-fold more potent respectively than *Mycobacterium bovis* BCG MbRNC.

It is to be realized that this example teaches three important principles. Firstly, MRNC prepared from disparate mycobacterial species (pathogenic, non-pathogenic, fast-growing, slow growing) possess anticancer activity, and thus such activity is therefore applicable to MRNC prepared from member species of the mycobacteriaceae family. Secondly, the mutational status of the cancer cell target does not appear to play a role in determining the anticancer activity. In fact, significant anticancer activity is seen with cancer cell lines possessing known treatment resistant genotypes (p53 and p21 mutations) and MDR phenotypes (for example HT1376). Those skilled in the art know that such mutations and resistance phenotypes are characteristic of cancer in general, and are not restricted to bladder cancer cells, and will appreciate that the anticancer activity of MRNC is therefore applicable to many other cancer types. Thirdly, MRNC prepared from three fast-growing mycobacterial species is more effective than MRNC prepared from a slow growing mycobacterial species such as *Mycobacterium bovis* strain BCG.

EXAMPLE 30

Preparation of *Mycobacterium avium* Subspecies *paratuberculosis* RNA-Containing Composition (MapRNC) and Determination of Anticancer Activity In this example, intact *Mycobacterium avium* subspecies *paratuberculosis* cells are first washed by low-speed centrifugation to remove culture medium components, and are then disrupted using high-pressure homogenization with an Avestin EmulsiFlex-05 high-pressure homogenizer as described in Example 3. After high-pressure homogenization the remaining intact mycobacteria are removed by differential centrifugation using relative centrifugal forces that are optimized for the controlled removal of any residual, intact and undisrupted *mycobacterium*. The mycobacterial cell depleted fraction, comprising nucleic acids of the *mycobacterium* associated with mycobacterial cell wall fragments and the desired and controlled amounts of intact mycobacterial cells for optimal anticancer activity, is further purified by centrifugation washing at a higher relative centrifugal force, to remove soluble contaminants. The MapRNC is isolated as a pellet following centrifugation washing at high relative centrifugal force. The MapRNC is then heat-treated at 121° C. for between 5-30 min. The anticancer activity of MapRNC is determined using cancer cell lines representative of the major cancer cell types as described in Examples 8 and 9. The results show that heat-treated MapRNC has dose-related anti-proliferative activity against cancer cell lines and against hepatic metastases.

EXAMPLE 31

Anti-Cancer Activity of Total RNA of *Mycobacterium phlei*

The biological activity of a total RNA preparation from *Mycobacterium phlei* cells was determined using a cancer cell proliferation assay. The RNA was prepared using the Trizol reagent (Invitrogen, Carlsbad, Calif., USA) according to the manufacturer's instruction following cell lysis in FastRNA Blue-Tubes (Bio-101 Inc.) using a FastPrep FP120 bead-beater apparatus (Savant, Thermo-Fisher, Nepean, ON, Canada) for 1 min at level 4.5. The RNA preparation was then treated with 'DNA-free' reagent to remove residual genomic DNA according to the manufacturer's instruction (Ambion, Austin, Tex., USA). RT4 (ATCC catalog #HTB-2) and HT1376 human bladder cancer cells (ATCC catalog #CRL-1472) were plated in DMEM culture medium supplemented with 10% FBS (both from Wisent) and 10 µg/ml gentamycin (Sigma-Aldrich) at a concentration of $2\times10^5$ cells/ml in 96-well tissue culture plates (50 µL volume), and allowed to adhere to the surface of the wells overnight at a temperature of 37° C. in an atmosphere of 5% $CO_2$. Total RNA in a volume of 50 µL tissue culture medium was added to the cells to give final concentrations of 0.01, 0.1, 1.0 µg/mL of RNA. The cells were then incubated for 72 hours at 37° C. in an atmosphere of 5% $CO_2$. Anti-proliferative activity against the cancer cell lines was determined using an MTT ((3-(4,5-Dimethylthiazol-2-yl)-2,5-diphenyltetrazolium bromide) reduction assay. Briefly, 10 µL of an MTT solution (5 mg/mL in PBS) was added to each well after 72 hours incubation, and incubation continued for a further 4 hours. The reaction was then stopped by the addition of 100 µL isopropanol:HCl (24:1 v/v). The reduction of MTT leads to the production of formazan. Formazan was solubilized by use of a micropipette, and the optical density (O.D.) determined in a microplate reader at a wavelength of 570 nm against appropriate controls. The percentage inhibition of cell proliferation was determined using the equation:

% Inhibition=100−[(Test O.D.−Control O.D.)/Control O.D.].

The results show a moderate anti-cancer activity of total RNA of *Mycobacterium phlei* against HT1376 with inhibitory activity of 2.2%, 7.1% and 6.8% at 0.1 µg/mL, 1.0 µg/mL and 10.0 µg/mL RNA respectively, and slightly more inhibitory activity against RT4 with an inhibition of proliferation of 3.1%, 7.6% and 18.6% at 0.1 µg/mL, 1.0 µg/mL and 10.0 µg/mL RNA respectively. When compared to the results obtained in Example 27 or Example 29, where the mycobacterial RNA was in the form of oligoribonucleotides and polyribonucleotides formulated with a mycobacterial cell wall, it is clear that there are distinct and unexpected advantages to be obtained with respect to biological activity when using a mycobacterial cell wall RNA composition (or other pharmaceutically acceptable carriers such as chitosan or cationic liposomes).

EXAMPLE 32

Determination of the Integrated Potency Index of Mycobacterial Cell Wall RNC

Mycobacterial cell wall RNCs (MRNCs) of the present invention have the ability to stimulate the immune system through 2 distinct receptor systems and to inhibit cancer cell division, and are thus trifunctional therapeutic compositions. Using the data from Examples 29, 17 and 19 (anti-proliferative potency, NOD2 activation potency and TLR2 activation potency respectively), an Integrated Potency Index for MpRNC Intermediate, MsRNC Intermediate and MvRNC Intermediate relative to MbRNC Intermediate was determined as a means of integrating the overall anticancer and immune stimulant activities. Because of the wide range of numerical values for the relative potencies between the different assays (≥3 magnitudes), a natural logarithm (log) transformation was used in this determination, and the values for each activity summed. MbRNC was assigned a potency of 1, and the potency of the other MRNC determined relative to MbRNC. It is to be understood that the natural log of 1 is 0. The results are shown in Table 34.

TABLE 34

Integrated Potency Index of MRNC Intermediate.

| MRNC Intermediate | Anti-proliferative potency (natural log) | NOD2 potency (natural log) | TLR2 potency (natural log) | Integrated Potency Index (natural log) |
|---|---|---|---|---|
| MbRNC | 0 | 0 | 0 | 0 |
| MpRNC | 8.29 | 4.25 | −0.45 | 12.09 |
| MsRNC | 6.45 | −0.09 | 0.67 | 7.30 |
| MvRNC | 8.82 | 0.37 | 1.32 | 10.52 |

It is clear that while all MRNC had similar, comparable potencies with respect to TLR2 activation, MpRNC, MsRNC and MvRNC were all more potent than MbRNC with respect to anticancer activity. MpNAC however was the most potent MRNC with respect to NOD2 activation. Determination of the Integrated Potency Index showed that MpRNC has the highest overall potency, followed by, in descending order, MvRNC, MsRNC and MbRNC.

EXAMPLE 33

Preparation of MpRNC Compositions with Controlled Amounts of Intact Mycobacterial Cells for Immune Stimulation MpRNC is conveniently prepared with controlled amounts of intact autoclaved mycobacteria by preparing MpRNC Low (as detailed in Example 2 and Example 3) and adding intact autoclaved mycobacterial cells to MpRNC to give the desired proportion optimal for the induction of immune responses. Generally, the inventors have found that the optimal proportion of intact *Mycobacterium phlei* cells needed to induce an immune response is within the range of about 5-50% by weight, with such proportions giving rise to optimal immune stimulatory activity.

EXAMPLE 34

Preparation of MRNC Compositions with Controlled Amounts of Intact Mycobacterial Cells for Immune Stimulation MRNC is conveniently prepared from a given mycobacterial species of the mycobacteriaceae family such as but limited to *Mycobacterium bovis* strain BCG, *Mycobacterium avium* substrain *paratuberculosis, Mycobacterium smegmatis* or *Mycobacterium vaccae*, by preparing MRNC Low (as described in Example 3 for MpRNC) and adding intact autoclaved mycobacterial cells to MRNC to give the desired proportion optimal for the induction of immune responses. Generally, the inventors have found that the optimal proportion of intact mycobacterial cells needed to induce an immune response is within the range of about 5-50% by weight, with such proportions giving rise to optimal immune stimulatory activity.

EXAMPLE 35

Treatment of MpRNC with Ribonuclease-A

Treatment of MpRNC with ribonuclease (for example, the enzymatic digestion conditions described in Example 10) results in a significant reduction in the amount of RNA contained within an MRNC or MpRNC composition. Such reductions significantly reduce the ability of MRNC or MpRNC to act as therapeutic agents.

MpRNC Intermediate was made as described in Example 3 except that before the final two cycles of high-pressure homogenization, the washed MpRNC Intermediate pellet was resuspended in water for injection with or without RNase A (Sigma, final concentration 10 μg/mL; MpRNC-RNase and MpRNC-Control respectively) for 3 hours at 37° C. The MpRNCs were then washed by high-speed centrifugation to remove RNase A and resuspended in water for injection at a concentration of 1 mg/mL. The suspensions were subsequently homogenized and terminally sterilized. The anticancer activity of MpRNC-RNase and MpRNC Control was determined using the bladder cancer cell lines HT1376 and RT-4 as described in Example 27. The relative potency of the two MpRNC formulations was calculated from the linear part of the dose-response curve using PharmPC v4.2 (Microcomputer Specialists, Philadelphia, Pa., USA).

Both MpRNC formulations inhibited the proliferation of HT1376 and RT-4 bladder cancer cells in a dose-related manner (Table 35 and 36 respectively). RNase treatment however resulted in a reduction in the anti-proliferative activity of MpRNC towards both bladder cancer cell lines.

TABLE 35

RNase treatment reduces the anti-proliferative activity of MpRNC towards HT1376 bladder cancer cells

| MpRNC concentration | % Inhibition | |
|---|---|---|
| (μg/mL) | MpRNC-Control | MpRNC-RNase treated |
| 0 | 0.00 | 0.00 |
| 0.0016 | 14.29 | 8.51 |
| 0.016 | 15.51 | 10.97 |
| 0.16 | 25.99 | 16.31 |
| 1.6 | 45.71 | 37.52 |
| 16 | 56.60 | 50.65 |

TABLE 36

RNase treatment reduces the anti-proliferative activity of MpRNC towards RT-4 bladder cancer cells

| MpRNC concentration | % Inhibition | |
|---|---|---|
| (μg/mL) | MpRNC-Control | MpRNC-RNase treated |
| 0 | 0.00 | 0.00 |
| 0.0016 | 11.05 | 1.47 |
| 0.016 | 16.94 | 7.83 |
| 0.16 | 27.90 | 14.87 |
| 1.6 | 43.39 | 36.20 |
| 16 | 49.82 | 42.86 |

The anti-proliferative potency of MpRNC Intermediate-RNase treated relative to MpRNC Intermediate-Control treated against HT-1376 and RT-4 bladder cancer cell lines is shown in Table 37.

TABLE 37

RNase treatment reduces the anticancer potency of MpRNC Intermediate

| Bladder cancer cell line | Potency of RNase-treated MpRNC relative to MpRNC |
|---|---|
| HT1376 | 0.25 |
| RT-4 | 0.14 |

Removal of RNA in MpRNC Intermediate as a result of RNase treatment resulted in a considerable reduction in anticancer potency (4-fold and 7-fold for HT1376 and RT-4 bladder cancer cells respectively), thus demonstrating that preservation of the RNA in MpRNC is a requirement for optimal anticancer activity.

EXAMPLE 36

Formulation of BRNC, MRNC, MpRNC, MbRNC, MsRNC, MapRNC and MvRNC with Cationic Liposomes and Determination of Anticancer Activity All of the following procedures are conducted under sterile aseptic conditions. BRNC, MRNC, MpRNC, MbRNC, MsRNC, MapRNC and MvRNC are prepared by disruption of intact bacteria, mycobacteria or M. phlei using high-pressure homogenization, removal of undisrupted bacteria, mycobacteria or M. phlei by centrifugation at low RCF, and extraction of the RNC composition using phenol/chloroform/isoamyl alcohol and ethanol precipitation. The extracted RNA in the RNC composition are reduced in chain length by heat treatment at 121° C. for 5 min to prepare oligoribonucleotides and polyribonucleotides containing between approximately 20-40 bases. Cationic liposomes composed of 1,2-dioleoyl-sn-glycero-3-phosphoethanolamine/1,2-dioleoyl-3-trimethylammonium-propane (DOPE/DOTAP) in the molar ratio 1:1 are prepared by dissolving the phospholipid and cationic lipid in anhydrous chloroform (1 mg/mL) followed by rotary evaporation under reduced pressure in round-bottomed flasks to form a thin phospholipid/lipid film. Control liposomes are prepared by adding the required volume of NaCl (0.85% w/v) to the thin phospholipid/lipid film, and agitating at 65° C. to form liposomes. Cationic liposomes containing BRNC, MRNC, MpRNC, MbRNC, MsRNC, MapRNC and MvRNC are prepared by adding a NaCl solution containing BRNC, MRNC, MpRNC, MbRNC, MsRNC, MapRNC and MvRNC at a concentration of 0.1 mg/mL to the thin phospholipid/lipid film, and agitating at 65° C. to form liposomes. The cationic liposomes containing BRNC, MRNC, MpRNC, MbRNC, MsRNC, MapRNC and MvRNC will have a mean diameter of approximately 825 nm and ζ-potential of approximately +36 mV. The murine B16 melanoma inhibition of proliferation assay is carried-out as described in example 27, using a liposomal BRNC, MRNC, MpRNC, MbRNC, MsRNC, MapRNC and MvRNC concentration range of 0.01 to 10 µg/mL. Control incubations are conducted using the corresponding concentrations of control cationic liposomes or of non-liposomal BRNC, MRNC, MpRNC, MbRNC, MsRNC, MapRNC and MvRNC. MTT reduction is carried-out as described in example 27, and the amount of inhibition of cell proliferation determined. The results show that cationic liposomes containing BRNC, MRNC, MpRNC, MbRNC, MsRNC, MapRNC and MvRNC inhibit the proliferation of B16 melanoma cells in a dose-dependent manner, and that the cationic liposomes alone have no inhibitory activity. The inhibitory activity of the cationic liposomes containing BRNC, MRNC, MpRNC, MbRNC, MsRNC, MapRNC and MvRNC is significantly greater than BRNC, MRNC, MpRNC, MbRNC, MsRNC, MapRNC and MvRNC alone. These data demonstrate that a cationic liposome formulation acts as a pharmaceutical delivery system for BRNC, MRNC, MpRNC, MbRNC, MsRNC, MapRNC and MvRNC.

It is to be understood that RNA may be isolated from gram-negative and gram-positive bacteria, and from mycobacteria, Mycobacterium phlei, Mycobacterium bovis BCG, Mycobacterium smegmatis, Mycobacterium avium subspecies paratuberculosis and Mycobacterium vaccae, and formulated with the cationic liposomes as described in this example without adding the cell walls from these species.

It is to be realized that B16 melanoma cells are used in this example as being representative of a typical cancer cell, and that cationic liposomes are used in this example as a as a typical pharmaceutical delivery system for NA, and that one skilled in the art will appreciate the applicability using such types of pharmaceutical delivery systems and formulations in the treatment of cancer in general.

EXAMPLE 37

Formulation of BRNC, MRNC, MRNC, MbRNC, MsRNC, MapRNC and MvRNC with Chitosan Nanoparticles and Determination of Anticancer Activity All of the following procedures are conducted under sterile aseptic conditions. BRNC, MRNC, MpRNC, MbRNC, MsRNC, MapRNC and MvRNC are prepared by disrupting of intact bacteria, mycobacteria or M. phlei using high-pressure homogenization, removing undisrupted bacteria, mycobacteria or M. phlei by centrifugation at low RCF, and extracting the RNA using phenol/chloroform/isoamyl alcohol and ethanol precipitation. The extracted RNA is reduced in chain length by autoclaving at 121° C. for 5 min to prepare oligoribonucleotides and polyribonucleotides containing between approximately 20-40 bases. Chitosan nanoparticles are prepared by mixing equal volumes of tripolyphosphate (0.5 mg/mL in water) and chitosan (average molecular weight 500,000, concentration 1 mg/mL in water) for 2 min at 20° C. to form control chitosan nanoparticles or by mixing equal volumes of bacterial, mycobacterial or M. phlei oligoribonucleotides and polyribonucleotides (BRNC, MRNC, MpRNC, MbRNC, MsRNC, MapRNC and MvRNC, 0.5 mg/mL in water) and chitosan (average molecular weight 500,000, concentration 1 mg/mL in water) for 2 min at 20° C. The incorporation of BRNC, MRNC, MpRNC, MbRNC, MsRNC, MapRNC and MvRNC in the chitosan nanoparticles is 100%. The chitosan nanoparticles are washed by centrifugation and their size and ζ-potential (an indirect measure of the particle surface charge) determined. The chitosan nanoparticles have a size in the range of approximately 200 to 1000 nm and ζ-potential of approximately −20 to −35 mV. B16 melanoma cells are grown to confluence in MEM supplemented with MEM none-essential amino acids, gentamycin (50 µg/mL) and 10% v/v heat-inactivated fetal serum at 37° C. and 5% $CO_2$. The cells are harvested by trypsinization, resuspended in MEM tissue culture medium and plated in the wells of tissue culture plates (96 well plates, 100 µL containing $5 \times 10^3$ cells) and allowed to adhere for 3 hours at 37° C. in 5% $CO_2$. Chitosan nanoparticles containing BRNC, MRNC, MpRNC, MbRNC, MsRNC, MapRNC and MvRNC are then added to the B16 melanoma cells (ATCC) to give a final concentration of BRNC, MRNC, MpRNC, MbRNC, MsRNC, MapRNC and MvRNC in the range 0.001 to 100 µg/mL. Control chitosan nanoparticles or BRNC, MRNC, MpRNC, MbRNC, MsRNC, MapRNC and MvRNC without chitosan nanoparticles are added to the B16 melanoma cells to give concentrations comparable to the BRNC, MRNC, MpRNC, MbRNC, MsRNC, MapRNC and MvRNC chitosan nanoparticles. The murine B16 melanoma cells are incubated for 48 hours at 37° C./5% $CO_2$, and the cell growth over this time determined using an MTT reduction assay. The level of reduced MTT, which corresponds to the number of viable cells, is determined at 570 nm using an ELISA plate reader. The results show that chitosan nanoparticles containing BRNC, MRNC, MpRNC, MbRNC, MsRNC, MapRNC and MvRNC inhibit the proliferation of B16 melanoma cells in a dose-dependent manner, that the chitosan nanoparticles alone have no inhibitory activity, and that the inhibitory activity of the chitosan nanoparticles containing BRNC, MRNC, MpRNC, MbRNC, MsRNC, MapRNC and MvRNC is significantly greater than BRNC, MRNC, MpRNC, MbRNC, MsRNC, MapRNC and MvRNC alone. These data demonstrate that a chitosan nanoparticle formulation acts as a pharmaceutical delivery system for BRNC, MRNC, MpRNC, MbRNC, MsRNC, MapRNC and MvRNC.

It is to be understood that RNA may be isolated from gram-negative and gram-positive bacteria, and from mycobacteria, *Mycobacterium phlei, Mycobacterium bovis* BCG, *Mycobacterium smegmatis, Mycobacterium avium* subspecies *paratuberculosis* and *Mycobacterium vaccae*, and formulated with the chitosan nanoparticles as described in this example without adding the cell walls from these species.

It is to be realized that B16 melanoma cells are used in this example of a typical cancer cell, and that chitosan nanoparticles are used in this example as a typical pharmaceutical delivery system for NA, and that one skilled in the art will appreciate the applicability using such types of pharmaceutical delivery systems and formulations in the treatment of cancer in general.

EXAMPLE 38

Preparation of *Mycobacterium avium* Subspecies *Paratuberculosis* RNA-Containing Composition (MapRNC)

In this example, intact *Mycobacterium avium* subspecies *paratuberculosis* cells are first washed by low-speed centrifugation to remove culture medium components, and are then disrupted using high-pressure homogenization with an Avestin EmulsiFlex-C5 high-pressure homogenizer. After high-pressure homogenization the remaining intact mycobacteria are removed by differential centrifugation using relative centrifugal forces that are optimized for the controlled removal of any residual, intact and undisrupted *mycobacterium*. The mycobacterial cell depleted fraction, comprising nucleic acids of the *mycobacterium* associated with mycobacterial cell wall fragments and the desired and controlled amounts of intact mycobacterial cells, is further purified by centrifugation washing at a higher relative centrifugal force, to remove soluble contaminants. The mycobacterial cell-depleted fraction is isolated as a pellet following centrifugation washing at high relative centrifugal force. The mycobacterial cell-depleted fraction is then heat-treated at 121° C. for between 5-30 min and used as mycobacterial RNC from *Mycobacterium avium paratuberculosis* (MapRNC).

EXAMPLE 39

Analysis of Nucleic Acids in MapRNC

In this example the nucleic acid type, oligoribonucleotide chain length and content of MapRNC are determined. MapRNC is prepared as described in Example 38. Nucleic acids are extracted using the following procedure. An aliquot of 700 μL at a concentration of 1 mg/ml is digested with DNase- and RNase-free lysozyme, followed by inactivation and further digestion with DNase- and RNase-free proteinase K (both from Sigma-Aldrich Canada, Oakville, Ontario). Nucleic acids are extracted by phenol/chloroform/isoamyl alcohol (25:24:1 v/v), and precipitated by the addition of glycogen, sodium acetate and ethanol. The precipitates are washed with 80% ice-cold ethanol, and resuspended in 50 μL distilled water. The concentration is determined by measurement of the absorbance at 260/280 nm in a UV spectrophotometer. The nucleic acid content of each composition is determined.

MapRNC preparations collected before and after heat-treatment (121° C., 30 min) are analyzed electrophoretically for their nucleic acid profile using the Bioanalyzer system (Bioanalyzer model #2100, Agilent, Santa Clara, Calif., USA). The nucleic acid fraction is diluted to a concentration of 30 ng/μL. Electrophoretic analysis of the length of the extracted nucleic acid is accomplished with the Bioanalyzer electrophoresis unit using the RNA 6000 nano kit (Agilent #5067-1511). This kit provides information on the quality of RNA in a size range of from 25 to 6000 nucleotides. MapRNC following autoclaving is then further analyzed using the Small RNA Kit (Agilent Technologies Canada Inc., St. Laurent, Québec, Canada, kit #5067-1548), which is designed for the analysis of small nucleic acids in the size range of 6 to 150 nucleotides. MapRNC prior to heat-treatment possesses a nucleic acid profile of between approximately 25 bases and close to 4000 bases when analyzed using the RNA nano 6000 kit. The result demonstrates that the use of high-pressure homogenization steps (different pressurization and number of cycles) to prepare MapRNC results in a composition that contains a polyribonucleotide chain length of 25-4000 bases. Following heat-treatment, MapRNC shows a more compact distribution. MapRNC possesses an oligoribonucleotide peak that is maximal between 20-40 bases, and with a nucleic acid profile of between 5 and 60 bases in length. The MapRNC compositions have only minor amounts of nucleic acid eluting at 100 bases, and even less oligoribonucleotide material eluting at about 150 bases in length. The results demonstrate that the use of high-pressure homogenization and heat treatment steps (different pressurization and number of cycles along with autoclaving) to prepare MapRNC results in a composition that contains an oligoribonucleotide and polyribonucleotide chain length of less than 60 bases.

Analysis of the DNA to RNA ratio of MapRNC prepared as in Example 38 is first performed using enzymatic digestion with RNase-A of the extracted nucleic acids followed by Bioanalyzer 2100 electrophoresis profiling and oligoribonucleotide content quantification by using the Agilent Small RNA Kit (kit #5067-1548). RNase-A digestion of the extracted nucleic acids is carried out using DNase-free Ribonuclease A (RNase A, treated at 100° C. for 30 min to remove DNase activity) (0.1 μg enzyme, 2 h at 37° C.). The RNase A is obtained from Ameresco (Solon, Ohio, USA). A sample (20 ng/μL) of RNase A-treated nucleic acid is analyzed using the Bioanalyzer. The amount of DNA and RNA is determined in MapRNC using the equation:

DNA content=(Total Nucleic Acid Content−Nucleic Acid Content after RNase-A treatment). The analysis of MapRNC shows that the presence of DNA and RNA in the extract of MapRNC.

Analysis of the DNA to RNA ratio of MapRNC of the present invention is performed as follows. The nucleic acid fraction is recovered by ultrafiltration using a Microsep 1K unit (molecular weight cutoff=1000 Da, Pall® Life Sciences, Ann Arbor, Mich., USA). The nucleic acid solution is then digested to a mixture of nucleoside 5'-monophosphates using nuclease P1 (Sigma-Aldrich, Oakville, ON, Canada) following the procedure reported by Liang (Liang et al., Ann. Chim. Acta 2009, 650:106-110). To ensure optimal nuclease P1 digestion, a total of 50 μL of the nucleic acid aqueous solutions to be investigated are heated in a water bath at 95-100° C. for 10 min, followed by immediate chilling on ice. Nuclease P1 is prepared at 5 units/μL in 30 mM sodium acetate buffer containing 0.5 mM $ZnCl_2$, pH 5.3. For enzymatic digestion, 50 μL of nucleic acid in aqueous solution is mixed with the same volume of nuclease P1 solution and then incubated at 50° C. for 30 min. The resulting mixture is cooled to room temperature and filtered through a Nanosep 10K filter by centrifugation at 10,000 g for 20 min at room temperature prior to HPLC analysis.

Serial dilutions of a mixture of mononucleotide standards (5'-deoxyribonucleotides and 5'-ribonucleotides, Sigma-Aldrich) containing 100, 10, 5, 2.5, 1 ng/μL each of the mononucleotide present in DNA and RNA are also treated to nuclease P1 treatment and filtered for use as standards in HPLC analysis. The elution order of these nucleotides is confirmed by comparing the retention time of individual nucleotides under the same HPLC condition. HPLC analysis is performed using a 1200 series HPLC system (Agilent, St-Laurent, Quebec, Canada), which is equipped with a quaternary pump with degasser, an autosampler, a column heater, and a multi-wavelength UV detector. A ZORBAX Bonus-RP (reverse phase) column (Agilent Technologies) is used and the mobile phases comprised a linear gradient of 10 mM potassium phosphate buffer, pH 7.2 and methanol (0-10% methanol). The mononucleotides are detected at 260 nm. The DNA:RNA ratio is determined after determination of DNA and RNA content. The result demonstrates that RNA is present in MapRNC in addition to DNA.

EXAMPLE 40

MapRNC Induces the Activation of the Human Pathogen-Associated Molecular Pattern Receptor (PAMP) NOD2

The NOD2 activation activity of MapRNC as prepared in Example 38 is evaluated using HEK-293 cells engineered to express the human NOD2 receptor driving NF-κB and a downstream signalling marker IL-8.

The human HEK293-NOD2 cell line (InvivoGen, San Diego, Calif., USA) is cultured and maintained in high glucose DMEM, supplemented with 10% fetal bovine serum (both from Wisent, St-Bruno, Québec, Canada), 100 μg/mL Normocin™ and 10 μg/mL blasticidin (both from InvivoGen) at 37° C. in a humidified atmosphere containing 5% $CO_2$. HEK293-NOD2 cells are seeded at $5 \times 10^5$ cells/mL in a volume of 0.2 mL in sterile 96-well flat-bottomed tissue culture microplates in the cell culture medium described above, and incubated for 48 hours with 0.625, 1.25, 2.5, 5, 10, 20, 40, 80 and 160 μg/mL MapRNC at 37° C. in a humidified atmosphere containing 5% $CO_2$. Supernatants are collected after incubation, centrifuged at 4,000×RCF for 5 min at 4° C. to remove cells and debris and the supernatant is stored at −20° C. for analysis. Human IL-8 in the supernatant is measured in the supernatants after 48 hours cultivation with MapRNC by means of a commercial enzyme-linked immunosorbent assay (ELISA) from BioSource, Camarillo, Calif., USA. Data are captured from an ELISA plate reader (ELx-808IU Bio Tek Instruments, Winooski, Vt., USA) using the KC Junior software package (Bio Tek Instruments, Winooski, Vt., USA) and expressed in pg/mL of IL-8 synthesized. MapRNC induces the synthesis and excretion of IL-8 in a dose-dependent manner. The result therefore shows that MapRNC functions as a NOD2 agonist by inducing NOD2-driven IL-8 release in a dose-dependent manner.

EXAMPLE 41

MapRNC has Human TLR2 Activation Activity

The TLR2 activation activity of MapRNC as prepared in Example 38 is measured using HEK-293 cells engineered to express the human TLR2 receptor.

The human HEK293-TLR2 cell line is obtained from InvivoGen, San Diego, Calif., USA. The HEK293-TLR2 cells are stably transfected with the TLR2 gene and a TLR2 receptor-driven secreted embryonic alkaline phosphatase gene (SEAP), placed under the control of the NF-κB gene. Activation of TLR2 thus results in the generation of alkaline phosphate activity in the cell culture medium, which is used to quantify receptor activation. The cells are cultured and maintained in high glucose DMEM, supplemented with 10% fetal bovine serum (both from Wisent, St-Bruno, Québec, Canada) and 1× Normocin™ (InvivoGen) at 37° C. in a humidified atmosphere containing 5% $CO_2$. HEK293-TLR2 cells are seeded at $5 \times 10^5$ cells/mL in a volume of 0.2 mL in sterile 96-well flat-bottomed tissue culture microplates in HEK-Blue™ Detection medium (InvivoGen), and incubated for 18 hours with 0.625, 1.25, 2.5, 5, 10, 20, 40, 80 and 160 μg/mL MapRNC at 37° C. in a humidified atmosphere containing 5% $CO_2$. The HEK-Blue™ Detection medium added to the wells is designed for the detection of NF-kB induced soluble embryonic alkaline phosphatase enzyme activity (SEAP activity). After an 18 hour incubation, the optical density (which is proportional to the activation of NF-kB through TLR2 engagement) is determined at 630 nm using a microplate spectrophotometer reader (ELx-808IU model, Bio Tek Instrument, Winooski, Vt., USA). Data is captured using the KC Junior software package (Bio Tek Instruments). SEAP activity in the cell supernatant is increased in a dose-related manner following MapRNC treatment. The results therefore show that MapRNC is capable of activating TLR2 in a dose-dependent manner (i.e., MapRNC acts as a TLR2 agonist).

EXAMPLE 42

Anti-Cancer Activity of MapRNC

The anticancer activity of MapRNC as prepared in Example 38 is determined using cancer cell lines representative of the major cancer cell types. RT4 human bladder cancer cells (ATCC catalog #HTB-2™) are plated in DMEM culture medium and CT26 murine colon cancer cell lines (ATCC catalog #CRL-2638™) in RPMI 1640 medium both supplemented with 10% heat-inactivated FBS (both from Wisent) and 10 μg/mL gentamycin (Sigma-Aldrich) at a concentration of $5 \times 10^5$ cells/mL in 96-well tissue culture plates (50 μL volume), and allowed to adhere to the surface of the wells overnight at a temperature of 37° C. in an atmosphere of 5% $CO_2$ prior to treatment. Human leukemia cell Jurkat (ATCC TIB-152™) is suspended in DMEM culture medium supplemented with 10% heat-inactivated FBS and 10 µg/mL gentamycin at a concentration of $1 \times 10^6$ cells/mL in 96-well tissue culture plates (50 µL volume). Heat-treated MapRNC (for example 121° C., 30 min) in a volume of 50 µL tissue culture medium is added to the cells to give final concentrations of 0.01, 0.1, 1.0 and 10 µg/mL MapRNC. The cells are then incubated for 48 hours at 37° C. in an atmosphere of 5% $CO_2$. Anti-proliferative activity against the cancer cell lines is determined using an MTT ((3-(4,5-Dimethylthiazol-2-yl)-2, 5-diphenyltetrazolium bromide) reduction assay. Briefly, 10 µL of an MTT solution (5 mg/mL in PBS) is added to each well after 48 hours incubation, and incubation continues for a further 4 hours. The reaction is then stopped by the addition of 100 µL isopropanol:HCl (24:1 v/v). The reduction of MTT leads to the production of formazan. Formazan is solubilized by use of a micropipette, and the optical density (O.D.) determined in a microplate reader at a wavelength of 570 nm against appropriate controls. The percentage inhibition of cell proliferation is determined using the equation:

% Inhibition=100−[(Test O.D.−Control O.D.)/Control O.D.].

The results show that heat-treated MapRNC has dose-related anti-proliferative activity against RT4 bladder cancer cells and CT26 colon cancer cells as well as Jurkat leukemic cells. MapRNC therefore has anticancer activity that is not restricted to cancer type.

EXAMPLE 43

Combination MRNC Formulations for Immune Stimulation

One of skill in the art after reading the above examples will use an appropriate combination of MRNC to achieve optimal therapeutic activity for the desired indication. Thus, a combination of MpRNC and MvRNC will give optimal NOD2 and TLR2 activation for immune stimulation and cytokine induction. Similarly, a combination of MpRNC and MvRNC will give optimal anticancer activity and immune stimulation.

EXAMPLE 44

Combination of MRNC with Therapeutic Agents Used in the Treatment of Cancer

MRNC compositions of the present invention are combined with chemotherapy and/or immunotherapy in order to enhance clinical effectiveness. The addition of MRNC to the following chemotherapeutic regimens is not intended to be a comprehensive listing (such listing are available in for example The Elsevier Guide to Oncology Drugs and Regimens, 2006, which describes more than 220 drug regimens commonly in the treatment of cancer), and it is to be understood that those skilled in the art will, after reading the examples of the present invention, use the compositions of the present invention in the treatment of cancer in neoadjuvant or adjuvant settings with the most appropriate chemotherapy regimens. The following 2 protocols serve to illustrate the principle of how MRNC is used in combination with chemotherapy and immunotherapy:

Colon and rectum cancers: Patients with colon and rectum cancers who have locally advanced disease are at high risk for liver metastases through hepatic portal vein seeding of the liver. Chemotherapy is often initiated prior to or after surgical resection (neoadjuvant or adjuvant settings) with the aim of reducing the incidence of hepatic metastases and subsequent secondary metastasis to other organs. 5-fluorouracil is often used in the treatment of metastatic or advanced disease using a regimen of 1000 mg/m$^2$ by continuous IV infusion daily for 5 days which is repeated every 28 days. MRNC of the present invention can be given as an intravenous bolus or infusion at a therapeutically active dose (determined through clinical evaluation studies) prior to, during or after treatment with 5-fluorouracil. MRNC formulations may be administered at a dose determined in preclinical testing and clinical evaluations (phase-1, phase-2 and phase-3 clinical studies) to be the most effective. Such doses will be in the range 0.00001 mg/kg to about 100 mg/kg per dose. Patients receiving combined therapy benefit from increased time to recurrence, decreased metastases, decreased tumor burden or eradication of tumor when compared to patients who receive 5-fluorouracil therapy alone. Use may be made of other chemotherapy regimens known to those skilled in the art such as but not limited to 5-fluorouracil, leucovorin and oxaliplatin with or without bevacizumab; irinotecan, leucovorin and 5-fluorouracil, with or without cetuximab; or mitomycin c and 5-fluorouracil, without limiting the effectiveness of MRNC.

Lung cancer: Cyclophosphamide in combination with other chemotherapeutic agents is used for the treatment previously untreated patients, or patients with advanced, recurrent or metastatic cancer. Typical regimens are but not limited to cyclophosphamide, doxorubicin (Adriamycin) and etoposide (CAE), where cyclophosphamide is administered at a dose of 1000 mg/m$^2$ I.V. on day 1, doxorubicin is administered at a dose of 45 mg/m$^2$ I.V. on day 1, and etoposide is administered at a dose of 100 mg/m$^2$ I.V. on days 1 through 3. The treatment cycle is repeated every 28 days. MRNC of the present invention is administered as an I.V. bolus at an optimal dose (determined MRNC formulations may be administered at a dose determined in preclinical testing and clinical evaluations (phase-1, phase-2 and phase-3 clinical studies) to be the most effective for enhancing macrophage and granulocyte production through the stimulation of MU-CSF, G-CSF and GM-CSF either prior to, during or after each chemotherapeutic drug treatment cycle. Such doses will be in the range 0.00001 mg/kg to about 100 mg/kg per dose. Patients treated with MRNC have a reduced incidence of infectious episodes and delayed treatment cycles related to chemotherapy-induced reductions in monocyte and neutrophil counts when compared to patients treated with chemotherapy alone. Use may be made of other chemotherapy regimens for the treatment of lung cancer (primary or metastatic) without limiting the effectiveness of MRNC.

Cervical cancer: Cervical cancer is associated with HPV infection. Although some 15 HPV types are oncogenic, HPV16 and 16 are believed to be responsible for 70% of all cervical cancers. Current immunization protocols are effective in preventing infection, but are not effective in treating established infections. There is an unmet need in the treatment of cervical cancer where therapy against the cancer cells and an ongoing viral infection is required if cervical function is to be preserved. Advanced, recurrent or metastatic disease is treated with carboplatin 50-100 mg/m2 I.V. and doxorubicin 45-60 mg/m2 I.V. on day 1, and the cycle is repeated every 21 days. MRNC is administered locally into the cervix by intracervical injection at a dose determined to be optimal for immune stimulation through previous clinical investigation prior to, during or after chemotherapy. MRNC formulations may be administered at a dose determined in preclinical and clinical evaluations (phase-1, phase-2 and phase-3 clinical studies) to be the most effective. Such doses will be in the range 0.00001 mg/kg to about 100 mg/kg per dose. MRNC has 2 effects, first there is a reduction in viral load of HPV viruses (including HPV 16 and 18) in the cervix through the generation of an immune response against the virally-infected cells via the induction of an immune response, and second, an augmentation of the clinical effectiveness of the chemotherapeutic agents through the induction of MU-CSF, G-CSF and GM-CSF.

All patents, publications and abstracts cited above are incorporated herein by reference in their entirety. It should be understood that the foregoing relates only to different embodiments of the present invention and that numerous modifications or alterations may be made therein without departing from the spirit and the scope of the present invention as defined in the following claims.

We claim:
1. A method of making a composition comprising isolated mycobacterial RNA associated with mycobacterial cell wall fragments, comprising the sequential steps of:
    A) disrupting a mycobacterial cell biomass to generate mycobacterial cell wall fragments, mycobacterial cell wall fragments and associated RNA, disrupted mycobacterial cells, intact mycobacterial cells, and mycobacterial RNA;
    B) optionally separating intact mycobacterial cells from the generated mycobacterial cell wall fragments and associated RNA; and,
    C) separating the soluble, cytosolic contents of a portion of the disrupted mycobacterial cells from the generated mycobacterial cell wall fragments and associated mycobacterial RNA to obtain a composition comprising mycobacterial cell wall fragments and associated RNA,
    wherein the composition comprising the isolated mycobacterial RNA associated with the mycobacterial cell wall fragments does not contain phenol or *Streptomyces griseus* protease.
2. The method of claim 1, wherein the isolated mycobacterial RNA associated with mycobacterial cell wall fragments is in the form of oligoribonucleotides and polyribonucleotides of about 2 to about 150 bases in length.
3. The method of claim 1, further comprising after step A, optional step B or after step C a step of heating a composition obtained in a previous step at a temperature sufficient to generate oligoribonucleotides and polyribonucleotides of about 2 to about 150 bases in length, wherein the intact mycobacterial cells are inactivated.
4. The method of claim 1, wherein the disrupting step A comprises high pressure homogenization at about 10,000 psi or higher.
5. The method of claim 1, wherein the disrupting step A is repeated 2 to 5 times before the separation steps B or C.
6. The method of claim 1, further comprising repeating the disrupting step A 2 to 5 times after the separation step C.
7. The method of claim 1, wherein the separating step B is low speed centrifugation and the separating step C is high speed centrifugation.
8. The method of claim 1, further comprising:
    repeating step A and optionally step B to control the number of the intact mycobacterial cells; and,
    after step A, optional step B or after step C a step of heating a composition obtained in a previous step to a temperature sufficient to obtain oligoribonucleotides and polyribonucleotides of about 2 to about 150 bases in length.

9. A method of making a composition comprising isolated bacterial RNA associated with bacterial cell wall fragments comprising the sequential steps of:
    A) disrupting a bacterial cell biomass to generate bacterial cell wall fragments, bacterial cell wall fragments and associated RNA, disrupted bacterial cells, intact bacterial cells, and bacterial RNA;
    B) optionally separating intact bacterial cells from the generated bacterial cell wall fragments and associated RNA; and,
    C) separating the soluble, cytosolic contents of a portion of the disrupted bacterial cells from the generated bacterial cell wall fragments and associated RNA to obtain a composition comprising the bacterial cell wall fragments and associated RNA,
    wherein the composition comprising the isolated bacterial RNA associated with bacterial cell wall fragments does not contain phenol or *Streptomyces griseus* protease.
10. The method of claim 9, wherein the isolated bacterial RNA associated with bacterial cell wall fragments are from gram positive bacteria or gram negative bacteria.
11. The method of claim 9, wherein the isolated bacterial RNA associated with bacterial cell wall fragments is in the form of oligoribonucleotides and polyribonucleotides of about 2 to about 150 bases in length.
12. The method of claim 9, wherein the isolated bacterial RNA associated with bacterial cell wall fragments is in the form of oligoribonucleotides and polyribonucleotides of about 2 to about 40 bases in length.
13. The method of claim 9, further comprising after step A, optional step B or step C a step of heating a composition obtained in a previous step at a temperature sufficient to generate oligoribonucleotides and polyribonucleotides of about 2 to about 150 bases in length.
14. The method of claim 13, wherein the intact bacterial cells are inactivated during the step of heating.
15. The method of claim 13, wherein the temperature is sufficient to generate oligoribonucleotides and polyribonucleotides of about 2 to about 40 bases in length.
16. The method of claim 1, wherein the mycobacterial cell is selected from the group consisting of *Mycobacterium phlei, Mycobacterium vaccae, Mycobacterium smegmatis, Mycobacterium avium* subspecies paratuberculosis and *Mycobacterium bovis* BCG.
17. The method of claim 1, wherein the mycobacterial cell is *Mycobacterium phlei*.
18. The method of claim 1, wherein the isolated mycobacterial RNA associated with bacterial cell wall fragments is in the form of oligoribonucleotides and polyribonucleotides of about 2 to about 40 bases in length.
19. The method of claim 3, wherein the temperature is sufficient to generate oligoribonucleotides and polyribonucleotides of about 2 to about 40 bases in length.
20. The method of claim 8, wherein the temperature is sufficient to generate oligoribonucleotides and polyribonucleotides of about 2 to about 40 bases in length.
21. A method of making a composition comprising isolated mycobacterial RNA associated with mycobacterial cell wall fragments, comprising the steps of:
    A) disrupting a mycobacterial cell biomass to generate mycobacterial cell wall fragments, mycobacterial cell wall fragments and associated RNA, disrupted mycobacterial cells, intact mycobacterial cells, and mycobacterial RNA;
    B) optionally separating intact mycobacterial cells from the generated mycobacterial cell wall fragments and associated RNA;

C) separating the soluble, cytosolic contents of a portion of the disrupted mycobacterial cells from the generated mycobacterial cell wall fragments and associated mycobacterial RNA to obtain a composition comprising mycobacterial cell wall fragments and associated RNA; and, after step A, optional step B or after step C a step of heating a composition obtained in a previous step at a temperature sufficient to generate oligoribonucleotides and polyribonucleotides of about 2 to about 150 bases in length.

22. The method of claim 21, wherein the intact mycobacterial cells are inactivated during the step of heating.

23. The method of claim 21, wherein the composition does not contain phenol or *Streptomyces griseus* protease.

24. The method of claim 21, wherein the mycobacterial cell is selected from the group consisting of *Mycobacterium phlei, Mycobacterium vaccae, Mycobacterium smegmatis, Mycobacterium avium* subspecies *paratuberculosis* and *Mycobacterium bovis* BCG.

25. The method of claim 21, wherein the mycobacterial cell is *Mycobacterium phlei*.

26. The method of claim 21, wherein the disrupting step A comprises high pressure homogenization at about 10,000 psi or higher.

27. The method of claim 21, wherein the disrupting step A is repeated 2 to 5 times before the separation steps B or C.

28. The method of claim 21, further comprising repeating the disrupting step A 2 to 5 times after the separation step C.

29. The method of claim 21, wherein the separating step B is low speed centrifugation and the separating step C is high speed centrifugation.

30. The method of claim 21, further comprising repeating step A and optionally step B to control the number of the intact mycobacterial cells.

31. The method of claim 21, wherein the temperature is sufficient to generate oligoribonucleotides and polyribonucleotides of about 2 to about 40 bases in length.

32. A method of making a composition comprising isolated bacterial RNA associated with bacterial cell wall fragments comprising the steps of:

A) disrupting a bacterial cell biomass to generate bacterial cell wall fragments, bacterial cell wall fragments and associated RNA, disrupted bacterial cells, intact bacterial cells, and bacterial RNA;

B) optionally separating intact bacterial cells from the generated bacterial cell wall fragments and associated RNA;

C) separating the soluble, cytosolic contents of a portion of the disrupted bacterial cells from the generated bacterial cell wall fragments and associated RNA to obtain a composition comprising bacterial cell wall fragments and associated RNA; and, after step A, optional step B or step C a step of heating a composition obtained in a previous step at a temperature sufficient to generate oligoribonucleotides and polyribonucleotides of about 2 to about 150 bases in length.

33. The method of claim 32, wherein the composition comprising the isolated bacterial RNA associated with bacterial cell wall fragments does not contain phenol or *Streptomyces griseus* protease.

34. The method of claim 32, wherein the isolated bacterial RNA associated with bacterial cell wall fragments are from gram positive bacteria or gram negative bacteria.

35. The method of claim 32, wherein the intact bacterial cells are inactivated during the step of heating.

36. The method of claim 32, wherein the temperature is sufficient to generate oligoribonucleotides and polyribonucleotides of about 2 to about 40 bases in length.

* * * * *